United States Patent
Jacobsen et al.

(10) Patent No.: US 8,859,812 B2
(45) Date of Patent: Oct. 14, 2014

(54) COMPOUND REAGENTS AND METHOD FOR SYNTHESIZING ENANTIOMERICALLY ENRICHED AMINO ACIDS

(75) Inventors: Eric N. Jacobsen, Cambridge, MA (US); Stephan J. Zuend, Mannheim (DE)

(73) Assignee: President and Fellows of Harvard College, Cambridge, MA (US)

( * ) Notice: Subject to any disclaimer, the term of this patent is extended or adjusted under 35 U.S.C. 154(b) by 39 days.

(21) Appl. No.: 13/394,693

(22) PCT Filed: Sep. 8, 2010

(86) PCT No.: PCT/US2010/048136
§ 371 (c)(1),
(2), (4) Date: Oct. 15, 2012

(87) PCT Pub. No.: WO2011/031764
PCT Pub. Date: Mar. 17, 2011

(65) Prior Publication Data
US 2013/0066109 A1    Mar. 14, 2013

Related U.S. Application Data

(60) Provisional application No. 61/240,558, filed on Sep. 8, 2009.

(51) Int. Cl.
| | | |
|---|---|---|
| C07C 335/00 | (2006.01) | |
| C07C 253/08 | (2006.01) | |
| C07D 307/52 | (2006.01) | |
| C07D 333/20 | (2006.01) | |
| C07C 227/26 | (2006.01) | |
| C07C 335/16 | (2006.01) | |

(52) U.S. Cl.
CPC .......... *C07C 253/08* (2013.01); *C07C 2101/16* (2013.01); *C07C 2103/74* (2013.01); *C07D 307/52* (2013.01); *C07D 333/20* (2013.01); *C07C 227/26* (2013.01); *C07C 335/16* (2013.01); *C07C 2101/14* (2013.01)
USPC ........................................................ 564/27

(58) Field of Classification Search
USPC ............................................. 564/27, 17, 230
See application file for complete search history.

(56) References Cited

PUBLICATIONS

Reisman et al. (Enantioselective Thiourea-Catalyzed Additions to Oxocarbenium Ions, J. American Chemical Society, vol. 130, pp. 7198-7199, 2008.*
Jacobsen et al. (Enantioselective Thiourea-Catalyzed Additions to Oxocarbenium Ions, J. Am. Chem. Soc., 130, 7198-7199, May 14, 2008).*
Jacobsen et al. (Structure-Based Analysis and Optimization of a highly Enantioselective Catalyst for the Strecker Reaction, J. Am. Chem. Soc., 124, 10012-10014, Aug. 3, 2002).*
International Preliminary Report on Patentability for PCT/US2010/048136 dated Mar. 13, 2012.
International Search Report for PCT/US2010/048136 dated Nov. 4, 2011.
Pan et al: "Catalytic Acylcyanation of Imines with Acetylcyanide", Synlett, No. 19, Nov. 23, 2006, pp. 3275-3276.
Raheem, et al: "Enantioselective Pictet-Spengler-Type Cyclizations of Hydrolactams: H-Bond donar Catalysis by Anion Binding", J.A.C.S, vol. 129, No. 44 Oct. 17, 2007, pp. 13404-13405.
Vachal et al: "Structure-Based Analysis and Optimization of a Highly Enantioselective Catalyst for the Strecker Reaction", J.A.C.S., vol. 124, Aug. 3, 2002, pp. 10012-10014.
Written Opinion for PCT/US2010/048136 dated Mar. 13, 2012.
Zuend et al: "Cooperative Catalysis by Tertiary Amino-Thioureas: Mechanis and Basis for Enantioselectivity of Ketone Cyanosilylation", JACS, vol. 129, No. 51, Dec. 5, 2007, pp. 15872-15883.

* cited by examiner

*Primary Examiner* — Brandon Fetterolf
*Assistant Examiner* — Blaine G Doletski

(57) ABSTRACT

Described herein are compounds of formula (I), related compositions, and their use, for example in the formation of α-amino acids or a precursor thereof such as an α-aminonitrile.

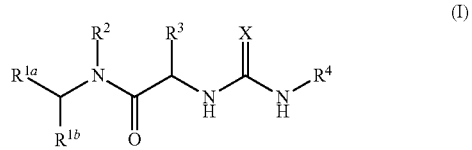

13 Claims, No Drawings

COMPOUND REAGENTS AND METHOD FOR SYNTHESIZING ENANTIOMERICALLY ENRICHED AMINO ACIDS

CROSS-REFERENCE TO RELATED APPLICATIONS

This application is a national stage application under 35 U.S.C. §371 of International Application No.: PCT/US2010/048136, filed Sep. 8, 2010, (the disclosure of which is considered part of (and is incorporated by reference in) the disclosure of this application), which claims priority from U.S. Ser. No. 61/240,558, filed Sep. 8, 2009, which is incorporated herein by reference in its entirety.

GOVERNMENT SUPPORT STATEMENT

This invention was made with government support under GM043214 awarded by the National Institutes of Health. The government has certain rights in the invention.

BACKGROUND OF INVENTION

Natural and unnatural α-amino acids are essential building blocks for protein synthesis, and are also widely useful as components of medicinally active molecules and chiral catalysts (See e.g., Bhat, et al. *Chemistry of Natural Products*, Springer: Narosa, 2005, pp. 317-393; Wang et al., Expanding the genetic code, *Angew. Chem., Int. Ed.*, 44, 34-66 (2005); Davie et al., Asymmetric catalysis mediated by synthetic peptides, *Chem. Rev.* 107, 5759-5812 (2007); and Helmchen et al., Phosphinooxazolines—a new class of versatile, modular P,N-ligands for asymmetric catalysis, *Acc. Chem. Res.* 33, 336-345 (2000)). The Strecker synthesis—the reaction of an imine or imine equivalent with hydrogen cyanide, followed by nitrile hydrolysis—is an especially versatile chemical method for the synthesis of racemic α-amino acids (See e.g., Block et al., The isolation and synthesis of the naturally occurring α-amino acids. *Chem. Rev.* 38, 501-571 (1946), Miller, S. L. Production of some organic compounds under possible primitive earth conditions, *J. Am. Chem. Soc.* 77, 2351-2361 (1955)). Asymmetric Strecker syntheses using stoichiometric chiral reagents have been applied successfully on gram-to-multi-kilogram scales to the preparation of enantiomerically enriched α-amino acids (See e.g., Harada, K. Asymmetric synthesis of α-amino acids by the Strecker synthesis, *Nature* 200, 1201 (1963); Kuethe et al. A concise synthesis of (S)—N-ethoxycarbonyl-α-methylvaline, *J. Org. Chem.* 72, 7469-7472 (2007); and Shu et al., Synthesis of enantiopure Fmoc-α-methylvaline, *Org. Proc. Res. Dev.* 12, 298-300 (2008)). In principle, Strecker syntheses employing sub-stoichiometric quantities of a chiral reagent may provide a practical alternative to these approaches, but the reported catalytic asymmetric methods have seen only limited use on preparative scales (e.g., >1 gram) (See Gröger et al. Catalytic enantioselective Strecker reactions and analogous syntheses, *Chem. Rev.* 103, 2795-2827 (2003); Merino et al., Organocatalyzed Strecker reactions, *Tetrahedron* 65, 1219-1234 (2009)).

The limited use of existing catalytic methodologies may be ascribed to several important practical drawbacks, including the relatively complex and precious nature of the catalysts, and to the requisite use of hazardous cyanide sources in the procedures. Thus, a need for new catalytic asymmetric methods for synthesizing enantiomerically enriched amino acids remains.

SUMMARY OF INVENTION

The inventors have discovered novel compounds, which can be used, for example, to make α-amino acids, or a precursor thereof (e.g., an α-aminonitrile). In some embodiments, the compounds are chrially enriched, and can provide a chirally enriched compound such as a chirally enriched α-aminonitrile or α-amino acid. These compounds, and related compositions and methods of use are described herein.

In one aspect, the invention is directed to a compound or pharmaceutically acceptable salt thereof selected from the formula (I):

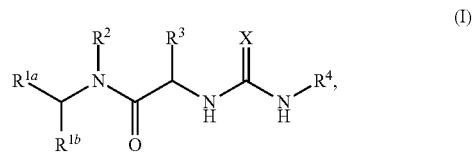

wherein

X is selected from O, S and $NR^5$;

$R^{1a}$ and $R^{1b}$ are each independently selected from optionally substituted alkyl, optionally substituted aryl, optionally substituted heteroaryl, optionally substituted cycloalkyl, optionally substituted heterocyclyl or

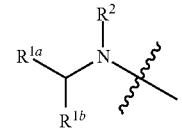

may form an optionally substituted heterocyclic ring;

$R^2$ is hydrogen, optionally substituted alkyl or when taken together with $R^{1a}$ or $R^{1b}$ and the atoms to which they are attached form an optionally substituted heterocyclyl ring;

$R^3$ is optionally substituted alkyl, optionally substituted aryl, optionally substituted cycloalkyl, optionally substituted heteroaryl, optionally substituted heterocyclyl, optionally substituted aralkyl, optionally substituted heteroaralkyl, or optionally substituted heterocyclylalkyl;

$R^4$ is optionally substituted alkyl, optionally substituted cycloalkyl, optionally substituted aryl, optionally substituted heteroaryl, optionally substituted heterocyclyl, optionally substituted heteroaralkyl, optionally substituted aralkyl or optionally substituted heterocyclylalkyl; and $R^5$ is hydrogen, alkyl, aryl, or arylalkyl; and when one of $R^{1a}$ or $R^{1b}$ is phenyl and the other is alkyl, the alkyl must be substituted or branched.

In some embodiments, the compound of formula (I) is enantiomerically enriched for the R isoform (e.g., having at least about 50%, 55%, 60%, 65%, 70%, 75%, 80%, 85%, 90%, 95%, 97%, 98%, or 99% ee for the R isoform). In some embodiments, the compound of formula (I) is enantiomerically enriched for the S isoform (e.g., having at least about 50%, 55%, 60%, 65%, 70%, 75%, 80%, 85%, 90%, 95%, 97%, 98%, or 99% ee for the R isoform).

In some embodiments, the compound is a compound of formula (Ia)

(Ia)

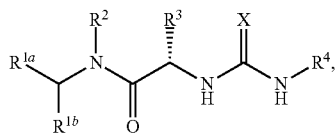

wherein the compound has an ee of at least about 50% (e.g., at least about 55%, 60%, 65%, 70%, 75%, 80%, 85%, 90%, 95%, 97%, 98%, or 99%).

In some embodiments, the compound is a compound of formula (Ib)

(Ib)

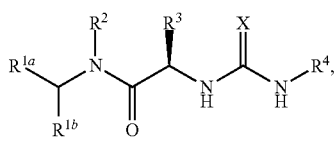

wherein the compound has an ee of at least about 50% (e.g., at least about 55%, 60%, 65%, 70%, 75%, 80%, 85%, 90%, 95%, 97%, 98%, or 99%).

In some embodiments, X is selected from O and S. In some embodiments, X is S.

In certain embodiments, $R^{1a}$ and $R^{1b}$ are each independently selected from optionally substituted alkyl or optionally substituted aryl. In some embodiments, $R^{1a}$ or $R^{1b}$ is optionally substituted aryl. In some embodiments, $R^{1a}$ and $R^{1b}$ is optionally substituted aryl. In some embodiments, $R^{1a}$ is phenyl. In some embodiments, $R^{1b}$ is phenyl. In some embodiments, at least one of $R^{1a}$ or $R^{1b}$ is a branched alkyl.

In certain embodiments, $R^2$ is hydrogen or $C_{1-8}$ alkyl. In some embodiments, $R^2$ is hydrogen. In some embodiments, $R^2$ is a primary alkyl (e.g., methyl).

In certain embodiments,

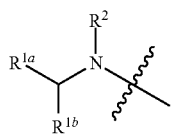

forms an optionally substituted 5-8 membered heterocyclic ring. In some embodiments,

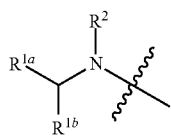

forms an optionally substituted 5-membered heterocyclic ring. In some embodiments,

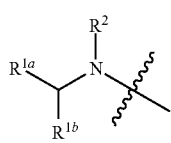

forms the following structure:

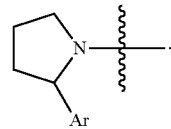

In certain embodiments, Ar is optionally substituted aryl. In some embodiments, Ar is an aryl group containing 1-4 rings. In some embodiments, Ar is an aryl group containing 1 ring (e.g., phenyl). In some embodiments, Ar is an aryl group containing 2 rings (e.g., 1-naphthyl or 2-naphthyl). In some embodiments, Ar is an aryl group containing 3 rings (e.g., anthryl). In some embodiments, Ar is an aryl group containing 4 rings (e.g., pyrenyl). In some embodiments, Ar is phenyl, 1-naphthyl, 2-naphthyl, anthryl, or pyrenyl.

In certain embodiments,

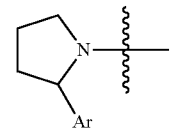

is enantiomerically enriched for the R or S isoform. In some embodiments,

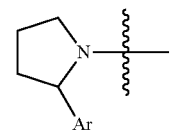

is enantiomerically enriched for the R isoform (e.g., having at least about 50%, 55%, 60%, 65%, 70%, 75%, 80%, 85%, 90%, 95%, 97%, 98%, or 99% ee for the R isoform). In some embodiments,

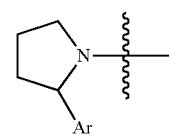

is enantiomerically enriched for the S isoform (e.g., having at least about 50%, 55%, 60%, 65%, 70%, 75%, 80%, 85%, 90%, 95%, 97%, 98%, or 99% ee for the R isoform).

In certain embodiments, $R^3$ is optionally substituted alkyl or optionally substituted aryl. In some embodiments, $R^3$ is $C_{1-8}$ alkyl or optionally substituted aryl. In some embodiments, $R^3$ is $C_{1-8}$ alkyl. In some embodiments, $R^3$ is $C_{1-4}$ alkyl (e.g., t-butyl, i-propyl, i-butyl, or s-butyl).

In certain embodiments, $R^4$ is optionally substituted alkyl, optionally substituted cycloalkyl, or optionally substituted aryl. In some embodiments, $R^4$ is optionally substituted $C_{3-10}$ cycloalkyl or optionally substituted aryl. In some embodiments, $R^4$ is $C_{3-10}$ cycloalkyl. In some embodiments, $R^4$ is $C_{5-8}$ cycloalkyl. In some embodiments, $R^4$ is cyclohexyl. In some embodiments, $R^4$ is optionally substituted phenyl. In some embodiments, $R^4$ is aryl, substituted with a compound selected from halo, nitro, cyano, haloalkyl, $C_{1-8}$ alkoxy, and $C_{1-8}$ alkyl. In some embodiments, $R^4$ is aryl, substituted with a compound selected from halo, haloalkyl, nitro and $C_{1-8}$ alkyl. In some embodiments, $R^4$ is aryl, substituted with a compound selected from halo (e.g., chloro). In some embodiments, $R^4$ is aryl, substituted with a compound selected from haloalkyl (e.g., trifluoromethyl). In some embodiments, $R^4$ is aryl, substituted with a compound selected from nitro. In some embodiments, $R^4$ is aryl, substituted with a compound selected from $C_{1-8}$ alkyl (e.g., methyl, ethyl, i-propyl or t-butyl).

In some embodiments, the compound of formula (I) is selected from a compound of formula (Ic):

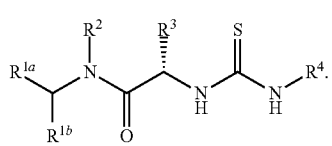

(Ic)

In some embodiments, the compound of formula (I) is selected from a compound of formula (Id):

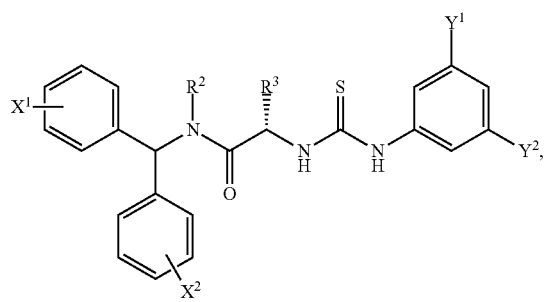

(Id)

wherein $X^1$, $X^2$, $Y^1$ and $Y^2$ are each independently selected from hydrogen, alkyl, alkoxy or haloalkyl.

In some embodiments, $X^1$ is hydrogen. In some embodiments, $X^2$ is hydrogen. In some embodiments, $Y^1$ is haloalkyl (e.g., trifluoromethyl). In some embodiments, $Y^2$ is haloalkyl (e.g., trifluoromethyl).

In some embodiments, the compound of formula (I) is

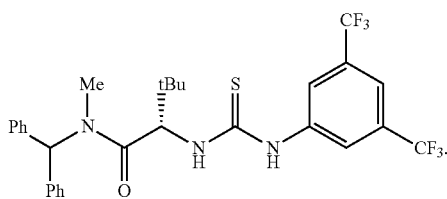 [SMILES: CN(C(=O)[C@@H](NC(=S)Nc1cc(C(F)(F)F)cc(C(F)(F)F)c1)C(C)(C)C)C(c1ccccc1)c1ccccc1]

In another aspect, the invention is directed to a complex comprising a compound of formula (I) and a cyanide source.

In certain embodiments, the complex further comprises an imine. In some embodiments, the imine is a protected imine. In some embodiments, the imine is an N-benzhydryl protected imine.

In certain embodiments, the cyanide source is KCN. In some embodiments, the cyanide source is HCN. In some embodiments, the cyanide source is NaCN. In some embodiments, the cyanide source is LiCN. In some embodiments, the cyanide source is a trialkylsilyl cyanide. In some embodiments, the tialkylsilyl cyanide is $Me_3SiCN$.

In another aspect, the invention is directed to a composition comprising a compound of formula (I).

In certain embodiments, the composition further comprises a cyanide source.

In certain embodiments, the composition further comprises one or more solvents. In some embodiments, the composition further comprises an organic and aqueous solvent. In some embodiments, the organic solvent is toluene. In some embodiments, the aqueous solvent is pharmaceutically acceptable water ($H_2O$).

In some embodiments, the composition comprises one or more reagents. In some embodiments, the one or more reagents comprises an imine. In some embodiments, the imine is a protected imine. In some embodiments, the imine is an N-benzhydryl protected imine.

In some embodiments, the one or more reagents is a compound of formula

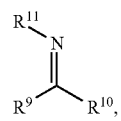

(II)

wherein
$R^9$ and $R^{10}$ are each independently selected from hydrogen, optionally substituted alkyl, optionally substituted alkenyl, optionally substituted cycloalkyl, optionally substituted cycloalkenyl, optionally substituted heterocyclyl, optionally substituted heteroaryl and optionally substituted aryl, wherein $R^9$ and $R^{10}$ are different; and $R^{11}$ is selected from hydrogen, optionally substituted alkyl, optionally substituted cycloalkyl, optionally substituted aryl, optionally substituted aralkyl, optionally substituted heteroaryl, optionally substituted heteroaralkyl, optionally substituted heterocyclyl and optionally substituted heterocyclylalkyl.

In some embodiments, the one or more reagents is a compound of formula

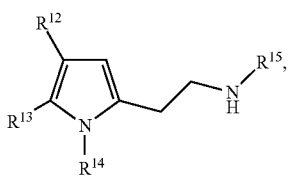

(IV)

wherein
$R^{12}$ is from hydrogen, optionally substituted alkyl, optionally substituted aryl, optionally substituted heteroaryl or when taken together with $R^{13}$ and the carbon atoms to which they are attached form an optionally substituted aryl or heteroaryl ring;

$R^{13}$ is from hydrogen, optionally substituted alkyl, optionally substituted aryl, optionally substituted heteroaryl or when taken together with $R^{12}$ and the carbon atoms to which they are attached form an optionally substituted aryl or heteroaryl ring; and $R^{14}$ and $R^{15}$ are each independently hydrogen or optionally substituted alkyl.

In some embodiments, the one or more reagents is an aldehyde of formula (V):

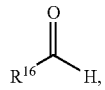

(V)

wherein
$R^{16}$ is hydrogen, optionally substituted alkyl, optionally substituted aryl, optionally substituted heteroaryl or halogen.

In some embodiments, the composition is substantially free of water.

In some embodiments, the composition comprises a source of cyanide. In some embodiments, the cyanide source is KCN. In some embodiments, the cyanide source is HCN. In some embodiments, the cyanide source is NaCN. In some embodiments, the cyanide source is LiCN. In some embodiments, the cyanide source is a trialkylsilyl cyanide. In some embodiments, the tialkylsilyl cyanide is $Me_3SiCN$.

In certain embodiments, the composition further comprises an acid. In some embodiments, the acid is acetic acid.

In another aspect, the invention is directed to a reaction mixture comprising a compound of formula (I).

In some embodiments, the reaction mixture further comprises a cyanide source. In some embodiments, the cyanide source is KCN. In some embodiments, the cyanide source is HCN. In some embodiments, the cyanide source is NaCN. In some embodiments, the cyanide source is LiCN. In some embodiments, the cyanide source is a trialkylsilyl cyanide. In some embodiments, the trialkylsilyl cyanide is $Me_3SiCN$.

In some embodiments, the reaction mixture further comprises one or more solvents. In some embodiments, the reaction mixture further comprises an organic and aqueous solvent. In some embodiments, the organic solvent is toluene. In some embodiments, the aqueous solvent is pharmaceutically acceptable water ($H_2O$).

In some embodiments, the composition comprises one or more reagents. In some embodiments, the one or more reagents comprises an imine. In some embodiments, the imine is a protected imine. In some embodiments, the imine is an N-benzhydryl protected imine.

In some embodiments, the one or more reagents is a compound of formula

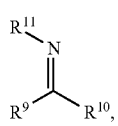

(II)

wherein
$R^9$ and $R^{10}$ are each independently selected from hydrogen, optionally substituted alkyl, optionally substituted alkenyl, optionally substituted cycloalkyl, optionally substituted cycloalkenyl, optionally substituted heterocyclyl, optionally substituted heteroaryl and optionally substituted aryl, wherein $R^9$ and $R^{10}$ are different; and
$R^{11}$ is selected from hydrogen, optionally substituted alkyl, optionally substituted cycloalkyl, optionally substituted aryl, optionally substituted aralkyl, optionally substituted heteroaryl, optionally substituted heteroaralkyl, optionally substituted heterocyclyl and optionally substituted heterocyclylalkyl.

In some embodiments, the one or more reagents is a compound of formula

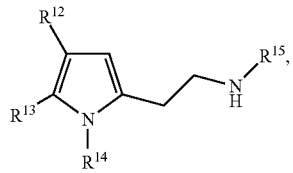

(IV)

wherein
$R^{12}$ is from hydrogen, optionally substituted alkyl, optionally substituted aryl, optionally substituted heteroaryl or when taken together with $R^{13}$ and the carbon atoms to which they are attached form an optionally substituted aryl or heteroaryl ring;
$R^{13}$ is from hydrogen, optionally substituted alkyl, optionally substituted aryl, optionally substituted heteroaryl or when taken together with $R^{12}$ and the carbon atoms to which they are attached form an optionally substituted aryl or heteroaryl ring; and
$R^{14}$ and $R^{15}$ are each independently hydrogen or optionally substituted alkyl.

In some embodiments, the one or more reagents is an aldehyde of formula (V):

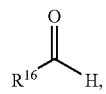

(V)

wherein
$R^{16}$ is hydrogen, optionally substituted alkyl, optionally substituted aryl, optionally substituted heteroaryl or halogen.

In some embodiments, the reaction mixture is substantially free of water.

In certain embodiments, the reaction mixture further comprises an acid. In some embodiments, the acid is acetic acid. In some embodiments, the acid is benzoic acid.

In another aspect, the present invention is directed to a method of making an α-aminonitrile, the method comprising mixing a compound of formula (I) with a substrate and cyanide source under conditions sufficient to produce the α-aminonitrile.

In certain embodiments, the compound of formula (I) is present in a catalytic amount (e.g., 50 mol %, 25 mol %, 15 mol %, 10 mol %, 5 mol %, 1 mol %, 0.5 mol %, 0.25 mol %, 0.1 mol % or less).

In certain embodiments, the substrate is an organic compound of formula (II):

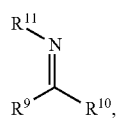

(II)

wherein
$R^9$ and $R^{10}$ are each independently selected from hydrogen, optionally substituted alkyl, optionally substituted alkenyl, optionally substituted cycloalkyl, optionally substituted cycloalkenyl, optionally substituted heterocyclyl, optionally substituted heteroaryl and optionally substituted aryl, wherein $R^9$ and $R^{10}$ are different; and $R^{11}$ is selected from hydrogen, optionally substituted alkyl, optionally substituted cycloalkyl, optionally substituted aryl, optionally substituted aralkyl, optionally substituted heteroaryl, optionally substituted heteroaralkyl, optionally substituted heterocyclyl and optionally substituted heterocyclylalkyl.

In some embodiments, one of $R^9$ and $R^{10}$ is hydrogen. In some embodiments, one of $R^9$ and $R^{10}$ is selected from optionally substituted alkyl and optionally substituted aryl. In some embodiments, one of $R^9$ and $R^{10}$ is selected from $C_{1-8}$ alkyl and aryl. In some embodiments, one of $R^9$ and $R^{10}$ is optionally substituted $C_{1-8}$ alkyl (e.g., methyl). In some embodiments, one of $R^9$ and $R^{10}$ is substituted with $C_{1-8}$ alkyl (e.g., methyl). In some embodiments, one of $R^9$ and $R^{10}$ is a tertiary alkyl (e.g., t-butyl). In some embodiments, one of $R^9$ and $R^{10}$ is optionally substituted aryl (e.g., phenyl, chlorophenyl, trifluorophenyl, cyanophenyl, bromophenyl, or methoxyphenyl). In some embodiments, one of $R^9$ and $R^{10}$ is optionally substituted heteroaryl (e.g., furanyl or thienyl). In some embodiments, one of $R^9$ and $R^{10}$ is cycloalkenyl (e.g., cyclohexenyl).

In certain embodiments, $R^{11}$ is selected from hydrogen, optionally substituted alkyl, optionally substituted aralkyl, optionally substituted heteroaralkyl, and optionally substituted heterocyclylalkyl. In some embodiments, $R^{11}$ is selected from hydrogen, optionally substituted $C_{1-8}$ alkyl and optionally substituted aryl. In some embodiments, $R^{11}$ is selected from $C_{1-8}$ alkyl and aryl. In some embodiments, $R^{11}$ is $C_{1-8}$ alkyl (e.g., methyl). In some embodiments, $R^H$ is selected from aralkyl (e.g., benzyl).

In certain embodiments, the compound of formula (II) is a compound of the following formula:

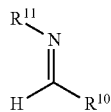

wherein:
$R^{10}$ is optionally substituted alkyl, or optionally substituted aryl; and
$R^{11}$ is as defined above.

In certain embodiments, the compound of formula (II) is a compound of the following formula:

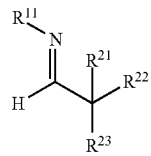

wherein:
$R^{21}$, $R^{22}$, and $R^{23}$ are each independently alkyl, alkenyl, aryl, or heteroaryl and not H; and
$R^{11}$ is as defined above. In some embodiments, each of $R^{21}$, $R^{22}$ and $R^{23}$ is selected from alkyl (e.g., methyl or ethyl).

In certain embodiments, the compound of formula (II) is a compound of the following formula:

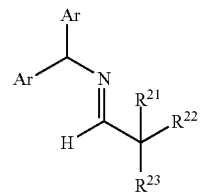

wherein:
$R^{21}$, $R^{22}$, and $R^{23}$ are each independently alkyl, aryl, heteroaryl or heterocyclic groups and not H; and
Ar is any aryl group.

In certain embodiments, the compound of formula (II) is a compound of the following formula:

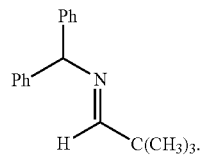

In some embodiments, the cyanide source is KCN. In some embodiments, the cyanide source is HCN. In some embodiments, the cyanide source is NaCN. In some embodiments, the cyanide source is LiCN. In some embodiments, the cyanide source is a trialkylsilyl cyanide. In some embodiments, the trialkylsilyl cyanide is $Me_3SiCN$.

In certain embodiments, the method further comprises an acid. In some embodiments, the acid is acetic acid.

In certain embodiments, the method further comprises one or more solvents. In certain embodiments, the method further comprises an organic and aqueous solvent. In some embodiments, the organic solvent is any non-polar solvent. In some embodiments, the organic solvent is toluene. In some embodiments, the organic solvent is hexanes. In some embodiments, the organic solvent is pentane. In some embodiments, the organic solvent is benzene. In some embodiments, the aqueous solvent is pharmaceutically acceptable water ($H_2O$).

In certain embodiments, the method further comprises an inert atmosphere. In some embodiments, the inert atmosphere is nitrogen ($N_2$) or argon.

In certain embodiments, the method produces the R enantiomer of the α-aminonitrile enriched for the R isoform (e.g., e.g., having at least about 10%, 20%, 30%, 40%, 50%, 55%, 65%, 75%, 80%, 85%, 90%, 95%, 97%, 98%, 99%, 99.5%, 99.9% ee or greater for the R isoform).

In certain embodiments, the method produces the S enantiomer of the α-aminonitrile enriched for the S isoform (e.g., e.g., having at least about 10%, 20%, 30%, 40%, 50%, 55%, 65%, 75%, 80%, 85%, 90%, 95%, 97%, 98%, 99%, 99.5%, 99.9% ee or greater for the S isoform).

In certain embodiments, the method further comprises hydrolyzing the α-aminonitrile. In some embodiments, the method comprises hydrolyzing the α-aminonitrile with an enzyme. In some embodiments, the method comprises hydrolyzing the α-aminonitrile with one or more acid reagents.

In some embodiments, the one or more acid reagents contains HCl. In some embodiments, the method comprising the one or more acid reagents contains $H_2SO_4$. In some embodiments, the method comprising the one or more acid reagents contains HCl and $H_2SO_4$.

In certain embodiments, the method further comprises reacting the product from reaction of the α-aminonitrile with one or more acid and/or base reagents, with a substrate to apply and/or remove an amine protecting group.

In certain embodiments, the method further comprises reacting the product from reaction of the α-aminonitrile with one or more acid reagents, with a substrate to apply an amine protecting group. In some embodiments, the method further comprises an organic solvent. In some embodiments, the organic solvent is dioxane.

In some embodiments, the substrate applies a Boc protecting group to the amine. In some embodiments, the substrate is Boc$_2$O.

In another aspect, the present invention is directed to a method of making a compound of formula (I), the method comprising:

mixing an optionally protected amino acid (e.g., N-Boc leucine) with the appropriate amine under conditions sufficient to produce an aminoacetamide;

removing the optionally protecting group; and reacting with an isocyanate or isothiocyante to produce the desired compound.

In some embodiments, the conditions sufficient to produce an aminoacetamide contain HBTU in the presence of DIPEA base.

In some embodiments, the amine protecting group is Boc.

In some embodiments, the aminoacetamide is reacted with an isocyanate.

In some embodiments, the aminoacetamide is reacted with an isothiocyanate.

In some embodiments, the isothiocyanate is 3,5-bis(trifluoromethyl)phenylisothiocyanate.

In some embodiments, the compound of formula (I) is

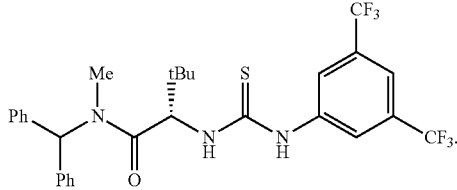 [SMILES: CN(C(=O)[C@@H](NC(=S)Nc1cc(C(F)(F)F)cc(C(F)(F)F)c1)C(C)(C)C)C(c1ccccc1)c1ccccc1]

In another aspect, the present invention is directed to a method of making an α-amino acid, the method comprising:

mixing a compound of formula (I) with a substrate and cyanide source under conditions sufficient to produce a α-aminonitrile;

hydrolyzing the α-aminonitrile; and optionally, deprotecting and/or protecting the resulting α-amino acid.

In some embodiments, the α-aminonitrile is hydrolyzed with an enzyme.

In some embodiments, the α-aminonitrile is hydrolyzed with one or more acid reagents.

In certain embodiments, the yield of the method is 10% or greater (e.g., 20%, 30%, 40%, 50%, 60%, 70%, 80%, 90%, 95% or 99%).

In certain embodiments, the α-amino acid is produced as the desired stereoisomer.

In certain embodiments, the method produces the R enantiomer of the α-amino acid enriched for the R isoform (e.g., e.g., having at least about 10%, 20%, 30%, 40%, 50%, 55%, 65%, 75%, 80%, 85%, 90%, 95%, 97%, 98%, 99%, 99.5%, 99.9% ee or greater for the R isoform).

In certain embodiments, the method produces the S enantiomer of the α-amino acid enriched for the S isoform (e.g., e.g., having at least about 10%, 20%, 30%, 40%, 50%, 55%, 65%, 75%, 80%, 85%, 90%, 95%, 97%, 98%, 99%, 99.5%, 99.9% ee or greater for the S isoform).

In another aspect, the present invention is directed to a method of making a compound of formula (III):

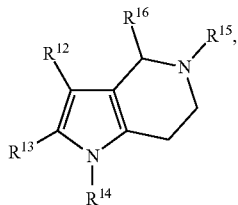

the method comprising, mixing a compound of formula (IV):

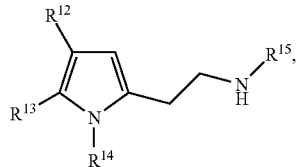

with a compound of formula (I) and an aldehyde of formula (V);

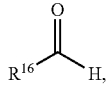

wherein $R^{12}$ is from hydrogen, optionally substituted alkyl, optionally substituted aryl, optionally substituted heteroaryl or when taken together with $R^{13}$ and the carbon atoms to which they are attached form an optionally substituted aryl or heteroaryl ring;

$R^{13}$ is from hydrogen, optionally substituted alkyl, optionally substituted aryl, optionally substituted heteroaryl or when taken together with $R^{12}$ and the carbon atoms to which they are attached form an optionally substituted aryl or heteroaryl ring;

$R^{16}$ is hydrogen, optionally substituted alkyl, optionally substituted aryl, optionally substituted heteroaryl or halogen; and $R^{14}$ and $R^{15}$ are each independently hydrogen or optionally substituted alkyl.

In certain embodiments, $R^{12}$ and $R^{13}$ taken together with the carbon atoms to which they are attached form an optionally substituted aryl ring. In some embodiments, $R^{12}$ and $R^{13}$ taken together with the carbon atoms to which they are attached form an optionally substituted phenyl ring. In some embodiments, $R^{12}$ and $R^{13}$ taken together with the carbon atoms to which they are attached form an unsubstituted phenyl ring. In some embodiments, $R^{12}$ and $R^{13}$ taken together with the carbon atoms to which they are attached form phenyl ring substituted with fluorine (e.g., 2-fluoro, 3-fluoro or 4-fluorophenyl).

In certain embodiments, $R^{14}$ is hydrogen. In certain embodiments, $R^{15}$ is hydrogen.

In certain embodiments, $R^{16}$ is optionally substituted alkyl or optionally substituted aryl. In some embodiments, $R^{16}$ is optionally substituted alkyl (e.g., isopropyl or t-butyl). In some embodiments, $R^{16}$ is optionally substituted aryl (e.g., a monocyclic aryl). In some embodiments, $R^{16}$ is optionally substituted monocyclic aryl (e.g., phenyl). In some embodiments, $R^{16}$ is optionally substituted phenyl. In some embodiments, $R^{16}$ is unsubstituted phenyl. In some embodiments, $R^{16}$ is 4-chlorophenyl. In some embodiments, $R^{16}$ is 2-bromophenyl. In some embodiments, $R^{16}$ is 4-cyanophenyl.

In certain embodiments, the method further comprises an acid. In some embodiments, the acid is acetic acid. In some embodiments, the acid is a carboxylic acid. In some embodiments, the carboxylic acid is benzoic acid.

In certain embodiments, the method further comprises one or more solvents. In certain embodiments, the method further comprises an organic and aqueous solvent. In some embodiments, the organic solvent is any non-polar solvent. In some embodiments, the organic solvent is toluene. In some embodiments, the organic solvent is hexanes. In some embodiments, the organic solvent is pentane. In some embodiments, the organic solvent is benzene. In some embodiments, the aqueous solvent is pharmaceutically acceptable water ($H_2O$).

In certain embodiments, the method further comprises an inert atmosphere. In some embodiments, the inert atmosphere is nitrogen ($N_2$) or argon.

In certain embodiments, the method produces the R enantiomer of a compound of formula (III) enriched for the R isoform (e.g., e.g., having at least about 10%, 20%, 30%, 40%, 50%, 55%, 65%, 75%, 80%, 85%, 90%, 95%, 97%, 98%, 99%, 99.5%, 99.9% ee or greater for the R isoform).

In certain embodiments, the method produces the S enantiomer of a compound of formula (III) enriched for the S isoform (e.g., e.g., having at least about 10%, 20%, 30%, 40%, 50%, 55%, 65%, 75%, 80%, 85%, 90%, 95%, 97%, 98%, 99%, 99.5%, 99.9% ee or greater for the S isoform).

In certain embodiments, the compound of formula (I) is

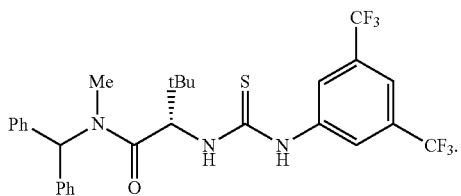 [SMILES: CN(C(=O)[C@@H](NC(=S)Nc1cc(C(F)(F)F)cc(C(F)(F)F)c1)C(C)(C)C)C(c1ccccc1)c1ccccc1]

In certain embodiments, the method is carried out at room temperature.

In another aspect, the present invention is directed to a kit comprising a compound of formula (I) and a container.

In some embodiments, the container is a vial. In some embodiments, the container is a sealed ampule.

In certain embodiments the kit further comprises an inert gas. In some embodiments, the inert gas is >95% $N_2$. In some embodiments, the inert gas is >99% $N_2$. In some embodiments, the inert gas is >99.5% $N_2$. In some embodiments, the inert gas is >99.9% $N_2$. In some embodiments, the inert gas is >95% argon. In some embodiments, the inert gas is >99% argon. In some embodiments, the inert gas is >99.5% argon. In some embodiments, the inert gas is >99.9% argon.

In certain embodiments, the kit further comprises a substrate. In some embodiments, the substrate is an organic compound. In some embodiments, the organic compound is an imine.

In certain embodiments, the kit further comprises an organic solvent.

In some embodiments, the formula concentration is 1.0M or less. In some embodiments, the formula concentration is 0.5M or less. In some embodiments, the formula concentration is 0.1M or less. In some embodiments, the formula concentration is 0.01M or less. In some embodiments, the formula concentration is 0.009M or less. In some embodiments, the formula concentration is 0.0083M. In some embodiments, the organic solvent is toluene.

In some embodiments, the compound of formula (I) is adsorbed on to a solid support (e.g., an inert solid).

Definitions

Definitions of specific functional groups and chemical terms are described in more detail below. For purposes of this invention, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5th Edition, John Wiley & Sons, Inc., New York, 2001; Larock, *Comprehensive Organic Transformations, VCH Publishers, Inc., New York,* 1989; Carruthers, *Some Modern Methods of Organic Synthesis,* 3rd Edition, Cambridge University Press, Cambridge, 1987; the entire contents of each of which are incorporated herein by reference.

Certain compounds of the present invention can comprise one or more asymmetric centers, and thus can exist in various isomeric forms, e.g., stereoisomers and/or diastereomers. Thus, compounds and pharmaceutical compositions thereof may be in the form of an individual enantiomer, diastereomer or geometric isomer, or may be in the form of a mixture of stereoisomers. In certain embodiments, the compounds of the invention are enantiopure compounds. In certain embodiments, mixtures of stereoisomers or diastereomers are provided.

Furthermore, certain compounds, as described herein may have one or more double bonds that can exist as either the Z or E isomer, unless otherwise indicated. The invention additionally encompasses the compounds as individual isomers substantially free of other isomers and alternatively, as mixtures of various isomers, e.g., racemic mixtures of stereoisomers. In addition to the above-mentioned compounds per se, this invention also encompasses pharmaceutically acceptable derivatives of these compounds and compositions comprising one or more compounds.

Where a particular enantiomer is preferred, it may, in some embodiments be provided substantially free of the corresponding enantiomer, and may also be referred to as "optically enriched." "Optically-enriched," as used herein, means that the compound is made up of a significantly greater proportion of one enantiomer. In certain embodiments the compound is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., Enantiomers, Racemates and Resolutions (Wiley Interscience, New York, 1981); Wilen, S. H., et al., Tetrahedron 33:2725 (1977); Eliel, E. L. Stereochemistry of Carbon Compounds (McGraw-Hill, NY, 1962); Wilen, S. H. Tables of Resolving Agents and Optical Resolutions p. 268 (E. L. Eliel, Ed., Univ. of Notre Dame Press, Notre Dame, Ind. 1972).

The compounds of this invention may contain one or more asymmetric centers and thus occur as racemates and racemic mixtures, single enantiomers, individual diastereomers and diastereomeric mixtures. Described herein are enantiomerically enriched compounds (e.g., a compound resolved to an enantiomeric excess of 60%, 70%, 80%, 85%, 90%, 95%, 99% or greater). All such isomeric forms of these compounds are expressly included in the present invention. The compounds of this invention may also contain linkages (e.g., carbon-carbon bonds) or substituents that can restrict bond rotation, e.g. restriction resulting from the presence of a ring or double bond. Accordingly, all cis/trans and E/Z isomers are expressly included in the present invention. The compounds of this invention may also be represented in multiple tautomeric forms, in such instances, the invention expressly includes all tautomeric forms of the compounds described herein, even though only a single tautomeric form may be represented (e.g., alkylation of a ring system may result in alkylation at multiple sites, the invention expressly includes all such reaction products). All such isomeric forms of such compounds are expressly included in the present invention. All crystal forms of the compounds described herein are expressly included in the present invention.

Methods for separating a racemic mixture of two enantiomers include chromatography using a chiral stationary phase (see, e.g., "Chiral Liquid Chromatography," W. J. Lough, Ed. Chapman and Hall, New York (1989)). Enantiomers can also be separated by classical resolution techniques. For example, formation of diastereomeric salts and fractional crystallization can be used to separate enantiomers. For the separation of enantiomers of carboxylic acids, the diastereomeric salts can be formed by addition of enantiomerically pure chiral bases such as brucine, quinine, ephedrine, strychnine, and the like. Alternatively, diastereomeric esters can be formed with enantiomerically pure chiral alcohols such as menthol, followed by separation of the diastereomeric esters and hydrolysis to yield the free, enantiomerically enriched carboxylic acid. For separation of the optical isomers of amino compounds, addition of chiral carboxylic or sulfonic acids, such as camphorsulfonic acid, tartaric acid, mandelic acid, or lactic acid can result in formation of the diastereomeric salts. For example a compound can be resolved to an enantiomeric excess (e.g., 60%, 70%, 80%, 85%, 90%, 95%, 99% or greater) via formation of diastereomeric salts, e.g. with a chiral base, e.g., (+) or (−) α-methylbenzylamine, or via high performance liquid chromatography using a chiral column. In some embodiments a product is purified directly on a chiral column to provide enantiomerically enriched compound.

The "enantiomeric excess" or "% enantiomeric excess" of a composition can be calculated using the equation shown below. In the example shown below a composition contains 90% of one enantiomer, e.g., the S enantiomer, and 10% of the other enantiomer, i.e., the R enantiomer.

$$ee=(90-10)/100=80\%.$$

Thus, a composition containing 90% of one enantiomer and 10% of the other enantiomer is said to have an enantiomeric excess of 80%.

The term "halo" or "halogen" refers to any radical of fluorine, chlorine, bromine or iodine.

The term "haloalkyl" refers to an alkyl group that may have any number of hydrogens available on the group replaced with a halogen atom. Representative haloalkyl groups include but are not limited to: —$CH_2Cl$, —$CH_2ClCF_3$, —$CHBr_2$ or —$CF_3$. The term "fluoroalkyl" refers to an alkyl group that may have any number of hydrogens available on the group replaced with a fluorine atom. Representative fluoroalkyl groups include but are not limited to: —$CH_2F$, —$CH_2FCF_3$, —$CHF_2$ or —$CF_3$. The term "haloalkoxy" refers to an alkoxy group that may have any number of hydrogen atoms available on the alkyl group replaced with a halogen atom. Representative haloalkoxy groups include but are not limited to: —$OCH_2Cl$, —$OCH_2ClCF_3$, —$OCHBr_2$ or —$OCF_3$. The term "fluoroalkoxy" refers to an alkoxy group that may have any number of hydrogens available on the group replaced with a fluorine atom. Representative fluoroalkoxy groups include but are not limited to: —$OCH_2F$, —$OCH_2FCF_3$, —$OCHF_2$ or —$OCF_3$.

The term "alkyl" refers to a hydrocarbon chain that may be a straight chain or branched chain, containing the indicated number of carbon atoms. For example, $C_1$-$C_{12}$ alkyl indicates that the group may have from 1 to 12 (inclusive) carbon atoms in it. The term "haloalkyl" refers to an alkyl in which one or more hydrogen atoms are replaced by halo, and includes alkyl moieties in which all hydrogens have been replaced by halo (e.g., perfluoroalkyl). The terms "arylalkyl" or "aralkyl" refer to an alkyl moiety in which an alkyl hydrogen atom is replaced by an aryl group. Aralkyl includes groups in which more than one hydrogen atom has been replaced by an aryl group. Examples of "arylalkyl" or "aralkyl" include benzyl, 2-phenylethyl, 3-phenylpropyl, 9-fluorenyl, benzhydryl, and trityl groups.

The term "alkylene" refers to a divalent alkyl, e.g., —$CH_2$—, —$CH_2CH_2$—, and —$CH_2CH_2CH_2$—.

The term "alkenyl" refers to a straight or branched hydrocarbon chain containing 2-12 carbon atoms and having one or more double bonds. Examples of alkenyl groups include, but are not limited to, allyl, propenyl, 2-butenyl, 3-hexenyl and 3-octenyl groups. One of the double bond carbons may optionally be the point of attachment of the alkenyl substituent. The term "alkynyl" refers to a straight or branched hydrocarbon chain containing 2-12 carbon atoms and characterized in having one or more triple bonds. Examples of alkynyl groups include, but are not limited to, ethynyl, propargyl, and 3-hexynyl. One of the triple bond carbons may optionally be the point of attachment of the alkynyl substituent.

The terms "alkylamino" and "dialkylamino" refer to —NH(alkyl) and —NH(alkyl)$_2$ radicals respectively. The term "aralkylamino" refers to a —NH(aralkyl) radical. The term alkylaminoalkyl refers to a (alkyl)NH-alkyl-radical; the term dialkylaminoalkyl refers to a (alkyl)$_2$N-alkyl-radical The term "alkoxy" refers to an —O-alkyl radical. The term "mercapto" refers to an SH radical. The term "thioalkoxy" refers to an —S-alkyl radical. The term thioaryloxy refers to an —S-aryl radical.

The term "aryl" refers to an aromatic monocyclic, bicyclic, or tricyclic hydrocarbon ring system, wherein any ring atom capable of substitution can be substituted (e.g., by one or more substituents). Examples of aryl moieties include, but are not limited to, phenyl, naphthyl, and anthracenyl.

The term "arylalkyl" or the term "aralkyl" refers to alkyl substituted with an aryl. Exemplary aralkyls include but are not limited to benzyl and phenethyl.

The term "cycloalkyl" as employed herein includes saturated cyclic, bicyclic, tricyclic, or polycyclic hydrocarbon groups having 3 to 12 carbons. Any ring atom can be substituted (e.g., by one or more substituents). The cycloalkyl groups can contain fused rings. Fused rings are rings that share a common carbon atom. Examples of cycloalkyl moieties include, but are not limited to, cyclopropyl, cyclohexyl, methylcyclohexyl, adamantyl, and norbornyl.

The term "heterocyclyl" refers to a nonaromatic 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). The heteroatom may optionally be the point of attachment of the heterocyclyl substituent. Any ring atom can be substituted (e.g., by one or more substituents). The heterocyclyl groups can contain fused rings. Fused rings are rings that share a common carbon atom. Examples of heterocyclyl include, but are not limited to, tetrahydrofuranyl, tetrahydropyranyl, piperidinyl, morpholino, pyrrolinyl, pyrimidinyl, quinolinyl, and pyrrolidinyl.

The term "heterocyclylalkyl", as used herein, refers to an alkyl group substituted with a heterocycle group.

The term "cycloalkenyl" refers to partially unsaturated, nonaromatic, cyclic, bicyclic, tricyclic, or polycyclic hydrocarbon groups having 5 to 12 carbons, preferably 5 to 8 carbons. The unsaturated carbon may optionally be the point of attachment of the cycloalkenyl substituent. Any ring atom can be substituted (e.g., by one or more substituents). The cycloalkenyl groups can contain fused rings. Fused rings are rings that share a common carbon atom. Examples of cycloalkenyl moieties include, but are not limited to, cyclohexenyl, cyclohexadienyl, or norbornenyl.

The term "heterocycloalkenyl" refers to a partially saturated, nonaromatic 5-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). The unsaturated carbon or the heteroatom may optionally be the point of attachment of the heterocycloalkenyl substituent. Any ring atom can be substituted (e.g., by one or more substituents). The heterocycloalkenyl groups can contain fused rings. Fused rings are rings that share a common carbon atom. Examples of heterocycloalkenyl include but are not limited to tetrahydropyridyl and dihydropyranyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). Any ring atom can be substituted (e.g., by one or more substituents).

The term "heteroarylalkyl" or the term "heteroaralkyl" refers to an alkyl substituted with a heteroaryl.

The term "oxo" refers to an oxygen atom, which forms a carbonyl when attached to carbon, an N-oxide when attached to nitrogen, and a sulfoxide or sulfone when attached to sulfur.

The term "acyl" refers to an alkylcarbonyl, cycloalkylcarbonyl, arylcarbonyl, heterocyclylcarbonyl, or heteroarylcarbonyl substituent, any of which may be further substituted (e.g., by one or more substituents).

The term "substituents" refers to a group "substituted" on an alkyl, cycloalkyl, alkenyl, alkynyl, heterocyclyl, heterocycloalkenyl, cycloalkenyl, aryl, or heteroaryl group at any atom of that group. Any atom can be substituted. Suitable substituents include, without limitation, alkyl (e.g., C1, C2, C3, C4, C5, C6, C7, C8, C9, C10, C11, C12 straight or branched chain alkyl), cycloalkyl, haloalkyl (e.g., perfluoroalkyl such as $CF_3$), aryl, heteroaryl, aralkyl, heteroaralkyl, heterocyclyl, alkenyl, alkynyl, cycloalkenyl, heterocycloalkenyl, alkoxy, haloalkoxy (e.g., perfluoroalkoxy such as $OCF_3$), halo, hydroxy, carboxy, carboxylate, cyano, nitro, amino, alkyl amino, $SO_3H$, sulfate, phosphate, methylenedioxy (—O—$CH_2$—O— wherein oxygens are attached to vicinal atoms), ethylenedioxy, oxo, thioxo (e.g., C=S), imino (alkyl, aryl, aralkyl), $S(O)_n$alkyl (where n is 0-2), $S(O)_n$aryl (where n is 0-2), $S(O)_n$heteroaryl (where n is 0-2), $S(O)_n$heterocyclyl (where n is 0-2), amine (mono-, di-, alkyl, cycloalkyl, aralkyl, heteroaralkyl, aryl, heteroaryl, and combinations thereof), ester (alkyl, aralkyl, heteroaralkyl, aryl, heteroaryl), amide (mono-, di-, alkyl, aralkyl, heteroaralkyl, aryl, heteroaryl, and combinations thereof), sulfonamide (mono-, di-, alkyl, aralkyl, heteroaralkyl, and combinations thereof). In one aspect, the substituents on a group are independently any one single, or any subset of the aforementioned substituents. In another aspect, a substituent may itself be substituted with any one of the above substituents.

DETAILED DESCRIPTION

Compounds and Related Methods of Use

In mechanistically and synthetically guided efforts to identify simpler small-molecule H-bond donors for enantioselective imine hydrocyanation, we discovered that amido-thiourea derivatives lacking an diaminocyclohexane moiety, are efficient catalysts for the hydrocyanation of N-benzhydryl-protected imines, for example, using HCN generated in situ from TMSCN and methanol. Exemplary reaction schemes are provided herein.

Accordingly, described herein are novel compounds. The compounds can be useful, for example, to produce an α-amino acid or a precursor thereof such as an α-aminonitrile. The compounds can also be useful, for example, to produce a compound of formula (III). In particular, described herein are compounds of formula (I)

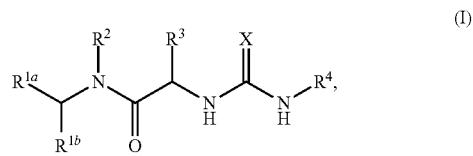

wherein X, $R^{1a}$, $R^{1b}$, $R^2$, $R^3$, and $R^4$ are as described herein. In some embodiments, the compound of formula (I) is enantiomerically enriched for a specific isoform, for example on of the compounds of formula (Ia) or (Ib) as provided below:

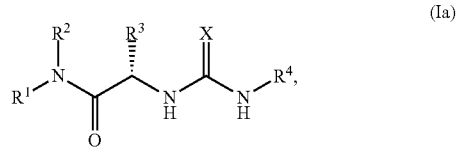

wherein the compound has an ee of at least about 50% (e.g., at least about 55%, 60%, 65%, 70%, 75%, 80%, 85%, 90%, 95%, 97%, 98%, or 99%) or

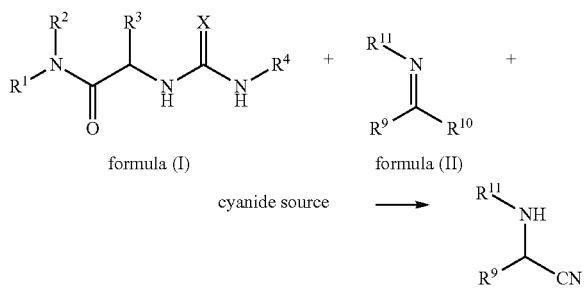
(Ib)

wherein the compound has an ee of at least about 50% (e.g., at least about 55%, 60%, 65%, 70%, 75%, 80%, 85%, 90%, 95%, 97%, 98%, or 99%).

A compound of formula (I) can be reacted with a substrate such as an imine of formula (II) and a source of cyanide to produce an α-aminonitrile. This compound can be further modified to provide an α-amino acid. An exemplary scheme is provided below:

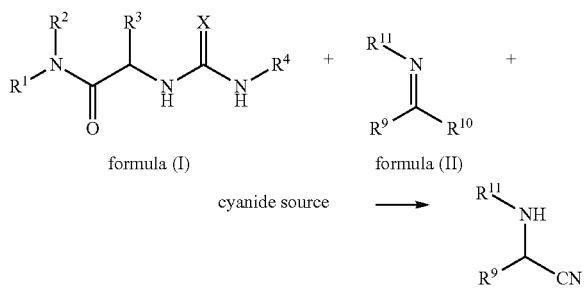

The resulting α-aminonitrile can be converted to an amino acid, for example, by hyrolyzing the cyano moiety. More specific examples of this reaction scheme, for example, with a plurality of compounds of formula (I), are provided in Table 1 below. In preferred embodiments, the reaction produces an α-aminonitrile having high enantiomeric excess, for example, an α-aminonitrile having an ee of at least about 50% (e.g., at least about 55%, 60%, 65%, 70%, 75%, 80%, 85%, 90%, 95%, 98%, or 99%). In some embodiments, the compound of formula (I) is a compound of formula (Ia) or (Ib) as provided above.

Table 1, as provided below, shows exemplary reaction schemes with a compound of formula (I) as described herein.

TABLE 1

Dependence of imine hydrocyanation enantioselectivity on catalyst structure

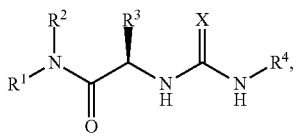 TMSCN (2 equiv), MeOH (2 equiv), 4 (5 mol %), toluene (0.2M), -30° C., 20 h → 3

| Entry | Catalyst | ee$^a$ (%) R = t-Bu | ee$^a$ (%) R = C$_6$H$_5$ |
|---|---|---|---|
| 1 | 4a | -14 | 41 |
| 2 | 4b | 30 | 86 |
| 3 | 4c | 58 | 90 |
| 4 | 4d | 77 | 97 |
| 5 | 4e | 93 | 98 |

$^a$Enantiomeric excess determined by chiral HPLC analysis.

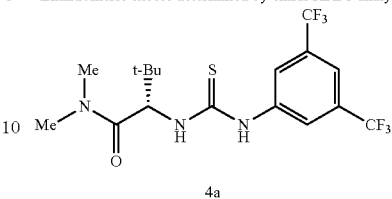
4a

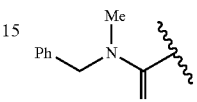
4b

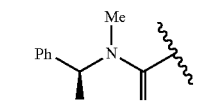
4c

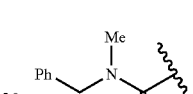
4d

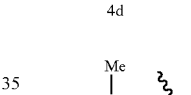
4e

Whereas simple amido-thiourea 4a induced low levels of enantioselectivity in hydrocyanation of both aliphatic and aromatic imines (entry 1), the corresponding phenyl-substituted amido-thioureas proved more effective (entries 2-4). Highest enantioselectivities were observed in reactions catalyzed by N-benzhydryl-substituted catalyst 4e (entry 5). This catalyst contains a single stereogenic center and is prepared in three steps from commercially available reagents (74% overall yield on 5-gram scale), and is thus readily accessible compared with chiral Strecker catalysts identified previously.

Amido-thiourea derivative 4e proved effective and highly enantioselective for the hydrocyanation of imines derived from alkyl (Table 2, entries 1-5), aryl (entries 7-16), heteroaryl (entries 17-19), and alkenyl aldehydes (entries 20-22). Lower enantioselectivities are obtained with less sterically demanding imines (entries 6 and 24). In general, (R)-α-aminonitriles are obtained from the catalyst derived from (S)-tert-leucine. This outcome introduces an important practical feature of this methodology, because (S)-tent-leucine is readily available inexpensively by enzymatic methods.

High yields and enantioselectivities are obtained in these imine hydrocyanations catalyzed by 4e; however, TMSCN is expensive, and the stoichiometric HCN generated upon combination with methanol introduces serious practical and safety liabilities that limit application on preparative scale. Potassium cyanide (KCN) and sodium cyanide (NaCN) represent practical, alternative cyanide sources for Strecker syntheses, but these reagents have found limited application in catalytic asymmetric imine hydrocyanations developed to date. This may be attributed to the poor solubility of cyanide salts in organic solvents, and the incompatibility of known catalysts to aqueous media. In contrast, catalyst 4e lacks any sensitive functional groups, and therefore might be adaptable to use under aqueous or biphasic conditions. Indeed, treatment of toluene solutions of imines 2a-w with KCN, acetic acid, water, and catalyst 4e led to the formation of α-aminonitriles with similar enantioselectivity as was observed in the homogeneous, TMSCN/MeOH-mediated reaction. Only small decreases in enantioselectivity were observed at higher temperatures and concentrations, and reactions carried out under these more practical conditions proceeded at substantially higher rates.

TABLE 2

Scope of asymmetric imine hydrocyanation

| Entry | Imine 2 (R =) | 4e (mol %) | Yield[a] (%) | ee[b] (%) |
|---|---|---|---|---|
| 1 | tert-butyl (a) | 2 | 99 | 93 |
| 2 | Et$_2$MeC (b) | 2 | 99 | 96 |
| 3 | PhMe$_2$C (c) | 2 | 97 | 85 |
| 4 | (1-methyl)cyclohexyl (d) | 2 | 99 | 95 |
| 5 | 1-adamantyl (e) | 2 | 99 | 93 |
| 6 | cyclohexyl (f) | 2 | 99 | 74 |
| 7 | p-OMeC$_6$H$_4$ (g) | 2 | 99 | 99 |
| 8 | p-MeC$_6$H$_4$ (h) | 2 | 98 | 98 |
| 9 | C$_6$H$_5$ (i) | 2 | 98 | 98 |
| 10 | p-ClC$_6$H$_4$ (j) | 2 | 97 | 98 |
| 11 | p-CF$_3$C$_6$H$_4$ (k) | 2 | 98[c] | 96 |
| 12 | p-CNC$_6$H$_4$ (l) | 10 | 96[c] | 93 |
| 13 | p-BrC$_6$H$_4$ (m) | 2 | 98 | 99 |
| 14 | o-OMeC$_6$H$_4$ (n) | 2 | 97 | 88 |
| 15 | o-BrC$_6$H$_4$ (o) | 2 | 96[c] | 97 |
| 16 | m-BrC$_6$H$_4$ (p) | 2 | 97[c] | 92 |
| 17 | 2-furyl (q) | 2 | 99 | 93 |
| 18 | 3-furyl (r) | 2 | 98 | 97 |
| 19 | 2-thiophenyl (s) | 2 | 97[c] | 95 |
| 20 | 1-cyclohexenyl (t) | 2 | 99 | 95 |
| 21 | (E)-1-methyl-pent-1-enyl (u) | 2 | 98 | 91 |
| 22 | (E)-cinnamyl (v) | 2 | 99 | 95 |
| 23 | (E)-hexenyl (w) | 2 | 97 | 73 |

[a]Isolated yields of 3 after silica gel chromatography of reactions run on 1.0 mmol scale.
[b]Enantiomeric excess of purified samples determined by chiral HPLC analysis using commercially available columns.
[c]Reaction run at 0° C.

The efficiency of this reaction is relatively insensitive to small changes in reagent and catalyst concentration: using an optimized protocol, hydrocyanation experiments using 0.5 mol % catalyst were executed reproducibly and safely on 25-100 mmol scale of aliphatic imines 2a, 2b, and 2d (Table 2). These imines were prepared on multi-gram scales in one or two steps from commercially available aldehydes. The hydrocyanation reaction mixtures were treated with aqueous K$_2$CO$_3$ prior to workup to quench any unreacted HCN generated under the reaction conditions. The enantiomerically enriched α-aminonitriles were isolated in crude form by routine extraction and solvent removal procedures, and converted to the corresponding Boc-protected (R)-α-amino acids by a two-step sequence involving H$_2$SO$_4$/HCl-mediated hydrolysis followed by treatment of the resulting aqueous amino acid solutions with Boc$_2$O. The highly enantiomerically enriched, sterically demanding protected α-amino acids were then isolated on multi-gram scales by recrystallization. In each case, the synthetic sequence required no chromatographic purification or specialized equipment. The α-amino acids prepared by this method have found use as components of chiral catalysts or of medicinal chemistry targets, and are difficult to obtain via other catalytic methods.

A detailed experimental and computational analysis of the hydrocyanation reaction catalyzed by 4e points to a mechanism involving initial amido-thiourea induced imine protonation by HCN to generate a catalyst-bound iminium/cyanide ion pair. Collapse of this ion pair and C—C bond formation to form the α-aminonitrile then occurs in a post-rate-limiting step.

In some embodiments, a compound of formula (I) can also be used to produce a compound of formula (III) in the presence of the appropriate substrates (e.g., a compound of formula (IV) and a aldehyde of formula (V)). An exemplary scheme is provided below:

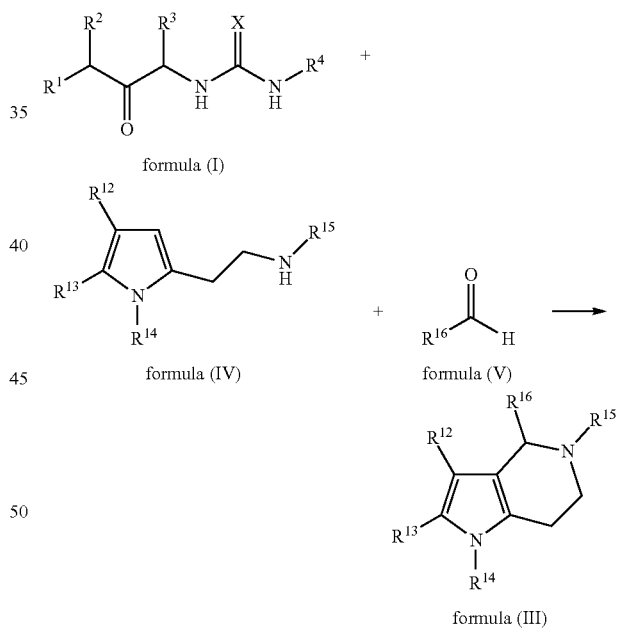

More specific examples of this reaction scheme, for example, with a number of compounds of formula (III) are provided in Table 3 below. In preferred embodiments, the reaction produces a compound of formula (III) having high enantiomeric excess, for example, an α-aminonitrile having an ee of at least about 50% (e.g., at least about 55%, 60%, 65%, 70%, 75%, 80%, 85%, 90%, 95%, 98%, or 99%).

Table 3, as provided below, shows exemplary reaction schemes to produce a compound of formula (III) utilizing a compound of formula (I) as described herein.

TABLE 3

Scope of Cyclization

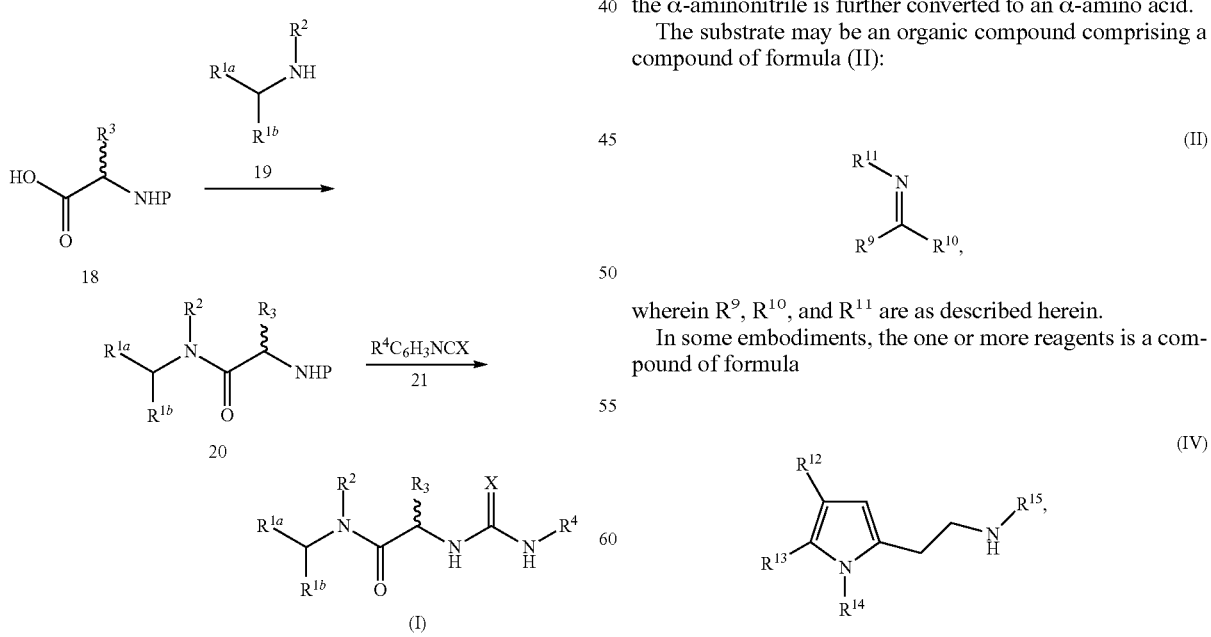

| Entry | R[16] = | X = | Yield[a] (%) | ee[b] (%) |
|---|---|---|---|---|
| 1 | iso-propyl | H | 99 | 93 |
| 2 | tert-butyl | H | 99 | 96 |
| 3 | 4-chlorophenyl | H | 97 | 85 |
| 4 | 4-cyanophenyl | 2-F | 99 | 95 |
| 5 | 2-bromophenyl | H | 99 | 93 |
| 6 | Iso-propyl | 3-F | 99 | 74 |

Methods of Making Compounds of Formula (I)

The compounds of formula (I) described herein can be made using a variety of synthetic techniques.

Scheme 1.

Scheme 1 above is an exemplary synthetic sequence that depicts a representative synthesis of compounds of formula (I) described herein. Carboxylic acid 18 is reacted with amine 19 under coupling conditions, for example, using a coupling agent in the presence of a base (e.g., a tertiary amine base), for example, using couplings agent HBTU in the presence of DIPEA base, to provide moiety 20. Removal of the amine protecting group (e.g., a Boc group) and subsequent reaction with 21 proceeds under standard conditions to provide target molecule (I). All variables depicted in scheme 1 above are as described herein.

As can be appreciated by the skilled artisan, methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The compounds of this invention may be modified by appending appropriate functionalities to enhance catalytic selectivity properties, e.g., to provide the desired stereochemical selectivity in the reaction methods described herein. Such modifications are known in the art.

Compositions and Reaction Mixtures

Described herein are compositions comprising a compound of formula (I), including a reaction mixture, e.g., a reaction mixture that is present during a method or process described herein. As defined generally herein, in certain embodiments, the process comprises mixing a substrate such as a compound of formula (II), a cyanide source and a compound of formula (I) described herein, under conditions sufficient to produce an α-aminonitrile. In some embodiments, the α-aminonitrile is further converted to an α-amino acid.

The substrate may be an organic compound comprising a compound of formula (II):

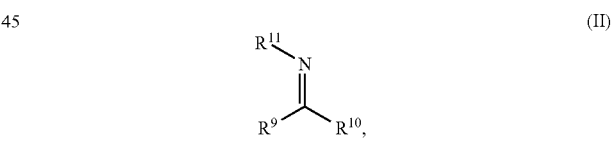

wherein $R^9$, $R^{10}$, and $R^{11}$ are as described herein.

In some embodiments, the one or more reagents is a compound of formula

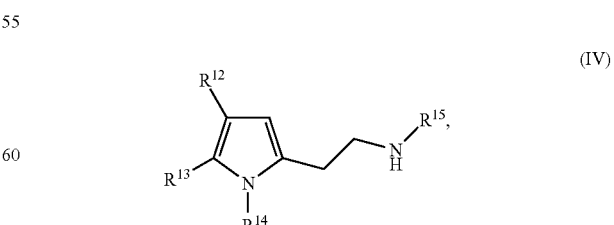

wherein $R^1$, $R^2$, $R^4$ and $R^5$ are as described herein.

In some embodiments, the one or more reagents is an aldehyde of formula (V):

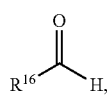

(V)

wherein R³ is as described herein.

In some embodiments, the compound of formula (I) is present in the composition (e.g., a reaction mixture) in a catalytic amount. For example, in a reaction mixture, the compound of formula (I) is present at less than 50 mol % relative to the substrate (e.g., a compound of formula (II), (IV) or (V)). In some embodiments, the compound of formula (I) is present at less than 45 mol %, less than 40 mol %, less than 35 mol %, less than 30 mol %, less than 25 mol %, less than 20 mol %, less than 15 mol %, less than 10 mol %, less than 5 mol %, less than 3 mol %, or less than 1 mol %.

In certain embodiments, the method further comprises a solvent. In certain embodiments, the solvent is an organic solvent. In certain embodiments, the solvent is an aprotic solvent. Exemplary organic solvents include, but are not limited to, benzene, toluene, xylenes, methanol, ethanol, isopropanol, acetonitrile, acetone, ethyl acetate, ethyl ether, tetrahydrofuran, methylene chloride, dichloroethane and chloroform, or a mixture thereof. In certain embodiments, the solvent is acetonitrile. In certain embodiments, the solvent is methylene chloride. In certain embodiments, the solvent is tetrahydrofuran. In certain embodiments, the solvent is dichloroethane. In certain embodiments, the solvent is benzene.

In certain embodiments, the reaction is a reaction below room temperature (e.g., a cooled reaction such as a reaction at a temperature of 0° C. or lower). In certain embodiments, the reaction is a heated reaction (e.g., a reaction occurring above room temperature). In certain embodiments, the reaction occurs under an inert atmosphere (e.g, an atmosphere of an inert gas such as nitrogen or argon). In certain embodiments, the reaction takes place under anhydrous conditions (e.g., conditions that are substantially free of water).

Described herein are compositions comprising a compound described herein, e.g., a compound of formula (I) or an α-aminonitrile or α-amino acid. In some embodiments, the compound of formula (I) is in a composition comprising a solvent (e.g., as a mixture such as a solution or a heterogeneous mixture). The composition can be free of compounds that would react with or degrade a compound of formula (I), e.g., the composition can be substantially free of water and/or substantially free of any reactive gases Reaction Products Reaction products provided herein include enantiomerically enriched compounds (e.g., amino acids or compounds of formula (III)). The reaction products provided by the methods described herein may be natural or unnatural amino acids. The methods described herein are also efficient at providing the unnatural amino acid enantiomers (e.g., the D-amino acids). These enantiomers are not easily isolable from natural sources or easily prepared by convention synthetic methods.

Amino acids are versatile compounds and can play a number of important central scientific roles ranging from building blocks (e.g., chiral building blocks) for the synthesis of larger, complex compounds and natural products. Exemplary compounds include peptides, proteins, proteasomes and nitrogen containing natural products. In addition, the 20 naturally occurring amino acids produce biological proteins which convey a vast array of biochemical uses and applications. Amino acids also serve a number of important industrial applications including uses as drugs and cosmetics to supplements in animal feed and as biodegradable polymers. Compounds of formula (III) may also serve as a common motif in biologically active small molecules.

Kits

A compound described herein (e.g., a catalyst) may be provided in a kit. The kit includes (a) a compound used in a method described herein (e.g., a compound of formula (I) and/or formula (II) and/or formula (IV) and/or formula (V), and, optionally (b) informational material. The informational material can be descriptive, instructional, marketing or other material that relates to the methods described herein and/or the use of the compounds for the methods described herein.

The informational material of the kits is not limited in its form. In one embodiment, the informational material can include information about production of the compound, molecular weight of the compound, concentration, date of expiration, batch or production site information, and so forth. In one embodiment, the informational material relates to methods for administering the compound.

In one embodiment, the informational material can include instructions to use a compound described herein in a suitable manner to perform the methods described herein, e.g., carry out a reaction to produce a compound described herein.

The informational material of the kits is not limited in its form. In many cases, the informational material, e.g., instructions, is provided in printed matter, e.g., a printed text, drawing, and/or photograph, e.g., a label or printed sheet.

In addition to a compound described herein, the composition of the kit can include other ingredients, such as a solvent or buffer, a stabilizer, a preservative. Alternatively, the other ingredients can be included in the kit, but in different compositions or containers than a compound described herein. In such embodiments, the kit can include instructions for reacting a compound described herein with a reagent.

In some embodiments, the components of the kit are stored under inert conditions (e.g., under Nitrogen or another inert gas such as Argon). In some embodiments, the components of the kit are stored under anhydrous conditions (e.g., with a desiccant). In some embodiments, the components are stored in a light blocking container such as an amber vial.

A compound described herein can be provided in any form, e.g., liquid, dried or lyophilized form. It is also possible for the compound described here to be adsorbed onto a solid support system (e.g., a polymeric bead system).

The kit can include one or more containers for the composition containing a compound described herein. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers. The containers of the kits can be air tight, waterproof (e.g., impermeable to changes in moisture or evaporation), and/or light-tight.

EXAMPLES

General Experimental Procedures.

Reactions were carried out in oven-dried round-bottomed flasks, unless otherwise noted. The flasks were fitted with rubber septa and reactions were conducted under a positive pressure of nitrogen. Stainless steel syringes or cannulae were used to transfer air- and moisture-sensitive liquids. Flash chromatography was performed using silica gel 60 (230-400 mesh) from EM Science.

Materials.

Commercial reagents were purchased from Sigma Aldrich, Alfa Aesar, or Lancaster, and used as received with the following exceptions: dichloromethane and toluene were dried by passing through columns of activated alumina. Diisopropylethylamine and triethylamine were distilled from $CaH_2$ at 760 torr. TMSCN was distilled at 760 Torr and stored in a Schlenk flask at 0° C.

Instrumentation.

Proton nuclear magnetic resonance ($^1$H NMR) spectra and carbon nuclear magnetic resonance ($^{13}$C NMR) spectra were recorded on Varian-Mercury-400 (400 MHz) or Inova-500 (500 MHz) spectrometers. Chemical shifts for protons are reported in parts per million downfield from tetramethylsilane and are referenced to residual protium in the NMR solvent ($CHCl_3$: δ 7.26) Chemical shifts for carbon are reported in parts per million downfield from tetramethylsilane and are referenced to the carbon resonances of the solvent ($CDCl_3$: δ 77.16). Data are represented as follows: chemical shift, integration, multiplicity (br=broad, s=singlet, d=doublet, t=triplet, q=quartet, m=multiplet), coupling constants in Hertz (Hz). Infrared (IR) spectra were obtained using a Mattson Galaxy Series FTIR 3000 spectrophotometer referenced to a polystyrene standard. Data are represented as follows: frequency of absorption ($cm^{-1}$), intensity of absorption (s=strong, m=medium, w=weak, br=broad). Optical rotations were measured using a 2-mL cell with a 10-cm path length on a Jasco DIP 370 digital polarimeter. The mass spectral data were obtained at the Harvard University mass spectrometry facility. Chiral HPLC analysis was performed using a Shimadzu VP-series instrument.

Example 1

Preparation of Formula (I) Compounds

Scheme 2:

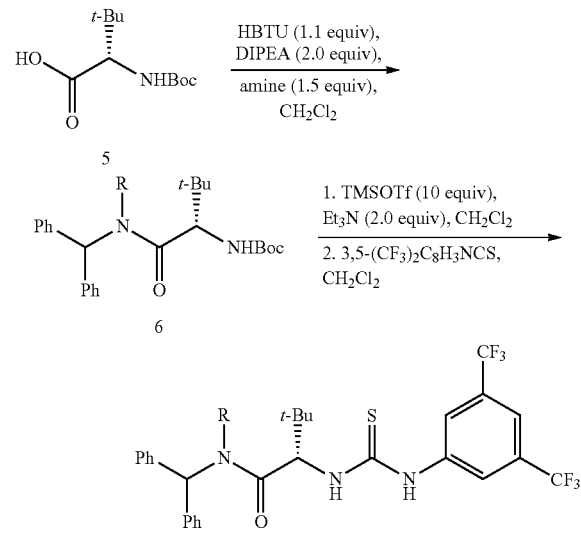

(S)-tert-butyl 1-(benzhydryl(methyl)amino)-3,3-dimethyl-1-oxobutan-2-ylcarbamate

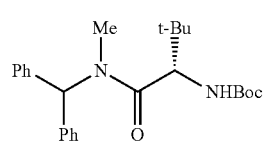

An oven-dried 50-mL round-bottomed flask was charged with Boc-L-tert-leucine (5) (2.78 g, 12.0 mmol, 1.0 equiv), HBTU (5.01 g, 13.2 mmol, 1.1 equiv), and N-(diphenylmethyl)methylamine (3.55 g, 18 mmol, 1.5 equiv). Anhydrous $CH_2Cl_2$ (24 mL) and N,N-diisopropylethylamine (4.18 mL, 24 mmol, 2.0 equiv) were added sequentially via syringe. The flask was capped with a plastic stopper, and the reaction mixture was stirred for 3 days at room temperature. The resulting orange mixture was diluted with $Et_2O$ (100 mL), washed with 1N HCl (2×100 mL), sat. $NaHCO_3$ (100 mL), and brine (100 mL). The organic phase was dried over $Na_2SO_4$ and concentrated under reduced pressure to provide a viscous orange oil. The product was subjected to purification by flash column chromatography on silica gel (gradient elution, 19:1→1:1 hexanes/$Et_2O$, 100 g silica gel, 1.2 L solvent) to provide the product (6a) as a white foam (4.51 g, 11.0 mmol, 91% yield). $[α]_D^{25}$=−28.2° (c 1.76, $CHCl_3$). The compound exists as a 5:1 mixture of amide rotamers in $CDCl_3$. 1H NMR (500 MHz, $CDCl_3$), major rotamer: δ 7.38-7.14 (11H, m), 5.28 (1H, d, J=10.0 Hz), 4.57 (1H, d, J=10.0 Hz), 2.97 (3H, s), 1.46, (9H, s), 1.03 (9H, s); minor rotamer: δ 7.38-7.14 (10H, m), 6.77 (1H, s), 5.28 (1H, d, J=10.0 Hz), 4.72 (1H, d, J=10.0 Hz), 2.73, (3H, s), 1.44 (9H, s), 0.93 (9H, s). $^{13}$C {$^1$H} NMR (126 MHz, $CDCl_3$), major rotamer: δ 173.0, 156.2, 139.3, 138.4, 129.4, 128.5, 128.4, 127.9, 127.6, 127.1, 79.6, 60.8, 56.7, 35.2, 33.2, 28.3, 26.5; minor rotamer: δ 173.5, 155.5, 139.4, 138.8, 129.0, 128.5, 128.4, 128.3, 127.7, 127.6, 79.5, 64.6, 56.1, 35.3, 31.3, 28.3, 26.5. IR ($cm^{-1}$): 3436 (w), 3326 (w), 3062 (w), 3029 (w), 2965 (m), 2871 (w), 1953 (w), 1893 (w), 1810 (w), 1712 (s), 1640 (s), 1496 (s), 1454 (m), 1404 (m), 1366 (m), 1320 (w), 1245 (m), 1172 (s), 1105 (w), 1058 (w), 1005 (w), 974 (w), 922 (w), 870 (w), 734 (w), 702 (m), 608 (w). LRMS (ESI): 433.25 (100%) [M+Na]$^+$.

(S)-2-amino-N-benzhydryl-N,3,3-trimethylbutanamide

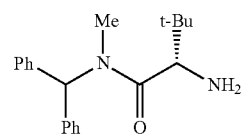

A 200-mL round-bottomed flask containing (R)-tert-butyl 1-(benzhydryl(methyl)amino)-3,3-dimethyl-1-oxobutan-2-ylcarbamate (6a) (4.51 g, 11.0 mmol, 1 equiv) and a stir bar was purged with $N_2$ Anhydrous $CH_2Cl_2$ (55 mL) and triethylamine (3.07 mL, 22.0 mmol, 2 equiv) were added sequentially via syringe. The reaction was cooled to 0° C. in an ice bath, and trimethylsilyl trifluoromethansulfonate (18.8 mL, 110 mmol, 10 equiv) was added dropwise via syringe over 5 min with stirring. The solution was stirred for 1 h at 0° C. The slightly yellow homogeneous reaction mixture was treated with 100 mL of ice cold saturated aqueous $NaHCO_3$ in 10-mL portions over 5 min at 0° C. The mixture was transferred to a 500-mL reparatory funnel, and diluted with saturated aqueous NaHCO$_3$ (100 mL) and CH$_2$Cl$_2$ (50 mL). The layers were thoroughly mixed with venting, and the organic layer was removed. The aqueous layer was extracted with CH$_2$Cl$_2$ (50 mL). The combined organic layers were dried over Na$_2$SO$_4$, decanted into a 500-mL round-bottomed flask, and concentrated in vacuo to provide a viscous yellow residue. The residue was partitioned between CH$_2$Cl$_2$ (50 mL) and saturated NaHCO$_3$ (50 mL). The aqueous layer was extracted with CH$_2$Cl$_2$ (30 mL). The organic layers were dried over Na$_2$SO$_4$ and filtered through a 2-cm height pad of silica gel on a 5-cm diameter fritted disk funnel, rinsing with CH$_2$Cl$_2$ (30 mL). The receiving flask was switched, and the silica gel pad was further eluted with 1:1:0.04 CH$_2$Cl$_2$/Et$_2$O/MeOH (200 mL) to provide 6b as a yellow oil in >95% $^1$H-NMR purity (2.98 g, 9.60 mmol, 87% yield). The product was used in the next step without further purification. Spectroscopically pure product may be isolated by subjecting the crude product to flash column chromatography on silica gel (gradient elution, 3:1 CH$_2$Cl$_2$/Et$_2$O→1:1:0.05 CH$_2$Cl$_2$/Et$_2$O/MeOH). The compound exists as a 3.5:1 mixture of amide rotamers in CDCl$_3$. $^1$H NMR (500 MHz, CDCl$_3$), major rotamer: δ 7.14-7.34 (11H, m), 3.59 (1H, s), 2.88 (3H, s), 1.54 (2H, br s), 1.02 (9H, s); minor rotamer: δ 7.34-7.14 (10H, m), 6.53 (1H, s), 3.47 (1H, s), 2.72 (3H, s), 1.54 (2H, br s), 1.03 (9H, s). $^{13}$C {$^1$H} NMR (125 MHz, CDCl$_3$), major rotamer: δ 175.4, 139.2, 138.8, 129.1, 128.44, 128.40, 128.3, 127.4, 127.2, 60.4, 58.4, 35.6, 32.9, 26.4; minor rotamer: δ 176.5, 139.6, 139.0, 128.9, 128.8, 128.5, 127.9, 127.82, 127.79, 64.5, 58.5, 34.9, 31.3, 26.6. IR (cm$^{-1}$): 3381 (w), 3307 (w), 3061 (m), 3029 (m), 2955 (s), 2867 (m), 1955 (w), 1892 (w), 1813 (w), 1768 (w), 1639 (s), 1495 (s), 1479 (m), 1447 (m), 1409 (m), 1364 (m), 1282 (m), 1104 (m), 1079 (m), 1031 (m), 970 (m), 922 (m), 870 (m), 827 (m), 762 (m), 735 (m), 701 (s). LRMS (ESI): 311.2126 (100%), [C$_{20}$H$_{26}$N$_2$O+H]$^+$.

(S)—N-benzhydryl-2-(3-(3,5-bis(trifluoromethyl)phenyl)thioureido)-N,3,3-trimethylbutanamide (4e)

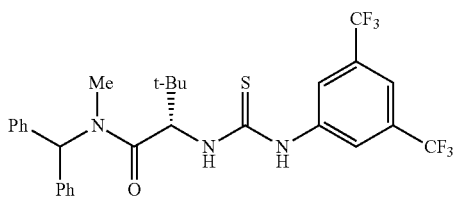

4e

A 100-mL round-bottomed flask containing (S)-2-amino-N-benzhydryl-N,3,3-trimethylbutanamide (6b) (2.98 g, 9.60 mmol, 1.0 equiv) was charged with anhydrous CH$_2$Cl$_2$ (30 mL). 3,5-Bis(trifluoromethyl)phenylisothiocyanate (1.75 mL, 9.60 mmol, 1.0 equiv) was added in one portion via syringe. The flask was capped with a plastic stopper, and the reaction mixture was stirred for 2 h at room temperature. The clear, yellow solution was concentrated using a rotary evaporator. The residue was subjected to purification by flash column chromatography on silica gel (gradient elution, hexanes→1:1 hexanes/Et$_2$O, 100 g silica gel, 1.5 L solvent). The product (4e) was isolated as a white solid in ~98% $^1$H-NMR purity (5.14 g, 8.83 mmol, 92% yield; 74% yield over three steps). The compound exists as a 15:1 mixture of amide rotamers in CDCl$_3$. [α]=−83.4° (c 1.0, CHCl$_3$). $^1$H NMR (500 MHz, CDCl$_3$), major rotamer: δ 8.26 (1H, br s), 8.92 (1H, br s), 7.69 (2H, s), 7.59 (1H, s), 7.31-7.37 (3H, m), 7.13-7.16 (2H, m), 6.95-7.06 (5H, m), 5.65 (1H, d, J=9 Hz), 3.13 (3H, s), 1.13 (9H, s); selected minor rotamer resonances: δ 2.76 (3H, s), 0.92 (9H, s). $^{13}$C {$^1$H} NMR, major rotamer: δ 182.5, 174.2, 139.7, 139.0, 137.3, 131.9 (q, J$_{C-F}$=34 Hz), 129.8, 128.8, 128.7, 128.4, 128.2, 127.5, 127.2, 126.3 (m), 123.1 (q, J$_{C-F}$=274 Hz), 119.3 (m), 62.4, 62.3, 36.5, 34.0, 27.6. IR (cm$^{-1}$): 3313 (br m), 2967 (m), 1609 (m), 1529 (m), 1473 (m), 1380 (m), 1276 (s), 1172 (m), 1127 (s), 961 (m), 889 (w), 847 (w), 758 (w), 698 (m), 681 (m). LRMS (ESI): 582.2 (80%) [M+H].

(S)-2-(3-(3,5-bis(trifluoromethyl)phenyl)thioureido)-N,N,3,3-tetramethylbutanamide (4a)

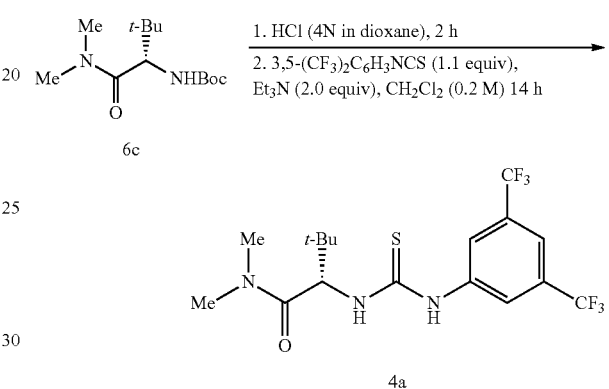

A 50-mL round-bottomed flask was charged with (S)-tert-butyl 1-(dimethylamino)-3,3-dimethyl-1-oxobutan-2-ylcarbamate (6c) (860 mg, 2.0 mmol, 1.0 equiv) and 4N HCl in dioxane (5.0 mL). The reaction mixture was stirred at room temperature for 2 h, then concentrated under reduced pressure and maintained at ~1 torr for 1 h. The resulting white, foamy solid was dissolved in CH$_2$Cl$_2$ (10 mL). Et$_3$N (562 µL, 4.0 mmol, 2.0 equiv) and 3,5-bis(trifluoromethyl)phenylisothiocyanate (596 mg, 2.2 mmol, 1.1 equiv) were added sequentially via syringe. The flask was capped with a plastic stopper, and the reaction mixture was stirred at room temperature for 14 h. The reaction mixture was concentrated under reduced pressure, and the residue was subjected to purification by flash column chromatography on silica gel (gradient elution, 3:1 hexanes/Et$_2$O→1:1 hexanes/Et$_2$O) to provide the product (4a) as a white solid (613 mg, 1.43 mmol, 71% yield over two steps). [α]$_D^{25}$=−32.8° (c 1.0, CHCl$_3$). $^1$H NMR (500 MHz, CDCl$_3$): δ 9.06 (1H, s), 7.90 (2H, s), 7.77 (1H, d, J=9 Hz), 7.56 (1H, s), 5.68 (1H, d, J=9 Hz), 3.35 (3H, s), 2.97 (3H, s), 1.12 (9H, s). $^{13}$C {$^1$H}NMR (100 MHz, CDCl$_3$): δ 181.8, 174.0, 140.3, 131.7 (q, J$_{C-F}$=33 Hz), 123.7 (m), 123.3 (q, J$_{C-F}$=272 Hz), 118.1 (m), 60.9, 39.1, 36.2, 36.0, 27.2. IR (cm$^{-1}$): 3322 (br m), 2972 (m), 1611 (m), 1532 (s), 1474 (m), 1385 (m), 1274 (s), 1174 (m), 1126 (m), 963 (m), 883 (m), 848 (w), 700 (m), 680 (m). LRMS (ESI): 452.1 (60%) [M+Na]$^+$.

Preparation of Compounds of Formula (II)

Method A:

A 250-mL round-bottomed flask was charged with dichloromethane (80 mL), anhydrous Na$_2$SO$_4$ (30 g), aminodiphenylmethane (12 mmol), and aldehyde (12 mmol). The mixture was stirred at room temperature until the aldehyde had been fully consumed, as determined by $^1$H NMR analysis of an aliquot removed from the reaction mixture (1-12 h). The mixture was filtered through a fitted disk funnel, rinsing with dichloromethane (3×10 mL). A 3" plug of silica gel was rinsed with 9:1:0.1 hexanes/diethyl ether/triethylamine (100 mL). The reaction mixture was concentrated under reduced pressure, and the crude residue was filtered through the silica gel plug with 9:1 hexanes/diethyl ether as the eluent. The filtrate was concentrated under reduced pressure to provide the imine product (>90% yield). The imine was used in the next step without further purification.

Method B:

A 100-mL round-bottomed flask was charged with toluene (40 mL), aminodiphenylmethane (12 mmol), and aldehyde (12 mmol). A Dean-Stark trap was attached to the flask, and the mixture was stirred at reflux under $N_2$ in an oil bath until the aldehyde was fully consumed, as determined by $^1$H NMR analysis of an aliquot removed from the reaction mixture. A 3" plug of silica gel was rinsed with 9:1:0.1 hexanes/diethyl ether/triethylamine (100 mL). The reaction mixture was concentrated under reduced pressure, and the crude residue was filtered through a the silica gel plug with 9:1 hexanes/diethyl ether as the eluent. The filtrate was concentrated under reduced pressure to provide the imine product (>90% yield). The imine was used in the next step without further purification.

(E)-N-(2,2-dimethylpropylidene)diphenylmethanamine (2a)

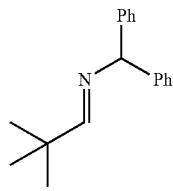

Prepared via Method A. Spectroscopic data match previously reported data reported in Krueger et al. (See *J. Am. Chem. Soc.* 121:4284 (1999)).

(E)-N-(2-ethyl-2-methylbutylidene)diphenylmethanamine (2b)

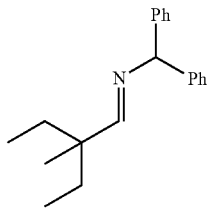 [SMILES: CCC(C)(/C=N/C(c1ccccc1)c1ccccc1)CC]

Prepared via Method A. $^1$H NMR (500 MHz, CDCl$_3$): δ 7.70 (1H, s), 7.43 (4H, d, J=7.5 Hz), 7.38 (4H, t, J=7.8 Hz), 7.29 (2H, t, J=7.3 Hz), 5.47 (1H, s), 1.52-1.65 (4H, m), 1.16 (3H, s), 0.87 (6H, t, J=7.8 Hz). $^{13}$C {$^1$H} NMR (125 MHz, CDCl$_3$): δ 171.2, 144.3, 128.2, 127.5, 126.6, 77.8, 42.5, 30.6, 20.6, 8.4. IR (cm$^{-1}$): 3061 (w), 3026 (w), 2925 (m, br), 2850 (m, br), 1661 (m), 1493 (m), 1449 (m), 1026 (m), 756 (m), 696 (s). LRMS (ESI): 292.2 (100%) [M+H]$^+$.

(E)-N-(2-methyl-2-phenylpropylidene)diphenylmethanamine (2c)

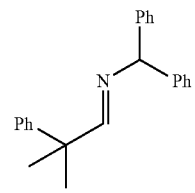

Prepared via Method B. $^1$H NMR (500 MHz, CDCl$_3$): δ 7.90 (1H, s), 7.44 (4H, d, J=8.0 Hz), 7.27-7.40 (11H, m), 5.49 (1H, s), 1.60 (6H, s). $^{13}$C {$^1$H} NMR (125 MHz, CDCl$_3$): δ 169.4, 145.9, 144.1, 128.4, 128.3, 127.5, 126.8, 126.4, 126.3, 77.3, 44.0, 26.1. IR (cm$^{-1}$): 3060 (w), 3026 (w), 2969 (w), 2836 (w), 1660 (m), 1599 (w), 1493 (m), 1448 (m), 1387 (w), 1364 (w), 1028 (m), 762 (m), 696 (s). LRMS (ESI): 314.2 (100%) [M+H]$^+$.

(E)-N-((1-methylcyclohexyl)methylene)diphenylmethanamine (2d)

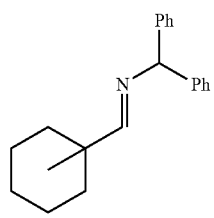

Prepared via Method B. $^1$H NMR (500 MHz, CDCl$_3$): δ 7.74 (1H, s), 7.43 (4H, d, J=6.5 Hz), 7.38 (4H, t, J=7.5 Hz), 7.29 (2H, t, J=7.3 Hz), 5.44 (1H, s), 1.89-1.93 (2H, m), 1.49-1.62 (5H, m), 1.38-1.43 (3H, m), 1.13 (3H, s). $^{13}$C {$^1$H} NMR (125 MHz, CDCl$_3$): δ 171.6, 144.3, 128.3, 128.1, 127.6, 127.5, 126.7, 77.8, 39.6, 35.6, 26.0, 25.5, 22.5. IR (cm$^{-1}$): 3062 (w), 3026 (w), 2965 (m, br), 2935 (m), 1661 (m), 1599 (w), 1492 (m), 1452 (m), 1382 (m), 1030 (m), 745 (m), 696 (s). LRMS (ESI): 280.2 (100%) [M+H]$^+$.

(E)-N-(1-adamantyl)diphenylmethanamine (2e)

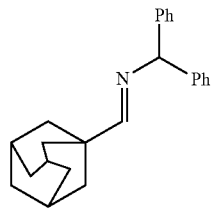 [SMILES: C(=N\C(c1ccccc1)c1ccccc1)/C12CC3CC(CC(C3)C1)C2]

Prepared via Method A. $^1$H NMR (500 MHz, CDCl$_3$): δ 7.56 (1H, s), 7.31-7.35 (8H, m), 7.22-7.27 (2H, m), 5.34 (1H, s), 2.06 (3H, s), 1.72-1.79 (12H, m). $^{13}$C {$^1$H} NMR (125 MHz, CDCl$_3$): δ 171.6, 144.3, 128.3, 127.5, 126.7, 77.5, 39.5, 38.4, 36.8, 28.1. IR (cm$^{-1}$): 3024 (w), 2905 (m, br), 2849 (m), 2798 (m), 1661 (m), 1492 (m), 1449 (m), 1053 (m), 750 (m), 699 (s). LRMS (ESI): 330.2 (100%) [M+H]$^+$.

(E)-N-(cyclohexylmethylene)diphenylmethanamine
(2f)

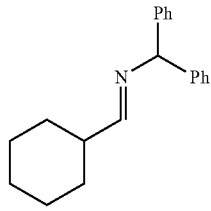 [SMILES: C(=N\C(c1ccccc1)c1ccccc1)/C1CCCCC1]

Prepared via Method A. $^1$H NMR (500 MHz, CDCl$_3$): δ 7.65 (1H, d, J=5.0 Hz), 7.23-7.26 (8H, m), 7.15-7.18 (2H, m), 5.27 (1H, s), 2.24-2.27 (1H, m), 1.80-1.83 (2H, m), 1.70-1.72 (2H, m), 1.61-1.64 (1H, m), 1.15-1.29 (5H, m). $^{13}$C {$^1$H} NMR (125 MHz, CDCl$_3$): δ 169.1, 144.0, 128.3, 127.6, 126.8, 77.9, 43.5, 29.7, 26.0, 25.4. IR (cm$^{-1}$) 3060 (w), 3026 (w), 2932 (m), 2852 (m), 1664 (m), 1493 (m), 1448 (m), 1376 (w), 1276 (w), 1016 (w), 890 (w), 759 (m), 745 (s), 697 (s). LRMS (ESI): 278.2 (50%) [M+H]$^+$.

(E)-N-(4-methoxybenzylidene)diphenylmethanamine
(2g)

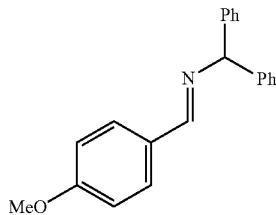 [SMILES: COc1ccc(/C=N/C(c2ccccc2)c2ccccc2)cc1]

Prepared via Method A. Spectroscopic data match previously reported data from Augeri et al. (See *J. Med. Chem.* 48:5025, (2005)).

(E)-N-(4-methylbenzylidene)diphenylmethanamine
(2h)

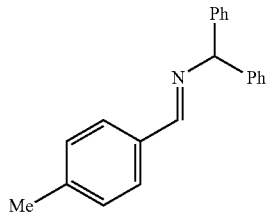

Prepared via Method A. $^1$H NMR (500 MHz, CDCl$_3$): δ 8.47 (1H, s), 7.82 (2H, d, J=8.0 Hz), 7.50 (4H, m), 7.40 (4H, m), 7.31 (4H, m), 5.67 (1H, s), 2.46 (3H, s). $^{13}$C {$^1$H} NMR (125 MHz, CDCl$_3$): δ 160.6, 144.0, 141.0, 133.7, 129.2, 128.4, 128.4, 127.7, 126.9, 77.8, 21.5. IR (cm$^{-1}$): 3081 (w), 3026 (w), 2919 (w), 2851 (w), 1663 (m), 1491 (m), 1274 (m), 1027 (m), 817 (m), 756 (m), 733 (m), 697 (s). LRMS (ESI): 286.2 (100%) [M+H]$^+$.

(E)-N-benzylidenediphenylmethanamine (2i)

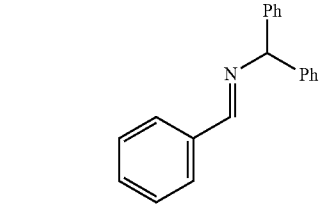 [SMILES: C(=N\C(c1ccccc1)c1ccccc1)/c1ccccc1]

Prepared via Method A. Spectroscopic data match previously reported data in Krueger et al. (See *J. Am. Chem. Soc.* 121:4284 (1999)).

(E)-N-(4-chlorobenzylidene)diphenylmethanamine
(2j)

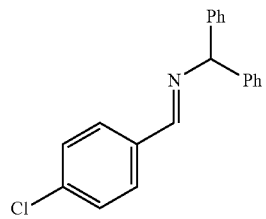

Prepared via Method A. Spectroscopic data match previously reported data in Lautens et al. (See *Org. Lett.,* 6:345 (2004)).

(E)-diphenyl-N-(4-(trifluoromethyl)benzylidene)
methanamine (2k)

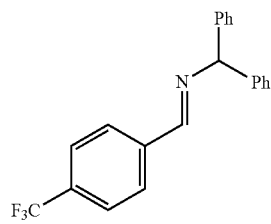

Prepared via Method A. $^1$H NMR (500 MHz, CDCl$_3$): δ 8.50 (1H, s), 7.99 (2H, d, J=8.0 Hz), 7.71 (2H, d, J=8.0 Hz), 7.45 (4H, d, J=8.0 Hz), 7.38 (4H, t, J=7.8 Hz), 7.29 (2H, t, J=7.5 Hz), 5.69 (1H, s). $^{13}$C {$^1$H} NMR (125 MHz, CDCl$_3$): δ 159.3, 143.5, 139.4, 132.3 (q, J$_{C-F}$=32.2 Hz), 128.6, 128.5, 127.6, 127.2, 125.5 (q, J$_{C-F}$=3.6 Hz), 123.9 (q, J$_{C-F}$=271.3 Hz), 78.0. IR (cm$^{-1}$): 2981 (w), 1637 (w), 1320 (m), 1131 (s), 1064 (m), 834 (m), 739 (m), 695 (s). LRMS (ESI): 340.1 (100%) [M+H]$^+$.

(E)-4-((benzhydrylimino)methyl)benzonitrile (2l)

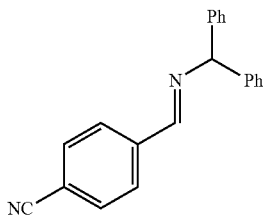

Prepared via Method A. $^1$H NMR (500 MHz, CDCl$_3$): δ 8.48 (1H, s), 7.96 (2H, d, J=8.0 Hz), 7.72 (2H, d, J=8.5 Hz), 7.44-7.46 (4H, m), 7.37-7.42 (4H, m), 7.29-7.32 (2H, m), 5.70 (1H, s). $^{13}$C {$^1$H} NMR (125 MHz, CDCl$_3$): δ 158.9, 143.2, 140.0, 132.3, 128.8, 128.5, 128.3, 127.5, 127.2, 118.5, 114.0, 78.0. IR (cm$^{-1}$): 3064 (w), 3023 (w), 2874 (w), 2852 (w), 2222 (m), 1634 (m), 1490 (m), 1451 (m), 1378 (m), 1025 (m), 855 (m), 829 (m), 752 (s), 702 (s). LRMS (ESI): 297.1 (30%) [M+H]$^+$.

(E)-N-(4-bromobenzylidene)diphenylmethanamine (2m)

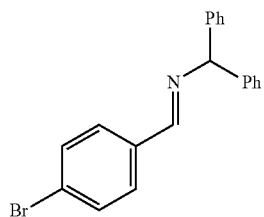 [SMILES: Clc1ccc(/C=N/C(c2ccccc2)c2ccccc2)cc1]

Prepared via Method A. $^1$H NMR (500 MHz, CDCl$_3$): δ 8.41 (1H, s), 7.74-7.76 (2H, m), 7.58-7.60 (2H, m), 7.44-7.45 (4H, m), 7.34-7.39 (4H, m), 7.27-7.30 (2H, m), 5.64 (1H, s). $^{13}$C{$^1$H} NMR (125 MHz, CDCl$_3$): δ 159.5, 143.6, 135.2, 131.7, 129.8, 128.4, 127.6, 127.0, 125.1, 77.8. IR (cm$^{-1}$): 3062 (w), 3023 (w), 2856 (m), 1638 (m), 1567 (m), 1484 (m), 1068 (m), 1012 (m), 812 (m), 744 (m), 698 (s). LRMS (ESI): 350.1 (60%) [M+H]$^+$.

(E)-N-(2-methoxybenzylidene)diphenylmethanamine (2n)

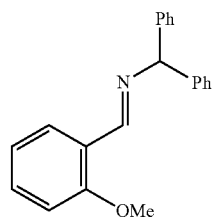 [SMILES: COc1ccccc1/C=N/C(c1ccccc1)c1ccccc1]

Prepared via Method A. $^1$H NMR (500 MHz, CDCl$_3$): δ 8.99 (1H, s), 8.26 (1H, dd, J=1.8, 7.8 Hz), 7.48-7.50 (4H, m), 7.38 (4H, t, J=7.5 Hz), 7.27-7.30 (2H, m), 7.06 (1H, t, J=7.3 Hz), 6.96 (1H, d, J=8.5 Hz), 5.67 (1H, s), 3.89 (3H, s). $^{13}$C{$^1$H} NMR (125 MHz, CDCl$_3$): δ 158.8, 156.6, 144.3, 131.9, 128.3, 127.7, 127.6, 126.8, 124.7, 120.7, 110.9, 78.4, 55.4. IR (cm$^{-1}$): 3079 (w), 3020 (w), 2938 (w), 2837 (w), 1631 (m), 1598 (m), 1487 (m), 1378 (m), 1175 (m), 1080 (m), 775 (s), 739 (s), 697 (s). LRMS (ESI): 302.2 (100%) [M+H]$^+$.

(E)-N-(2-bromobenzylidene)diphenylmethanamine (2o)

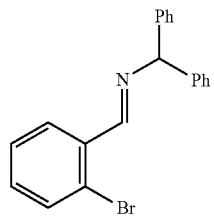 [SMILES: Brc1ccccc1/C=N/C(c1ccccc1)c1ccccc1]

Prepared via Method A. Spectroscopic data match previously reported data in Krueger et al. (See *J. Am. Chem. Soc.* 121:4284 (1999)).

(E)-N-(3-bromobenzylidene)diphenylmethanamine (2p)

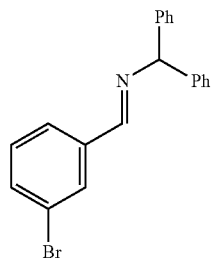 [SMILES: Brc1cccc(/C=N/C(c2ccccc2)c2ccccc2)c1]

Prepared via Method A. $^1$H NMR (500 MHz, CDCl$_3$): δ 8.39 (1H, s), 8.09 (1H, m), 7.73 (1H, dd, J=1.3, 7.8 Hz), 7.56-7.59 (1H, m), 7.44 (4H, d, J=7.0 Hz), 7.37 (4H, t, J=7.8 Hz), 7.27-7.32 (3H, m), 5.65 (1H, s). $^{13}$C {$^1$H} NMR (125 MHz, CDCl$_3$): δ 159.2, 143.5, 138.2, 133.6, 130.9, 130.0, 128.5, 127.6, 127.3, 127.1, 122.8, 77.8. IR (cm$^{-1}$): 3057 (w), 3026 (w), 2839 (m), 1658 (m), 1565 (m), 1492 (m), 1447 (m), 1381 (m), 1210 (m), 1024 (m), 787 (m), 759 (m), 741 (s), 697 (s). LRMS (ESI): 350.1 (60%) [M+H]$^+$.

(E)-N-(furan-2-ylmethylene)diphenylmethanamine (2q)

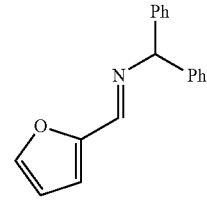 [SMILES: C(=N\C(c1ccccc1)c1ccccc1)/c1ccco1]

Prepared via Method A. Spectroscopic data match previously reported data in Cainelli et al. (See *J. Org. Chem.,* 61:5134 (1996)).

(E)-N-(furan-3-ylmethylene)diphenylmethanamine (2r)

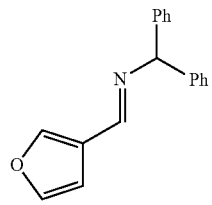 [SMILES: C(=N\C(c1ccccc1)c1ccccc1)/c1ccoc1]

Prepared via Method A. $^1$H NMR (500 MHz, CDCl$_3$): δ 8.36 (1H, s), 7.74 (1H, s), 7.44-7.45 (1H, m), 7.38-7.40 (4H, m), 7.33-7.36 (4H, m), 7.24-7.28 (2H, m), 6.95 (1H, s), 5.57 (1H, s). $^{13}$C {$^1$H} NMR (125 MHz, CDCl$_3$): δ 152.5, 145.3, 143.9, 143.7, 128.4, 127.7, 127.0, 125.7, 108.2, 77.9. IR (cm$^{-1}$): 3082 (w), 3051 (w), 1644 (m), 1511 (m), 1492 (m), 1153 (m), 1076 (m), 1017 (m), 774 (m), 745 (m), 726 (m), 698 (s). LRMS (ESI): 262.1 (80%) [M+H]$^+$.

(E)-diphenyl-N-(thiophen-2-ylmethylene)methanamine (2s)

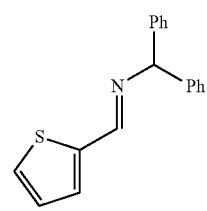 [SMILES: C(=N\C(c1ccccc1)c1ccccc1)/c1cccs1]

Prepared via Method A. $^1$H NMR (500 MHz, CDCl$_3$): δ 8.52 (1H, s), 7.44-7.46 (5H, m), 7.36-7.40 (5H, m), 7.28-7.31 (2H, m), 7.10 (1H, dd, J=3.5, 5.0 Hz), 5.66 (1H, s). $^{13}$C{$^1$H} NMR (125 MHz, CDCl$_3$): δ 154.0, 143.6, 142.7, 130.6, 129.1, 128.4, 127.7, 127.3, 127.0, 77.1. IR (cm$^{-1}$): 3103 (w), 3061 (w), 2848 (w), 1626 (m), 1491 (m), 1430 (m), 1218 (m), 1022 (m), 758 (m), 748 (m), 699 (s). LRMS (ESI): 278.1 (100%) [M+H]$^+$.

(E)-N-(cyclohexenylmethylene)diphenylmethanamine (2t)

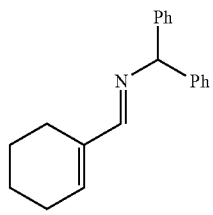 [SMILES: C1=C(/C=N/C(c2ccccc2)c2ccccc2)CCCC1]

Prepared via Method A. $^1$H NMR (500 MHz, CDCl$_3$): δ 7.98 (1H, s), 7.39-7.41 (4H, m), 7.33-7.36 (4H, m), 7.24-7.28 (2H, m), 6.20 (1H, apparent sextet, J=1.8 Hz), 5.46 (1H, s), 2.48-2.50 (2H, m), 2.23-2.26 (2H, m), 1.68-1.74 (4H, m). $^{13}$C {$^1$H} NMR (125 MHz, CDCl$_3$): δ 163.9, 144.4, 138.9, 138.4, 128.3, 127.6, 126.7, 77.6, 26.1, 23.9, 22.5, 22.0. IR (cm$^{-1}$): 3069 (w), 3022 (w), 2932 (m br), 2848 (w), 1643 (m), 1627 (m), 1491 (m), 1448 (m), 1376 (m), 1087 (m), 745 (m), 697 (s). LRMS (ESI): 276.2 (100%) [M+H]$^+$.

(E)-N-((E)-2-methylpent-2-enylidene)diphenylmethanamine (2u)

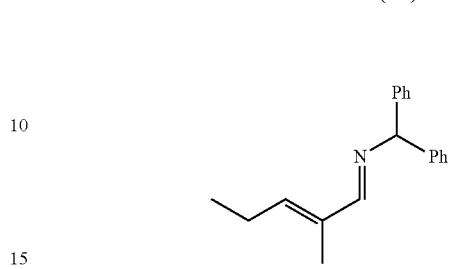

Prepared via Method A. $^1$H NMR (500 MHz, CDCl$_3$): δ 8.03 (1H, s), 7.45 (4H, d, J=8.0 Hz), 7.39 (4H, t, J=7.8 Hz), 7.29 (2H, tt, J=1.6, 7.3 Hz), 5.94 (1H, td, J=1.6, 7.5 Hz), 5.52 (1H), 2.33 (2H, p, J=7.5 Hz), 2.05 (3H, s), 1.12 (3H, t, J=7.5 Hz). $^{13}$C{$^1$H} NMR (125 MHz, CDCl$_3$): δ 165.2, 144.4, 143.8, 135.7, 128.3, 128.3, 128.1, 127.6, 127.5, 126.8, 126.7, 77.5, 21.8, 13.4, 11.6. IR (cm$^{-1}$): 3061 (w), 3026 (w), 2966 (w), 2932 (w), 2872 (w), 1626 (m), 1492 (m), 1451 (m), 1051 (m), 1030 (m), 740 (m), 696 (s). LRMS (ESI): 264.2 (100%) [M+H]$^+$.

(E)-diphenyl-N-((E)-3-phenylallylidene)methanamine (2v)

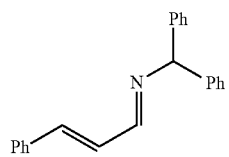 [SMILES: C(=C\c1ccccc1)/C=N/C(c1ccccc1)c1ccccc1]

Prepared via Method A. $^1$H NMR (500 MHz, CDCl$_3$): δ 8.24 (1H, d, J=8.5 Hz), 7.52-7.53 (2H, m), 7.36-7.42 (11H, m), 7.27-7.30 (2H, m), 7.13 (1H, dd, J=8.8, 16.3 Hz), 7.01 (1H, d, J=16.0 Hz), 5.54 (1H, s). $^{13}$C {$^1$H} NMR (125 MHz, CDCl$_3$): δ 162.8, 143.6, 142.3, 135.7, 129.2, 128.8, 128.4, 128.3, 127.7, 127.2, 127.0, 78.2. IR (cm$^{-1}$): 3080 (w), 3026 (w), 2851 (w), 1630 (m), 1489 (m), 1446 (m), 1151 (m), 997 (m), 964 (m), 742 (s), 692 (s). LRMS (ESI): 298.2 (100%) [M+H]$^+$.

(E)-N-((E)-hex-2-enylidene)diphenylmethanamine (2w)

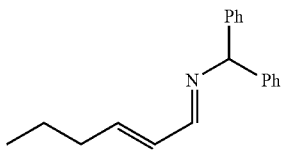 [SMILES: CCC/C=C/C=N/C(c1ccccc1)c1ccccc1]

Prepared via Method A. $^1$H NMR (500 MHz, CDCl$_3$): δ 8.07 (1H, d, J=8.8 Hz), 7.35-7.41 (8H, m), 7.26-7.30 (2H, m), 6.46 (1H, dd, J=8.8, 15.6 Hz), 6.27 (1H, dt, J=6.7, 15.5 Hz), 5.45 (1H, s), 2.25 (2H, q, J=7.1 Hz), 1.54 (2H, sextet, J=7.4 Hz), 1.00 (3H, t, J=7.4 Hz). $^{13}$C {$^1$H} NMR (125 MHz, CDCl$_3$): δ 162.9, 146.3, 143.7, 130.7, 128.3, 127.6, 126.8, 78.0, 34.6, 21.6, 13.6. IR (cm$^{-1}$): 3061 (w), 3026 (w), 2959 (w), 2929 (w), 2871 (w), 1652 (m), 1492 (m), 1451 (m), 1028 (m), 989 (m), 961 (m), 741 (s), 697 (s). LRMS (ESI): 264.2 (100%) [M+H]$^{+}$.

Preparation of α-Aminonitriles

A flame-dried 25-mL round-bottomed flask containing a stir bar was charged with imine (1.0 mmol, 1.0 equiv) and (S)—N-benzhydryl-2-(3-(3,5-bis(trifluoromethyl)phenyl)thioureido)-N,3,3-trimethylbutanamide (4e) (11.6 mg, 0.02 mmol, 0.02 equiv). The flask was capped with a virgin rubber septum and flushed with N$_2$. Toluene (3.75 mL) was added via syringe under N$_2$, and the mixture was stirred at room temperature until a homogenous solution formed. The flask was then cooled in a dry ice/acetone (−78° C.) bath for 10 min. A stock solution of HCN was prepared as follows: a flame-dried 10-mL round-bottomed flask containing a stir bar was capped with a virgin septum. Toluene (1.25 mL) was added via syringe under N$_2$, and the flask was cooled in an ice-water bath for 10 min. TMSCN (0.27 mL, 2.0 mmol, 2.0 equiv) was added via syringe. Methanol (0.075 mL, 1.9 mmol, 1.9 equiv) was then added over 90 s with stirring. The stock solution was stirred at 0° C. for 30 min and then added via syringe to reaction mixture over a period of two minutes with stirring. The reaction flask was sealed with Parafilm, transferred to either a −30° C. freezer or 0° C. refrigerator, and aged for 20 h. After 20 h, the reaction flask was transferred to a well-ventilated fume hood, and the reaction mixture was concentrated under reduced pressure (1 torr). The residue was subjected to purification by flash column chromatography with Et$_2$O/hexanes as the eluent. α-Aminonitriles that are solids can show enantiomeric enrichment upon crystallization. All solid α-aminonitriles were homogenized using a metal spatula prior to chiral HPLC analysis to ensure that an accurate measurement of enantioselectivity was obtained. Samples that were not mechanically homogenized yielded inconsistent enantiomeric excess values in the chiral HPLC analysis.

(R)-2-(benzhydrylamino)-3,3-dimethylbutanenitrile (3a)

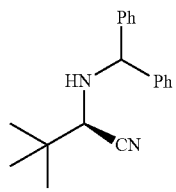 [SMILES: CC(C)(C)[C@H](C#N)NC(c1ccccc1)c1ccccc1]

The reaction was run at −30° C. for 20 h without stirring using (E)-N-(2,2-dimethylpropylidene) diphenylmethanamine (251 mg, 1.0 mmol, 1.0 equiv). The product was subjected to purification by flash column chromatography (9:1, hexanes:Et$_2$O) to afford (R)-2-(benzhydrylamino)-3,3-dimethylbutanenitrile (275 mg, 0.99 mmol, 99% yield) as a clear colorless oil. The enantiomeric excess was determined to be 93% by chiral HPLC analysis (AS-H, 5.0% IPA in hexanes, 1.0 mL/min, 210 nm, t$_R$(major)=8.7 min, t$_R$(minor)=6.0 min); [α]$_D^{24}$=+113.0° (c=1.0, CHCl$_3$); lit [α]$_D^{20}$=+87.1° (c=1.19, CHCl$_3$), 63% ee, (R)-enantiomer. Spectroscopic data match previously reported data in Krueger et al. (See J. Am. Chem. Soc. 121:4284 (1999)).

(R)-2-(benzhydrylamino)-3-ethyl-3-methylpentanenitrile (3b)

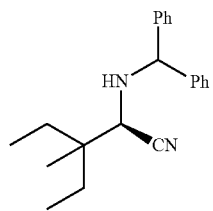 [SMILES: CCC(C)(CC)[C@H](C#N)NC(c1ccccc1)c1ccccc1]

The reaction was run at −30° C. for 20 h without stirring using (E)-N-(2-ethyl-2-methylbutylidene)diphenylmethanamine (279 mg, 1.0 mmol, 1.0 equiv). The product was subjected to purification by flash column chromatography (9:1, hexanes:Et$_2$O) to afford (R)-2-(benzhydrylamino)-3-ethyl-3-methylpentanenitrile (303 mg, 0.99 mmol, 99% yield) as a clear colorless oil. The enantiomeric excess was determined to be 96% by chiral HPLC analysis (AS-H, 5.0% IPA in hexanes, 1.0 mL/min, 210 nm, t$_R$(major)=8.4 min, t$_R$(minor)=5.3 min); [α]$_D^{23}$=+124.6° (c=1.0, CHCl$_3$). $^1$H NMR (500 MHz, CDCl$_3$): δ 7.48 (2H, d, J=7.0 Hz), 7.45 (2H, d, J=7.0 Hz), 7.32 (4H, td, J=8.0, 3.0 Hz), 7.22-7.27 (2H, m), 5.11 (1H, s), 3.21 (1H, d, J=13.5 Hz), 1.80 (1H, d, J=13.0 Hz), 1.54 (3H, apparent sextet, J=7.4 Hz), 1.41 (1H, apparent sextet, J=7.3 Hz), 0.98 (3H, s), 0.75 (6H, apparent td, J=7.5, 2.2 Hz). $^{13}$C {$^1$H} NMR (125 MHz, CDCl$_3$): δ 143.5, 141.3, 128.7, 128.7, 127.8, 127.7, 127.5, 126.9, 119.7, 65.7, 56.1, 39.3, 28.2, 27.4, 20.5, 7.80, 7.59. IR (cm$^{-1}$): 3314 (w), 3028 (w), 2967 (m), 2939 (m), 2224 (w), 1493 (m), 1453 (m), 1112 (m), 745 (s), 702 (s).

(R)-2-(benzhydrylamino)-3-methyl-3-phenylbutanenitrile (3c)

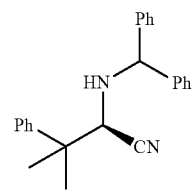

The reaction was run at −30° C. for 20 h without stirring using (E)-N-(2-methyl-2-phenylpropylidene)diphenylmethanamine (313 mg, 1.0 mmol, 1.0 equiv). The product was subjected to purification by flash column chromatography (9:1, hexanes:Et$_2$O) to afford (R)-2-(benzhydrylamino)-3-methyl-3-phenylbutanenitrile (331 mg, 0.97 mmol, 97% yield) as a white solid. The enantiomeric excess was determined to be 85% by chiral HPLC analysis (OD-H, 1.0% IPA in hexanes, 1.0 mL/min, 220 nm, t$_R$(major)=7.8 min, t$_R$(minor)=9.0 min); [α]$_D^{24}$=+81.8° (c=1.0, CHCl$_3$). $^1$H NMR (500 MHz, CDCl$_3$): δ 7.45-7.47 (2H, m), 7.37-7.43 (4H, m), 7.28-7.35 (8H, m), 7.24-7.26 (1H, m), 5.06 (1H, s), 3.47 (1H, d, J=12.5 Hz), 1.72 (1H, d, J=12.5 Hz), 1.68 (6H, s). $^{13}$C {$^1$H} NMR (125 MHz, CDCl$_3$): δ 143.4, 143.3, 141.1, 128.7, 128.6, 128.4, 127.6, 127.4, 127.0, 126.8, 126.5, 119.2, 65.3, 59.2, 40.8, 25.9, 25.0. IR (cm$^{-1}$): 3348 (w), 3058 (w), 3025 (w), 2975 (w), 2228 (w), 1493 (m), 1452 (m), 1309 (m), 1122 (m), 1032 (m), 889 (w), 768 (s), 745 (s), 702 (s).

(R)-2-(benzhydrylamino)-2-(1-methylcyclohexyl)acetonitrile (3d)

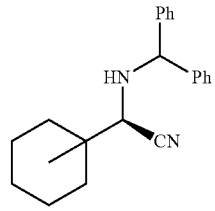

The reaction was run at −30° C. for 20 h without stirring using (E)-N-((1-methylcyclohexyl)methylene)diphenylmethanamine (291 mg, 1.0 mmol, 1.0 equiv). The product subjected to purification by flash column chromatography (9:1, hexanes:Et$_2$O) to afford (R)-2-(benzhydrylamino)-2-(1-methylcyclohexyl)acetonitrile (315 mg, 0.99 mmol, 99% yield) as a clear colorless oil. The enantiomeric excess was determined to be 95% by chiral HPLC analysis (AD-H, 5.0% IPA in hexanes, 1.0 mL/min, 230 nm, $t_R$(major)=5.8 min, $t_R$(minor)=5.2 min); $[\alpha]_D^{24}$=+108.8° (c=1.0, CHCl$_3$). $^1$H NMR (500 MHz, CDCl$_3$): δ 7.50 (2H, d, J=7.0 Hz), 7.45 (2H, d, J=7.0 Hz), 7.30-7.35 (4H, m), 7.23-7.28 (2H, m), 5.12 (1H, s), 3.23 (1H, d, J=12.5 Hz), 1.80 (1H, d, J=13.0 Hz), 1.48-1.55 (5H, m), 1.39-1.45 (6H, m), 1.22-1.26 (1H, m), 1.09 (3H, s). $^{13}$C {$^1$H} NMR (125 MHz, CDCl$_3$): δ 143.5, 141.4, 128.7, 127.7, 127.6, 127.0, 119.4, 65.7, 58.3, 40.3, 36.8, 34.8, 34.2, 25.9, 21.6, 21.4, 20.6. IR (cm$^{-1}$): 3314 (w), 3028 (w), 2927 (m), 2853 (m), 2224 (w), 1493 (w), 1452 (m), 1104 (m), 1028 (m), 745 (s), 701 (s).

(R)-2-(benzhydrylamino)-2-(1-adamantyl)acetonitrile (3e)

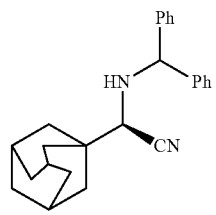 [SMILES: N#C[C@H](NC(c1ccccc1)c1ccccc1)C12CC3CC(CC(C3)C1)C2]

The reaction was run at −30° C. for 20 h without stirring using (E)-N-(1-adamantyl)diphenylmethanamine (330 mg, 1.0 mmol, 1.0 equiv). The product was subjected to purification by flash column chromatography (9:1, hexanes:Et$_2$O) to afford (R)-2-(benzhydrylamino)-2-(1-adamantyl)acetonitrile (352 mg, 0.99 mmol, 99% yield) as an off-white solid. The enantiomeric excess was determined to be 93% by chiral HPLC analysis (OD-H, 2.0% IPA in hexanes, 1.0 mL/min, 220 nm, $t_R$(major)=5.4 min, $t_R$(minor)=5.7 min); $[\alpha]_D^{24}$=+69.9° (c=1.0, CHCl$_3$); $^1$H NMR (500 MHz, CDCl$_3$): δ 7.51 (2H, d, J=7.5 Hz), 7.47 (2H, d, J=7.0 Hz), 7.32-7.39 (4H, m), 7.24-7.29 (2H, m), 5.14 (1H, s), 3.03 (1H, s), 2.08 (3H, s), 1.63-1.86 (13H, m). $^{13}$C{$^1$H} NMR (125 MHz, CDCl$_3$): δ 143.5, 141.3, 128.7, 128.7, 127.6, 127.5, 127.4, 127.0, 119.0, 65.5, 59.5, 38.7, 37.3, 36.6, 36.5, 35.8, 28.1. IR (cm$^{-1}$): 3302 (w), 3025 (w), 2912 (m), 2849 (m), 2222 (w), 1493 (w), 1450 (m), 1346 (w), 1029 (w), 895 (w), 743 (s), 700 (s).

(R)-2-(benzhydrylamino)-2-cyclohexylacetonitrile (3f)

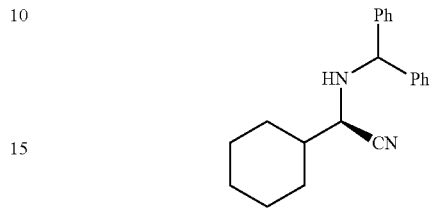

The reaction was run at −30° C. for 20 h without stirring using (E)-N-(cyclohexylmethylene)diphenylmethanamine (277 mg, 1.0 mmol, 1.0 equiv). The product was subjected to purification by flash column chromatography (9:1, hexanes:Et$_2$O) to afford (R)-2-(benzhydrylamino)-2-cyclohexylacetonitrile (301 mg, 0.99 mmol, 99% yield) as a white solid. The enantiomeric excess was determined to be 74% by chiral HPLC analysis (OD-H, 2.0% IPA in hexanes, 1.0 mL/min, 230 nm, $t_R$(major)=6.3 min, $t_R$(minor)=8.0 min); $[\alpha]_D^{23}$=+59.9° (c=1.0, CHCl$_3$). $^1$H NMR (500 MHz, CDCl$_3$): δ 7.50 (2H, d, J=7.0 Hz), 7.44 (2H, d, J=7.0 Hz), 7.31-7.37 (4H, m), 7.23-7.29 (2H, m), 5.15 (1H, s), 3.25 (1H, d, J=7.0 Hz), 2.00 (1H, d, J=12.5 Hz), 1.87 (1H, d, J=10.5 Hz), 1.79-1.82 (2H, m), 1.69-1.75 (2H, m), 1.11-1.33 (6H, m). $^{13}$C{$^1$H} NMR (125 MHz, CDCl$_3$): δ 143.3, 141.3, 128.8, 128.7, 127.6, 127.5, 127.3, 127.0, 119.6, 65.5, 54.1, 40.9, 29.6, 29.0, 26.0, 25.7, 25.6. IR (cm$^{-1}$) 3329 (w), 3028 (w), 2930 (m), 2845 (m), 2222 (w), 1493 (m), 1450 (m), 1112 (m), 1027 (m), 880 (m), 750 (s), 707 (s), 697 (s).

(R)-2-(benzhydrylamino)-2-(4-methoxyphenyl)acetonitrile (3g)

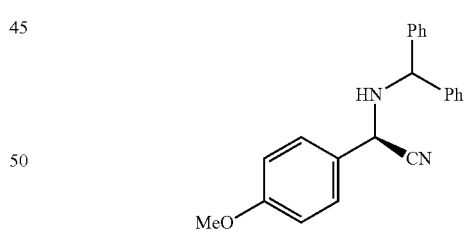

The reaction was run at −30° C. for 20 h without stirring using (E)-N-(4-methoxybenzylidene)diphenylmethanamine (301 mg, 1.0 mmol, 1.0 equiv). The product was subjected to purification by flash column chromatography (7:1, hexanes:Et$_2$O) to afford (R)-2-(benzhydrylamino)-2-(4-methoxyphenyl)acetonitrile (324 mg, 0.99 mmol, 99% yield) as a white solid. The enantiomeric excess was determined to be 99% by chiral HPLC analysis (S,S-whelk, 2.0% IPA in hexanes, 1.0 mL/min, 200 nm, $t_R$(major)=19.6 min, $t_R$(minor)=18.4 min); $[\alpha]_D^{24}$+43.0° (c=1.0, CHCl$_3$); lit $[\alpha]_D^{24}$−38.0° (c=1.0, CHCl$_3$), 91% ee, (S)-enantiomer. Spectroscopic data match previously reported data in Krueger et al. (See *J. Am. Chem. Soc.* 121:4284 (1999)).

(R)-2-(benzhydrylamino)-2-p-tolylacetonitrile (3h)

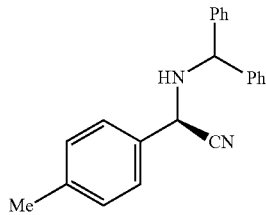

The reaction was run at −30° C. for 20 h without stirring using (E)-N-(4-methylbenzylidene)diphenylmethanamine (285 mg, 1.0 mmol, 1.0 equiv). The product was subjected to purification by flash column chromatography (9:1, hexanes: Et$_2$O) to afford (R)-2-(benzhydrylamino)-2-p-tolylacetonitrile (307 mg, 0.98 mmol, 98% yield) as a white solid. The enantiomeric excess was determined to be 98% by chiral HPLC analysis (OD-H, 5.0% IPA in hexanes, 1.0 mL/min, 220 nm, t$_R$(major)=6.7 min, t$_R$(minor)=7.3 min); $[\alpha]_D^{24}$+52.8° (c=1.0, CHCl$_3$); lit $[\alpha]_D^{20}$+41.0° (c=1.13, CHCl$_3$), 80% ee, (R)-enantiomer. Spectroscopic data matched previously reported data in Jiao et al. (See *Eur. J. Org. Chem.*, 3818-3826 (2003)).

(R)-2-(benzhydrylamino)-2-phenylacetonitrile (3i)

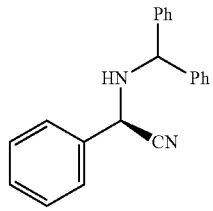 [SMILES: N#C[C@H](NC(c1ccccc1)c1ccccc1)c1ccccc1]

The reaction was run at −30° C. for 20 h without stirring using (E)-N-benzylidenediphenylmethanamine (271 mg, 1.0 mmol, 1.0 equiv). The product was subjected to purification by flash column chromatography (9:1, hexanes:Et$_2$O) to afford (R)-2-(benzhydrylamino)-2-phenylacetonitrile (293 mg, 0.98 mmol, 98% yield) as a white solid. The enantiomeric excess was determined to be 98% by chiral HPLC analysis (OD-H, 5.0% IPA in hexanes, 1.0 mL/min, 220 nm, t$_R$(major)=7.1 min, t$_R$(minor)=7.9 min); $[\alpha]_D^{24}$+66.1° (c=1.0, CHCl$_3$); lit $[\alpha]_D^{24}$−64.2° (c=5.0, CHCl$_3$), >99% ee, (S)-enantiomer. Spectroscopic data match previously reported data in Krueger et al. (See *J. Am. Chem. Soc.* 121:4284 (1999)).

(R)-2-(benzhydrylamino)-2-(4-chlorophenyl)acetonitrile (3j)

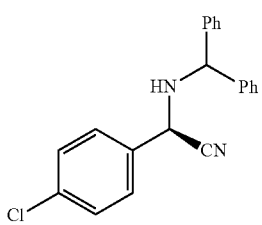 [SMILES: N#C[C@H](NC(c1ccccc1)c1ccccc1)c1ccc(Cl)cc1]

The reaction was run at −30° C. for 20 h without stirring using (E)-N-(4-chlorobenzylidene)diphenylmethanamine (306 mg, 1.0 mmol, 1.0 equiv). The product was subjected to purification by flash column chromatography (9:1, hexanes: Et$_2$O) to afford (R)-2-(benzhydrylamino)-2-(4-chlorophenyl)acetonitrile (324 mg, 0.97 mmol, 97% yield) as a white solid. The enantiomeric excess was determined to be 98% ee by chiral HPLC analysis (OD-H, 5.0% IPA in hexanes, 1.0 mL/min, 220 nm, t$_R$(major)=9.6 min, t$_R$(minor)=11.7 min); $[\alpha]_D^{24}$+42.3° (c=1.0, CHCl$_3$); lit $[\alpha]_D^{20}$=+35.1° (c=1.09, CHCl$_3$), 84% ee, (R)-enantiomer. Spectroscopic data match previously reported data in Lyer et al. (See *J. Am. Chem. Soc.*, 118:4910 (1996)).

(R)-2-(benzhydrylamino)-2-(4-(trifluoromethyl)phenyl)acetonitrile (3k)

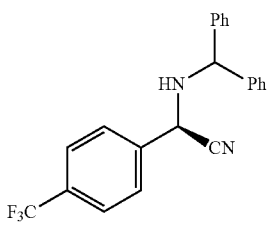 [SMILES: N#C[C@H](NC(c1ccccc1)c1ccccc1)c1ccc(C(F)(F)F)cc1]

The reaction was run at 0° C. for 20 h with stirring using (E)-diphenyl-N-(4-(trifluoromethyl)benzylidene)methanamine (339 mg, 1.0 mmol, 1.0 equiv). The product was subjected to purification by flash column chromatography (9:1, hexanes:Et$_2$O) to afford (R)-2-(benzhydrylamino)-2-(4-(trifluoromethyl)phenyl)acetonitrile (360 mg, 0.98 mmol, 98% yield) as a white solid. This enantiomeric excess was determined to be 96% by chiral HPLC analysis (OD-H, 5.0% IPA in hexanes, 1.0 mL/min, 220 nm, t$_R$(major)=11.5 min, t$_R$(minor)=13.3 min); $[\alpha]_D^{24}$=+50.3° (c=1.0, CHCl$_3$). $^1$H NMR (500 MHz, CDCl$_3$): δ 7.72 (4H, s), 7.61 (2H, d, J=8.0 Hz), 7.49 (2H, d, J=7.5 Hz), 7.42 (2H, t, J=7.8 Hz), 7.31-7.36 (3H, m), 7.25-7.28 (1H, m), 5.29 (1H, s), 4.69 (1H, d, J=9.0 Hz), 2.23 (1H, d, J=8.5 Hz). $^{13}$C $\{^1$H$\}$ NMR (125 MHz, CDCl$_3$): δ 142.4, 140.7, 138.7, 131.3 (q, J$_{C-F}$=32.3 Hz), 129.1, 128.8, 128.1, 127.8, 127.7, 127.4, 127.0, 125.9 (q, J$_{C-F}$=2.5 Hz), 123.7 (q, J$_{C-F}$=270.0 Hz), 118.1, 65.6, 51.9. IR (cm$^{-1}$): 3297 (m), 3065 (w), 3028 (w), 2842 (w), 2231 (w), 1618 (w), 1453 (m), 1323 (s), 1166 (m), 1125 (s), 1111 (s), 1066 (m), 1017 (m), 922 (m), 749 (m), 699 (s).

(R)-4-((benzhydrylamino)(cyano)methyl)benzonitrile (3l)

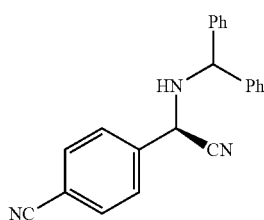 [SMILES: N#Cc1ccc([C@H](C#N)NC(c2ccccc2)c2ccccc2)cc1]

The reaction was run at 0° C. for 20 h with stirring using (E)-4-((benzhydrylimino)methyl)benzonitrile (296 mg, 1.0 mmol, 1.0 equiv) and 10 mol % of (S)—N-benzhydryl-2-(3-(3,5-bis(trifluoromethyl)phenyl)thioureido)-N,3,3-trimethyl butanamide (4e). The product was subjected to purification by flash column chromatography (9:1, hexanes:Et$_2$O) to afford (R)-4-((benzhydrylamino) (cyano)methyl)benzonitrile (310 mg, 0.96 mmol, 96% yield) as a white solid. The enantiomeric excess was determined to be 93% by chiral HPLC analysis (OD-H, 5.0% IPA in hexanes, 1.0 mL/min, 230 nm, $t_R$(major)=41.1 min, $t_R$(minor)=56.4 min); $[\alpha]_D^{24}$=+27.3° (c=1.0, CHCl$_3$). $^1$H NMR (500 MHz, CDCl$_3$): δ 7.72 (4H, s), 7.57 (2H, d, J=7.5 Hz), 7.45 (2H, d, J=7.5 Hz), 7.39 (2H, t, J=7.8 Hz), 7.29-7.34 (3H, m), 7.23-7.27 (1H, m), 5.25 (1H, s), 4.67 (1H, br s), 2.25 (1H, br s). $^{13}$C {$^1$H} NMR (125 MHz, CDCl$_3$): δ 142.2, 140.5, 139.7, 132.7, 129.1, 128.8, 128.2, 128.0, 127.9, 127.4, 127.0, 118.1, 117.7, 113.1, 65.7, 52.0. IR (cm$^{-1}$): 3310 (m), 3296 (m), 3025 (w), 2925 (w), 2845 (w), 2232 (m), 1609 (w), 1492 (m), 1453 (m), 1349 (m), 1189 (m), 925 (m), 746 (s), 703 (s).

(R)-2-(benzhydrylamino)-2-(4-bromophenyl)acetonitrile (3m)

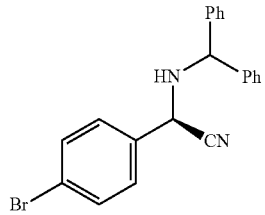

The reaction was run at −30° C. for 20 h with stirring using (E)-N-(4-bromobenzylidene)diphenylmethanamine (350 mg, 1.0 mmol, 1.0 equiv). The product was subjected to purification by flash column chromatography (9:1, hexanes: Et$_2$O) to afford (R)-2-(benzhydrylamino)-2-(4-bromophenyl)acetonitrile (369 mg, 0.98 mmol, 98% yield) as a white solid. The enantiomeric excess was determined to be 99% by chiral HPLC analysis (OD-H, 2.0% IPA in hexanes, 1.0 mL/min, 220 nm, $t_R$(major)=15.1 min, $t_R$(minor)=18.4 min); $[\alpha]_D^{24}$=+29.4° (c=1.0, CHCl$_3$). $^1$H NMR (500 MHz, CDCl$_3$): δ 7.56-7.59 (4H, m), 7.46 (4H, t, J=8.8 Hz), 7.41 (2H, t, J=7.5 Hz), 7.30-7.35 (3H, m), 7.26 (1H, t, J=7.3 Hz), 5.26 (1H, s), 4.58 (1H, d, J=11.5 Hz), 2.18 (1H, d, J=12.0 Hz). $^{13}$C{$^1$H} NMR (125 MHz, CDCl$_3$): δ 142.4, 140.8, 133.8, 132.1, 129.0, 128.8, 128.7, 128.0, 127.7, 127.3, 127.0, 123.1, 118.2, 65.5, 51.7. IR (cm$^{-1}$): 3303 (m), 3062 (w), 3026 (w), 2836 (w), 2224 (w), 1594 (w), 1488 (m), 1453 (m), 1187 (w), 1100 (m), 920 (m), 819 (m), 745 (s), 698 (s).

(R)-2-(benzhydrylamino)-2-(2-methoxyphenyl)acetonitrile (3n)

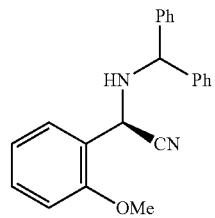 [SMILES: COc1ccccc1[C@H](C#N)NC(c1ccccc1)c1ccccc1]

The reaction was run at −30° C. for 20 h without stirring using (E)-N-(2-methoxybenzylidene)diphenylmethanamine (301 mg, 1.0 mmol, 1.0 equiv). The product was subjected to purification by flash column chromatography (7:1, hexanes: Et$_2$O) to afford (R)-2-(benzhydrylamino)-2-(2-methoxyphenyl)acetonitrile (318 mg, 0.97 mmol, 97% yield) as a white solid. The enantiomeric excess was determined to be 88% by chiral HPLC analysis (OD-H, 2.0% IPA in hexanes, 1.0 mL/min, 220 nm, $t_R$(major)=11.7 min, $t_R$(minor)=12.8 min); $[\alpha]_D^{23}$=+65.3° (c=1.0, CHCl$_3$); lit $[\alpha]_D^{24}$=−57.0° (c=1.0, CHCl$_3$), 83% ee, (S)-enantiomer. $^1$H NMR (500 MHz, CDCl$_3$): δ 7.56 (2H, d, J=8.0 Hz), 7.48 (2H, d, J=8.0 Hz), 7.37-7.41 (3H, m), 7.30-7.35 (4H, m), 7.24-7.28 (1H, m), 7.00 (1H, t, J=7.5 Hz), 6.97 (1H, d, J=8.5 Hz), 5.23 (1H, s), 4.71 (1H, br d, J=6.5 Hz), 3.89 (3H, s), 2.60 (1H br s). $^{13}$C {$^1$H} NMR (125 MHz, CDCl$_3$): δ 157.0, 142.9, 141.4, 130.5, 128.8, 128.7, 128.7, 127.6, 127.5, 127.4, 127.2, 126.4, 120.9, 119.0, 111.3, 65.3, 55.5, 48.4. IR (cm$^{-1}$): 3322 (w), 3027 (w), 2975 (w), 2939 (w), 2227 (w), 1600 (m), 1493 (m), 1450 (m), 1248 (m), 1026 (m), 910 (m), 747 (s), 698 (s).

(R)-2-(benzhydrylamino)-2-(2-bromophenyl)acetonitrile (3o)

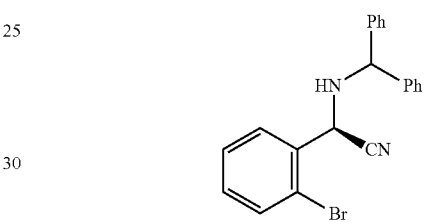

The reaction was run at 0° C. for 20 h with stirring using (E)-N-(2-bromobenzylidene)diphenylmethanamine (350 mg, 1.0 mmol, 1.0 equiv). The product was subjected to purification by flash column chromatography (9:1, hexanes: Et$_2$O) to afford (R)-2-(benzhydrylamino)-2-(2-bromophenyl)acetonitrile (362 mg, 0.96 mmol, 96% yield) as a white solid. This enantiomeric excess was determined to be 97% by chiral HPLC analysis (OD-H, 2.0% IPA in hexanes, 1.0 mL/min, 200 nm, $t_R$(major)=12.7 min, $t_R$(minor)=17.8 min); $[\alpha]_D^{25}$=+130.0° (c=1.0, CHCl$_3$); lit $[\alpha]_D^{24}$=−122° (c=5.0, CHCl$_3$), >99% ee, (S)-enantiomer. Spectroscopic data match previously reported data in Krueger et al. (See *J. Am. Chem. Soc.* 121:4284 (1999)).

(R)-2-(benzhydrylamino)-2-(3-bromophenyl)acetonitrile (3p)

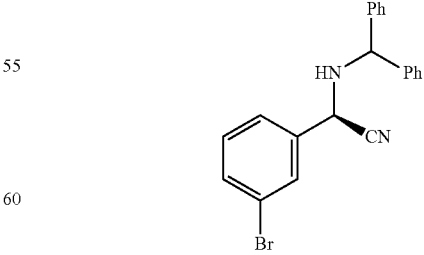

The reaction was run at 0° C. for 20 h with stirring using (E)-N-(3-bromobenzylidene)diphenylmethanamine (350 mg, 1.0 mmol, 1.0 equiv). The product was subjected to purification by flash column chromatography (9:1, hexanes:

Et₂O) to afford (R)-2-(benzhydrylamino)-2-(3-bromophenyl)acetonitrile (365 mg, 0.97 mmol, 97% yield) as a white solid. The enantiomeric excess was determined to be 92% by chiral HPLC analysis (OD-H, 2.0% IPA in hexanes, 1.0 mL/min, 220 nm, $t_R$(major)=13.0 min, $t_R$(minor)=14.6 min); $[\alpha]_D^{24}$=+37.5° (c=1.0, CHCl₃). ¹H NMR (500 MHz, CDCl₃): δ 7.74 (1H, s), 7.59 (2H, t, J=7.5 Hz), 7.50-7.54 (2H, m), 7.47 (2H, d, J=7.5 Hz), 7.41 (2H, t, J=7.5 Hz), 7.30-7.35 (4H, m), 7.25-7.28 (1H, m), 5.26 (1H, s), 4.60 (1H, d, J=12.0 Hz), 2.19 (1H, d, J=11.5 Hz). ¹³C {¹H} NMR (125 MHz, CDCl₃): δ 142.4, 140.7, 136.9, 132.2, 130.4, 130.3, 129.0, 128.8, 128.0, 127.7, 127.4, 127.0, 125.8, 122.9, 118.1, 65.6, 51.7. IR (cm⁻¹): 3314 (m), 3021 (w), 2962 (w), 2852 (w), 2230 (w), 1570 (m), 1493 (m), 1451 (m), 1423 (m), 1072 (m), 880 (m), 787 (s), 753 (s), 700 (s), 680 (s).

(S)-2-(benzhydrylamino)-2-(furan-2-yl)acetonitrile
(3q)

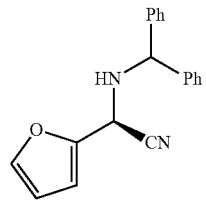 [SMILES: N#C[C@H](NC(c1ccccc1)c1ccccc1)c1ccco1]

The reaction was run at −30° C. for 20 h without stirring using (E)-N-(furan-2-ylmethylene)diphenylmethanamine (261 mg, 1.0 mmol, 1.0 equiv). The product was subjected to purification by flash column chromatography (9:1, hexanes:Et₂O) to afford (S)-2-(benzhydrylamino)-2-(furan-2-yl)acetonitrile (285 mg, 0.99 mmol, 99% yield) as a white solid. The enantiomeric excess was determined to be 93% by chiral HPLC analysis (OD-H, 2.0% IPA in hexanes, 1.0 mL/min, 220 nm, $t_R$(major)=11.2 min, $t_R$(minor)=13.4 min); $[\alpha]_D^{24}$=+32.9° (c=1.0, CHCl₃); lit $[\alpha]_D^{21}$=−25.0° (c=1.0, CHCl₃), 91% ee, (R)-enantiomer. Spectroscopic data match previously reported data in Banphavichit et al. (See *Tetrahedron*, 60:10559 (2004)).

(R)-2-(benzhydrylamino)-2-(furan-3-yl)acetonitrile
(3r)

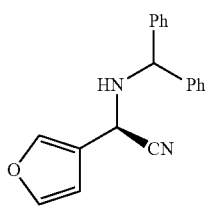 [SMILES: N#C[C@H](NC(c1ccccc1)c1ccccc1)c1ccoc1]

The reaction was run at −30° C. for 20 h without stirring using (E)-N-(furan-3-ylmethylene)diphenylmethanamine (261 mg, 1.0 mmol, 1.0 equiv). The product was subjected to purification by flash column chromatography (9:1, hexanes:Et₂O) to afford (R)-2-(benzhydrylamino)-2-(furan-3-yl)acetonitrile (282 mg, 0.98 mmol, 98% yield) as a white solid. This enantiomeric excess was determined to be 97% by chiral HPLC analysis (OD-H, 2.0% IPA in hexanes, 1.0 mL/min, 220 nm, $t_R$(major)=11.9 min, $t_R$(minor)=12.7 min); $[\alpha]_D^{24}$=+ 64.6° (c=1.0, CHCl₃). ¹H NMR (500 MHz, CDCl₃): δ 7.61 (1H, s), 7.53 (2H, d, J=10.0 Hz), 7.44 (3H, d, J=9.5 Hz), 7.22-7.38 (6H, m), 6.54 (1H, s), 5.21 (1H, s), 4.51 (1H, d, J=15.0 Hz), 2.12 (1H, d, J=15.0 Hz). ¹³C {¹H} NMR (125 MHz, CDCl₃): δ 144.0, 142.6, 140.9, 140.4, 129.0, 128.8, 128.0, 127.7, 127.3, 127.0, 120.9, 118.4, 109.2, 65.3, 44.6. IR (cm⁻¹): 3295 (m), 3135 (w), 3061 (w), 2842 (w), 2231 (w), 1596 (w), 1492 (m), 1474 (m), 1451 (m), 1162 (m), 1102 (m), 1025 (m), 902 (m), 874 ( ), 807 (m), 744 (s), 699 (s).

(S)-2-(benzhydrylamino)-2-(thiophen-2-yl)acetonitrile
(3s)

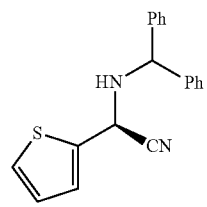 [SMILES: N#C[C@H](NC(c1ccccc1)c1ccccc1)c1cccs1]

The reaction was run at 0° C. for 20 h with stirring using (E)-diphenyl-N-(thiophen-2-ylmethylene)methanamine (277 mg, 1.0 mmol, 1.0 equiv). The product was subjected to purification by flash column chromatography (9:1, hexanes:Et₂O) to afford (S)-2-(benzhydrylamino)-2-(thiophen-2-yl)acetonitrile (294 mg, 0.97 mmol, 97% yield) as a white solid. The enantiomeric excess determined to be 95% by chiral HPLC analysis (OD-H, 2.0% IPA in hexanes, 1.0 mL/min, 220 nm, $t_R$(major)=10.0 min, $t_R$(minor)=11.1 min); $[\alpha]_D^{24}$=+ 68.6° (c=1.0, CHCl₃); lit $[\alpha]_D^{24}$=−76.0° (c=1.0, CHCl₃), 98% ee, (S)-enantiomer. ¹H NMR (500 MHz, CDCl₃): δ 7.59 (2H, d, J=8.0 Hz), 7.48 (2H, d, J=8.0 Hz), 7.25-7.41 (8H, m), 7.01-7.02 (1H, m), 5.25 (1H, s), 4.79 (1H, d, J=12.0 Hz), 2.40 (1H, d, J=12.0 Hz). ¹³C {¹H} NMR (125 MHz, CDCl₃): δ 142.4, 140.7, 138.2, 129.0, 128.8, 128.0, 127.7, 127.2, 127.0, 126.8, 126.6, 126.0, 118.1, 65.3, 48.1. IR (cm⁻¹): 3295 (m), 3104 (w), 3083 (w), 3059 (w), 3023 (w), 2842 (w), 2230 (w), 1491 (m), 1474 (m), 1451 (m), 1188 (m), 1095 (m), 1025 (m), 915 (m), 843 (m), 744 (m), 725 (m), 698 (s).

(R)-2-(benzhydrylamino)-2-cyclohexenylacetonitrile
(3t)

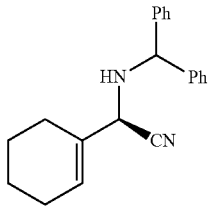 [SMILES: N#C[C@H](NC(c1ccccc1)c1ccccc1)C1=CCCCC1]

The reaction was run at −30° C. for 20 h without stirring using (E)-N-(cyclohexenylmethylene)diphenylmethanamine (263 mg, 1.0 mmol, 1.0 equiv). The product was purified by flash column chromatography (9:1, hexanes:Et₂O) to afford (R)-2-(benzhydrylamino)-2-cyclohexenylacetonitrile (298 mg, 0.99 mmol, 99% yield) as a clear colorless oil. The enantiomeric excess was determined to be 95% ee by chiral HPLC analysis (AD-H, 3.0% IPA in hexanes, 1.0 mL/min, 210 nm, $t_R$(major)=11.2 min, $t_R$(minor)=20.2 min); $[\alpha]_D^{23}$=+

65.4° (c=1.0, CHCl₃). ¹H NMR (500 MHz, CDCl₃): δ 7.53 (2H, d, J=7.0 Hz), 7.46 (2H, d, J=7.5 Hz), 7.32-7.40 (4H, m), 7.24-7.30 (2H, m), 6.06 (1H, d, J=1.5 Hz), 5.17 (1H, s), 3.89 (1H, d, J=8.0 Hz), 2.37-2.41 (1H, m), 2.08-2.12 (2H, m), 1.97-2.01 (1H, m), 1.86 (1H, d, J=9.5 Hz), 1.71 (2H, p, J=6.0 Hz), 1.62 (2H, apparent sextet, J=5.7 Hz). ¹³C {¹H} NMR (125 MHz, CDCl₃): δ 143.0, 141.3, 131.9, 128.8, 128.0, 128.3, 127.6, 127.5, 127.4, 127.1, 126.8, 118.6, 65.2, 54.2, 25.9, 24.9, 22.4, 21.8. IR (cm⁻¹): 3313 (w), 3062 (w), 3029 (w), 2928 (m), 2858 (w), 2228 (w), 1493 (m), 1452 (m), 1076 (m), 1028 (m), 896 (m), 843 (m), 745 (s), 701 (s), 678 (s).

(R,E)-2-(benzhydrylamino)-3-methylhex-3-enenitrile (3u)

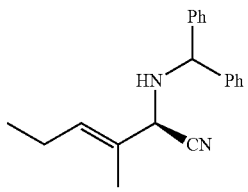 [SMILES: CC/C=C(\C)[C@H](C#N)NC(c1ccccc1)c1ccccc1]

The reaction was run at −30° C. for 20 h without stirring using (E)-N-((E)-2-methylpent-2-enylidene)diphenylmethanamine (263 mg, 1.0 mmol, 1.0 equiv). The product was subjected to purification by flash column chromatography (9:1, hexanes:Et₂O) to afford (R,E)-2-(benzhydrylamino)-3-methylhex-3-enenitrile (286 mg, 0.98 mmol, 98% yield) as a clear colorless oil. The enantiomeric excess was determined to be 91% ee by chiral HPLC analysis (AD-H, 1.0% IPA in hexanes, 1.0 mL/min, 220 nm, t_R(major)=9.4 min, t_R(minor)= 8.5 min); [α]_D²³=+66.9° (c=1.0, CHCl₃). ¹H NMR (500 MHz, CDCl₃): δ 7.50-7.52 (2H, m), 7.44-7.45 (2H, m), 7.23-7.37 (6H, m), 5.74 (1H, dt, J=1.0, 6.5 Hz), 5.13 (1H, s), 3.88 (1H, s), 2.08-2.11 (2H, m), 1.86-1.90 (1H, m), 1.80 (3H, s), 0.98-1.02 (3H, m). ¹³C {¹H} NMR (125 MHz, CDCl₃): δ 142.9, 141.4, 132.0, 128.8, 128.7, 128.4, 127.7, 127.5, 127.4, 127.1, 118.7, 65.2, 55.2, 21.2, 13.9, 13.6. IR (cm⁻¹): 3313 (w), 3062 (w), 3028 (w), 2965 (w), 2932 (w), 2873 (w), 2228 (w), 1493 (m), 1453 (m), 1306 (w), 1189 (w), 1080 (w), 911 (w), 864 (w), 745 (s), 699 (s).

(R,E)-2-(benzhydrylamino)-4-phenylbut-3-enenitrile (3v)

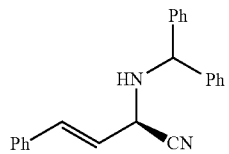

The reaction was run at −30° C. for 20 h with stirring (the reaction mixture was heterogenous) using (E)-diphenyl-N-((E)-3-phenylallylidene)methanamine (297 mg, 1.0 mmol, 1.0 equiv). The product was subjected to purification by flash column chromatography (9:1, hexanes:Et₂O) to afford (R,E)-2-(benzhydrylamino)-4-phenylbut-3-enenitrile (323 mg, 0.99 mmol, 99% yield) as a white solid. The enantiomeric excess was determined to be 95% ee by chiral HPLC analysis (AD-H, 3.0% IPA in hexanes, 1.0 mL/min, 210 nm, t_R (major)=13.2 min, t_R(minor)=19.9 min); [α]_D²³=+13.8° (c=1.0, CHCl₃). ¹H NMR (500 MHz, CDCl₃): δ 7.56 (2H, d, J=8.0 Hz), 7.49 (2H, d, J=7.5 Hz), 7.26-7.44 (11H, m), 6.94 (1H, d, J=16.5 Hz), 6.25 (1H, dd, J=5.0, 16.0 Hz), 5.25 (1H, s), 4.26 (1H, br s), 2.03 (1H, br s). ¹³C {¹H} NMR (125 MHz, CDCl₃): δ 143.1, 141.3, 135.6, 134.1, 129.3, 129.1, 129.0, 128.9, 128.2, 128.0, 127.7, 127.4, 127.1, 122.7, 118.6, 65.6, 50.4. IR (cm⁻¹): 3304 (m), 3056 (w), 3027 (w), 2235 (w), 1492 (m), 1452 (m), 1312 (w), 1108 (m), 963 (m), 743 (s), 702 (s), 695 (s).

(R,E)-2-(benzhydrylamino)hept-3-enenitrile (3w)

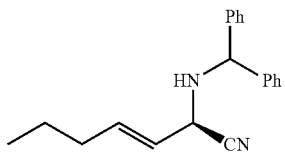 [SMILES: CCC/C=C/[C@H](C#N)NC(c1ccccc1)c1ccccc1]

The reaction was run at −30° C. for 20 h using (E)-N-((E)-hex-2-enylidene) diphenylmethanamine (263 mg, 1.0 mmol, 1.0 equiv). The product was subjected to purification by flash column chromatography (9:1, hexanes:Et₂O) to afford (R,E)-2-(benzhydrylamino)hept-3-enenitrile (281 mg, 0.97 mmol, 97% yield, ~95% purity) as a clear colorless oil. The enantiomeric excess was determined to be 73% by chiral HPLC analysis (OD-H, 2.0% IPA in hexanes, 1.0 mL/min, 220 nm, t_R(major)=7.9 min, t_R(minor)=12.2 min); [α]_D²³=+36.2° (c=1.0, CHCl₃). ¹H NMR (500 MHz, CDCl₃): δ 7.49 (2H, d, J=6.8 Hz), 7.43 (2H, d, J=7.2 Hz), 7.20-7.36 (6H, m), 5.99-6.07 (1H, m), 5.51-5.57 (1H, m), 5.16 (1H, s), 4.00-4.04 (1H, m), 2.07 (2H, q, J=7.2 Hz), 1.85 (1H, d, J=12.0 Hz), 1.43 (2H, apparent sextet, J=7.6 Hz), 0.92 (3H, t, J=7.4 Hz). ¹³C {¹H} NMR (125 MHz, CDCl₃): δ 142.9, 141.2, 135.7, 128.9, 128.7, 127.7, 127.6, 127.4, 127.1, 123.4, 118.6, 65.3, 49.9, 34.0, 21.9, 13.6. IR (cm⁻¹): 3314 (w), 3062 (w), 3028 (w), 2959 (w), 2930 (w), 2872 (w), 2228 (w), 1599 (w), 1493 (m), 1453 (m), 1305 (w), 1079 (w), 1028 (w), 967 (m), 744 (s), 698 (s).

Preparation of Amino Acids

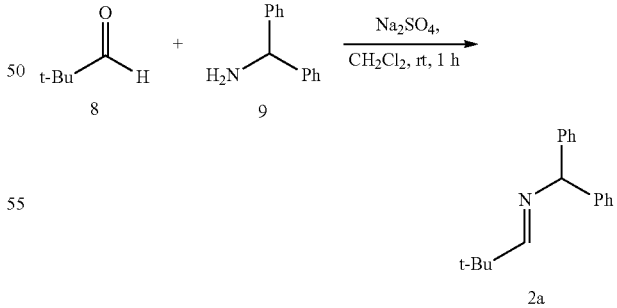

Method A: A 100-mL round-bottomed flask containing a stir bar was charged with Na₂SO₄ (8.0 g) and CH₂Cl₂ (40 mL). Trimethylacetaldehyde (8) (7.65 mL, 52 mmol, 1.3 equiv) and aminodiphenylmethane (9) (6.89 mL, 40 mmol, 1.0 equiv) were added sequentially via syringe while stirring. The flask was capped with a plastic stopper, and the mixture was stirred at room temperature. The mixture became cloudy after 5 min. After stirring for 1 h, the solution was decanted into a 200-mL round-bottomed flask, rinsing with $CH_2Cl_2$ (4×5 mL) and concentrated to 8-10 mL using a rotary evaporator. The flask was then maintained at 1 torr for 10 min. A 5-cm diameter fritted disk funnel was filled with a 2-cm high layer of silica gel. The funnel was rinsed with a solution of 20:1:0.5 hexanes/$Et_2O$/triethylamine (50 mL) under reduced pressure, followed by a solution of 20:1 hexanes/$Et_2O$ (50 mL). The oil prepared above was dissolved in 20:1 hexanes/$Et_2O$ (25 mL) and rinsed through the frit into a tared 250-mL round-bottomed flask under reduced pressure, rinsing with 20:1 hexanes/$Et_2O$ (4×25 mL). The mixture was concentrated (30 torr→1 torr) to provide a clear, pale yellow oil that solidified into a white solid. The solid was broken up into approximately 1-cm diameter pieces using a spatula, and was maintained at 1 torr for another 15 min to provide N-(2,2-dimethyl propylidene)diphenylmethanamine (2a) as a white solid in approximately 98% $^1$H-NMR purity. The product was used in the next step without further purification. Yield: 9.93 g (39.6 mmol, 99%).

Method B: A 100-mL round-bottomed flask containing a stir bar was charged with $Na_2SO_4$ (8.0 g) and $CH_2Cl_2$ (40 mL). Trimethylacetaldehyde (8) (7.65 mL, 52 mmol, 1.3 equiv) and aminodiphenylmethane (9) (6.89 mL, 40 mmol, 1.0 equiv) were added sequentially via syringe while stirring. The flask was capped with a plastic stopper, and the mixture was stirred at room temperature. The mixture became cloudy after 5 min. After stirring for 1 h, the mixture was decanted into a 200 mL round-bottomed flask, rinsing with $CH_2Cl_2$ (4×5 mL), and concentrated to 8-10 mL using a rotary evaporator. The flask was then maintained at 1 torr for 10 min. The resulting pale yellow solid was taken up in $CH_2Cl_2$ (50 mL), transferred to a 250-mL separatory funnel, and washed with $NaHCO_3$ (50 mL). The organic layer was dried over $Na_2SO_4$, filtered through a medium porosity fitted disk funnel into a 200-mL round-bottomed flask, and concentrated in vacuo (30 torr→1 torr) to provide a pale yellow oil that solidified to a white solid within 5 min at 1 torr. The solid was broken up into approximately 1-cm diameter pieces using a spatula, and was maintained at 1 torr for another 15 min to provide N-(2,2 dimethylpropylidene) diphenylmethanamine (2a) as a white solid in approximately 98% $^1$H-NMR purity. The product was used in the next step without further purification. Yield: 9.79 g (38.9 mmol, 97%).

and toluene (76 mL), capped with a virgin rubber septum, and cooled at 0° C. for 10 min under $N_2$. Acetic acid (2.75 mL, 48 mmol, 1.2 equiv) and water (2.88 mL, 160 mmol, 4.0 equiv) were added sequentially via syringe, and the $N_2$ inlet was removed. The resulting white, heterogeneous mixture was stirred vigorously at 0° C. After 5 min the upper organic layer had become a clear, colorless solution, and the lower aqueous layer contained a chunky, white precipitate. After stirring for 20 min, the $N_2$ inlet was restored, and a freshly prepared stock solution of N-(2,2-dimethylpropylidene)diphenylmethanamine (2a) (approximately 40 mmol, prepared via either Method A or B) and 4e (116 mg, 0.20 mmol, 0.0050 equiv) in toluene (24 mL) was added via syringe in 10-mL portions over 1 min. The flask containing the stock solution was rinsed with additional toluene (2×3 mL), and the rinses were added to the reaction. The $N_2$ inlet was removed, and the mixture was stirred at 0° C. After 4 h, the reaction mixture was allowed to warm to room temperature over 5 min. The septum was removed, and the reaction mixture was treated with 50 mL of a 0.2 g/mL aqueous $K_2CO_3$ solution. The mixture was transferred to a 250-mL separatory funnel in a fume hood, the reaction flask was rinsed with $Et_2O$ (3×5 mL), and the rinses were added to the separatory funnel. The organic and aqueous layers were thoroughly mixed, and the aqueous layer removed. The organic layer was washed with another 50 mL of $K_2CO_3$ solution and brine (50 mL). The clear, colorless organic layer was dried over $Na_2SO_4$, decanted into a 500-mL round-bottomed flask, rinsing with $Et_2O$ (3×5 mL), and concentrated to a volume of approximately 100 mL using a rotary evaporator. The flask was then charged with a 2-cm long stir bar, placed in a 25° C. water bath, and concentrated to a volume of approximately 15 mL by vacuum transfer into a −78° C. bath. A sample of the clear, colorless liquid residue was analyzed by chiral HPLC analysis (AS-H, 1 mL/min, 5% IPA/hexanes, 220 nm): $t_R$(minor)=6.18 min, $t_R$(major)=9.09 min, 87-88% ee (range of three experiments). The liquid was transferred to a 100-mL round-bottomed flask, rinsing with $CH_2Cl_2$ (3×4 mL). The solution was concentrated to a mass of 12 g under reduced pressure (30 torr→1 torr). The crude (R)-2-(benzhydrylamino)-3,3-dimethylbutanenitrile was used in the next step without further purification.

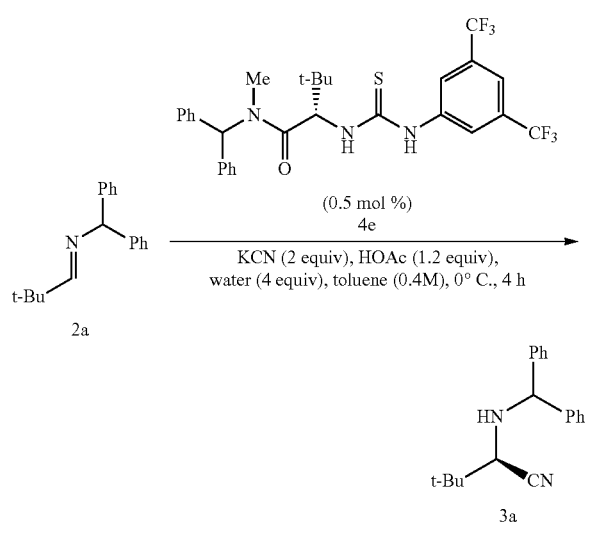

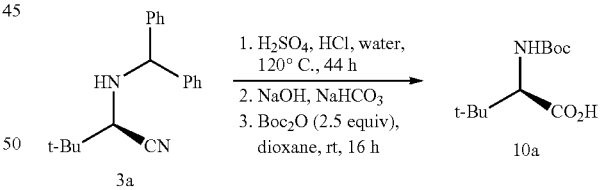

Scheme 5:

A 250-mL round-bottomed flask containing a 4-cm long stir bar was charged with KCN (5.21 g, 80 mmol, 2.0 equiv)

The 100-mL round-bottomed flask containing (R)-2-(benzhydrylamino)-3,3-dimethylbutanenitrile was charged with a 2-cm long stir bar. A solution of 40 mL of aqueous HCl/$H_2SO_4$ solution was generated as follows: a 50-mL Erlenmeyer flask was charged with deionized water (20 mL) and cooled in an ice bath for 5 min. Concentrated hydrochloric acid (8 mL) was added over 1 min, followed by concentrated sulfuric acid (12 mL) over 5 min (in 2-mL portions). The flask was swirled gently and was allowed to cool in the ice bath for 5 min. The solution was then added to the flask containing the α-aminonitrile in one portion, and the flask was fitted with a chilled reflux condenser. The flask was placed in an oil bath that was maintained at 120° C., and reaction mixture was stirred for 44 h.

The reaction mixture was allowed to cool to room temperature and was then cooled for 2 min in an ice bath. Water (25 mL) and Et$_2$O (25 mL) were carefully added over 2 min, and the entire contents of the flask were poured into a 250-mL separatory funnel. The flask was rinsed with another 25-mL portion of diethyl ether and another 5-mL portion of water, and the mixture was added to the separatory funnel. The organic and aqueous layers were thoroughly mixed, and the aqueous layer was removed. The organic layer was further extracted with water (25 mL), and the combined aqueous layers were cooled for 5 min in an ice bath within a 250-mL Erlenmeyer flask. Aqueous NaOH (4N) was added in 10-20-mL portions over 5 min with stirring until pH 11 was reached, as determined by pH paper (approximately 120 mL total). The resulting mixture was transferred to a 500-mL separatory funnel and washed with diethyl ether (2×50 mL). The aqueous layer was transferred to a 500-mL Erlenmeyer flask containing a 4-cm long stirbar, acidified to pH 9.5-10.5 by addition of solid NaHCO$_3$ (1 g), and cooled in an ice bath for 3 min with stirring. Dioxane (100 mL) was added, followed immediately by Boc$_2$O (22 g, 100 mmol, 2.5 equiv) in one portion. The flask was covered with Parafilm and allowed to warm to room temperature with stirring. The stir-rate was adjusted to ensure thorough mixing of the upper organic layer and the lower aqueous layer, and the mixture was stirred at that rate for 14 h. Concentrated HCl was then added to the stirring mixture in 1-mL portions over 5 min until pH 2 was reached (10 mL total). The mixture was transferred to a 500-mL separatory funnel and extracted with Et$_2$O (3×100 mL). The combined organic layers were dried over Na$_2$SO$_4$, decanted into a 500-mL round-bottomed flask, and concentrated under reduced pressure (30 torr→1 torr). Benzene was added (2×20 mL), and the resulting solution was concentrated under reduced pressure (30 torr→1 torr) to yield 14-16 g of a pale yellow, cloudy oil. The residue was partitioned between 1N aqueous NaOH (100 mL) and Et$_2$O (75 mL) and then transferred to a 250-mL separatory funnel. The round-bottomed flask was rinsed with two 10-mL portions of 1N aqueous NaOH that were added to the separatory funnel. The organic layer was removed, and the aqueous layer was washed with another 75 mL of Et$_2$O.

The aqueous layer was transferred to a 250-mL Erlenmeyer flask and cooled in an ice bath for 2 min. Aqueous HCl (4N) was added in 10-mL portions over 5 min until pH 2 was reached (40 mL total). A white precipitate formed after 35 mL of HCl had been added. The aqueous layer was extracted with diethyl ether (3×75 mL), and the combined organic layers were dried over Na$_2$SO$_4$, decanted into a 500-mL round-bottomed flask, and concentrated under reduced pressure (30 torr→1 torr) to yield a white foamy solid. Hexanes (20 mL) was added to the flask, and the resulting mixture concentrated under reduced pressure. The process was repeated twice to yield a white powder that was maintained at 1 torr for 2 h. Yield: 7.04-7.51 g (30.4-32.5 mmol, 76-81% yield from aminodiphenylmethane, range of three experiments). The enantiomeric excess was determined to be 85-86% by HPLC analysis of the benzyl ester (range of three experiments). The crude product was heated in a solution of 230-240 mL 2:1 hexanes/Et$_2$O (32 mL/g) for ~2 min. Complete dissolution did not occur. A 5-cm long stirbar was then added, the flask was capped with a plastic stopper, and the mixture was stirred at 0° C. for 2 h. The mixture was filtered through a medium porosity fritted disk funnel, and the filtrate was concentrated under reduced pressure to yield a white foamy solid. Hexanes (20 mL) was added, and the resulting mixture was concentrated to provide a white solid. Pentane (20 mL) was added, and the resulting mixture was concentrated to provide a white solid that was maintained at 1 torr for 16 h to provide (R)-Boc-tert-leucine as a white solid: 5.76-6.03 g (24.9-26.1 mmol, 62-65% yield from aminodiphenylmethane, range of three experiments). The enantiomeric excess of the filtrate was determined to be 98-99% by HPLC analysis of the benzyl ester (range of three experiments); mp: 117-120° C. to 118-121° C. $[\alpha]_D^{25}$=−5.3° (c 1.5, EtOAc). lit. $[\alpha]_D^{25}$=+5.8 (c 0.6, EtOAc, (S)-enantiomer). The compound is a 6:1 mixture of carbamate rotamers in CDCl$_3$; resonances corresponding to the minor rotamer are indicated with a * (many resonances for the minor rotamer are indistinguishable from those reported for the major rotamer, and are not reported). $^1$H NMR (500 MHz, CDCl$_3$, 25° C.), δ 5.82 (1H, br s)*, 5.07 (1H, d, J=9 Hz), 4.12 (1H, d, J=9.5 Hz), 3.90 (1H, br s)*, 1.45 (9H, s), 1.02 (9H, s). $^{13}$C NMR (126 MHz, CDCl$_3$, 25° C.): δ 177.0, 156.8*, 155.8, 81.7*, 80.1, 63.8*, 61.8, 34.6, 34.1*, 28.5, 26.7. IR (cm$^{-1}$): 3434 (br w), 3309 (w), 3169 (w), 2972 (m), 1740 (m), 1706 (s), 1686 (s), 1640 (s), 1507 (m), 1411 (s), 1368 (m), 1259 (w), 1233 (m), 1211 (w), 1156 (s), 1056 (m), 1008 (m), 650 (m), 777 (w), 690 (m). LRMS (ESI): 254.1 (70%) [M+Na].

Preparation of (R)-benzyl 2-(tert-butoxycarbonylamino)-3,3-dimethylbutanoate for chiral HPLC analysis (11a)

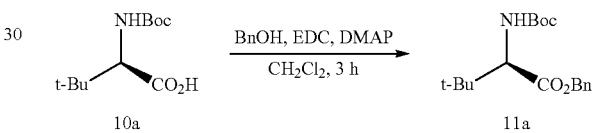

A 2-dram vial containing a small stirbar was charged with Boc-tert-leucine (10a) (10 mg, 0.04 mmol), CH$_2$Cl$_2$ (1 mL), 4-dimethylaminopyridine (2 mg, 0.02 mmol, 0.5 equiv), benzyl alcohol (20 µL, 0.2 mmol, 5 equiv), and EDC (20 mg, 0.1 mmol, 2.5 equiv). The solution was stirred at room temperature for 3 h, and then diluted with 10 mL of diethyl ether. The mixture was washed with water (2×10 mL), saturated aqueous NaHCO$_3$ (10 mL), and brine (10 mL). The organic layer was dried over Na$_2$SO$_4$ and concentrated under reduced pressure. The residue can be further purified by flash column chromatography on silica gel (7:1 hexanes/Et$_2$O). Both the crude and purified samples were analyzed by chiral HPLC analysis: (AD-H, 1 mL/min, 5% IPA/hexanes, 210 nm): t$_R$(major)=9.08 min, t$_R$(minor)=15.80 min.

(R)-2-(tert-butoxycarbonylamino)-2-(1-methylcyclohexyl)acetic acid (13)

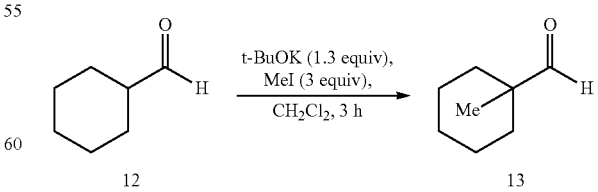

A flame-dried 500-mL round-bottomed flask capped with a rubber septum was charged with anhydrous CH$_2$Cl$_2$ (150 mL) via cannula and cyclohexanecarboxaldehyde (12) (9.09 mL, 75 mmol, 1.0 equiv) via syringe under N$_2$. The flask was cooled in an ice bath for 10 min, the septum was removed, and t-BuOK (10.9 g, 97.5 mmol, 1.3 equiv) was added in one portion with rapid stirring. The septum was replaced, and iodomethane (14.0 mL, 225 mmol, 3.0 equiv) was added in one portion via syringe. The mixture was stirred at 0° C. under $N_2$ for 30 min. The mixture was then allowed to warm to room temperature and stirred an additional 2 h. The resulting pale yellow, heterogeneous mixture was filtered through a 10-cm diameter medium porosity fritted disk funnel, and the cake was washed with $CH_2Cl_2$ (3×15 mL). The filtrate was washed with brine (50 mL). The organic layer was dried over $Na_2SO_4$ and concentrated under reduced pressure. The residue was distilled under reduced pressure (1 torr) while maintaining the receiving flask between −20 to −40° C. (bp <30° C.). The distillate was a clear, colorless oil that contained (1-methyl)cyclohexanecarboxaldehyde (13) and 1.25 equiv $CH_2Cl_2$, as determined by $^1$H-NMR analysis: 13.2 g total, ~7.2 g (1-methyl)cyclohexanecarboxaldehyde (57 mmol, 76% yield). The product was used in the next step without further purification.

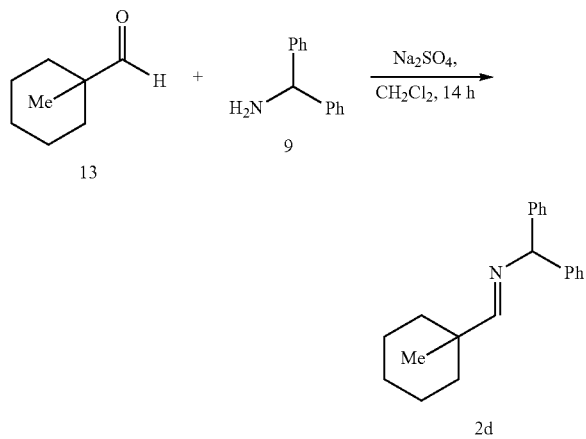

A 100-mL round-bottomed flask containing (1-methyl)cyclohexanecarboxaldehyde (13) (57 mmol) was charged with $CH_2Cl_2$ (20 mL), $Na_2SO_4$ (10 g), and aminodiphenylmethane (9) (8.83 mL, 51.3 mmol, 0.9 equiv). The flask was capped with a plastic stopper, and the mixture was stirred at room temperature for 14 h. The reaction mixture was filtered through a medium porosity fritted disk funnel, rinsing with $CH_2Cl_2$ (4×10 mL). The filtrate was concentrated under reduced pressure and maintained at 1 torr with stirring for 1 h to provide a slightly cloudy, colorless oil. A 5-cm diameter fritted disk funnel was filled with a 3-cm high layer of silica gel. The funnel was rinsed with a solution of 20:1:0.5 hexanes/diethyl ether/triethylamine (50 mL) under reduced pressure, followed by a solution of 20:1 hexanes/diethyl ether (50 mL). The oil prepared above was dissolved in 20:1 hexanes/diethyl ether (25 mL) and rinsed through the frit into a 250-mL round-bottomed flask under reduced pressure.

The silica gel was rinsed with 20:1 hexanes/diethyl ether (4×25 mL). The combined mixture was concentrated (30 torr→1 torr) to provide a clear, colorless oil that was slightly cloudy. The oil was maintained at 1 torr for 1 h with stirring to provide (E)-N-((1-methylcyclohexyl)methylene)diphenylmethanamine as a colorless oil with 95% $^1$H-NMR purity. Yield: 14.3 g (49.0 mmol, 96% from aminodiphenylmethane, 65% from cyclohexanecarboxaldehyde).

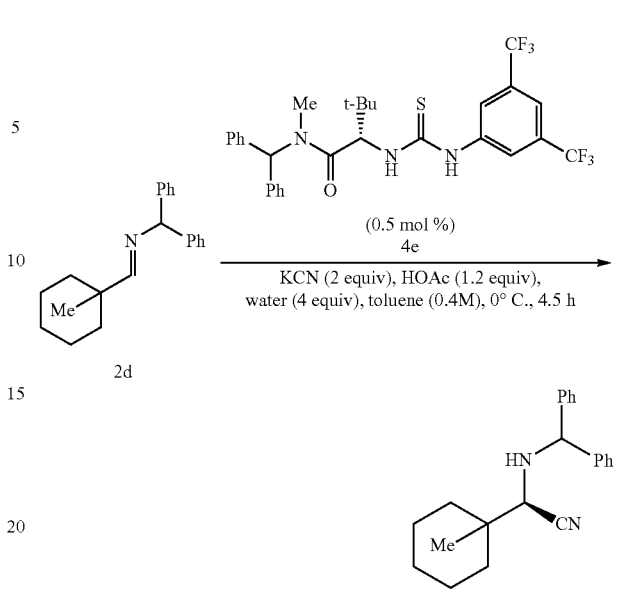

A 250-mL round-bottomed flask containing a 4-cm long stir bar was charged with KCN (3.26 g, 50 mmol, 2.0 equiv) and toluene (48 mL), capped with a virgin rubber septum, and cooled at 0° C. for 10 min under $N_2$. AcOH (1.72 mL, 30 mmol, 1.2 equiv) and water (1.80 mL, 100 mmol, 4.0 equiv) were added sequentially via syringe, and the $N_2$ inlet was removed. The resulting white, heterogeneous mixture was stirred vigorously at 0° C. After 5 min the upper organic layer had become a clear, colorless solution, and the lower aqueous layer contained a chunky, white precipitate. After stirring for 20 min, the $N_2$ inlet was restored, and a freshly prepared stock solution of (E)-N-((1-methylcyclohexyl)methylene)diphenylmethanamine (2d) (7.29 g, 25 mmol, 1.0 equiv) and 4e (73 mg, 0.125 mmol, 0.0050 equiv) in toluene (15 mL) was added via syringe over 1 min. The flask containing the stock solution was rinsed with additional toluene (2×2 mL), and the rinses were added to the reaction mixture. The $N_2$ inlet was removed, and the mixture was stirred at 0° C. After 4.5 h, the reaction mixture was allowed to warm to room temperature over 5 min. The septum was removed, and the reaction mixture was treated with 50 mL of a 0.2 g/mL aqueous $K_2CO_3$ solution. The mixture was transferred to a 250-mL separatory funnel, the reaction flask was rinsed with $Et_2O$ (3×5 mL), and the rinses were added to the separatory funnel. The organic and aqueous layers were thoroughly mixed, and the aqueous layer removed. The organic layer was washed with another 50 mL of $K_2CO_3$ solution and brine (50 mL). The clear, colorless organic layer was dried over $Na_2SO_4$, decanted into a 500-mL round-bottomed flask, rinsing with $Et_2O$ (3×5 mL), and concentrated to a volume of 70 mL using a rotary evaporator. The flask was then charged with a 2-cm long stir bar, placed in a 25° C. water bath, and concentrated to a volume of approximately 10 mL by vacuum transfer into a −78° C. bath. A sample of the clear, colorless liquid residue was analyzed by chiral HPLC analysis (AD-H, 1 mL/min, 5% IPA/hexanes, 220 nm), $t_R$(minor)=5.18 min, $t_R$(major)=5.81 min., 89-90% ee (range of two experiments). The liquid was transferred to a 200-mL round-bottomed flask, rinsing with $CH_2Cl_2$ (3×4 mL). The solution was concentrated under reduced pressure (~30 torr→1 torr). The resulting viscous oil was dissolved in $CH_2Cl_2$ (2×20 mL), and the resulting solution concentrated under reduced pressure (~30 torr→1 torr) to a mass of 8.6-8.7 g. The crude (R)-2-(benzhydrylamino)-2-(1-methylcyclohexyl)acetonitrile (3d) was used in the next step without further purification.

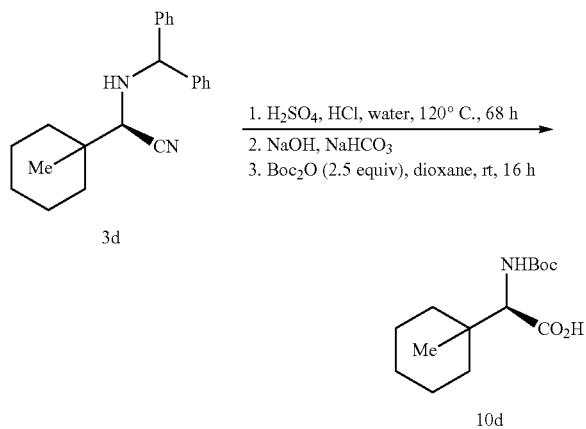

The 200-mL round-bottomed flask containing (R)-2-(benzhydrylamino)-3,3-dimethylbutanenitrile (3d) was charged with a 4-cm long stirbar. A solution of 60 mL of aqueous 3:1 HCl/H$_2$SO$_4$ solution was generated as follows: a 125-mL Erlenmeyer flask was charged with deionized water (30 mL) and cooled in an ice bath for 5 min. Concentrated hydrochloric acid (7.5 mL) was added over 1 min, followed by concentrated sulfuric acid (22.5 mL) over 5 min (in 2-mL portions). The flask was swirled gently, and was allowed to further cool in the ice bath for 5 min. The solution was then added to the flask containing the α-aminonitrile in one portion, and the flask was fitted with a chilled reflux condenser. The flask was placed in an oil bath that was maintained at 120° C., and reaction mixture was stirred for 68 h. The flask was cooled to room temperature to yield a dark brown mixture, and then further cooled for 2 min in an ice bath. Water (50 mL) and diethyl ether (50 mL) were carefully added over 2 min to provide a black upper organic layer and an orange lower aqueous layer. The entire contents of the flask were poured into a 500-mL separatory funnel. The flask was rinsed with another 50-mL portion of diethyl ether and another 50-mL portion of water, and the mixture was added to the separatory funnel. The organic and aqueous layers were thoroughly mixed, and the aqueous layer was removed. The aqueous layer was further washed with diethyl ether (50 mL), and the combined aqueous layers were cooled for 5 min in an ice bath within a 1-L Erlenmeyer flask. Aqueous NaOH (4N) was added in 10-20-mL portions over 5 min with stirring until pH 10-11 was reached, as determined by pH paper (approximately 190 mL total). The resulting mixture was transferred to a 1-L separatory funnel and washed with diethyl ether (3×50 mL). The aqueous layer was transferred to a 1-L Erlenmeyer flask containing a 5-cm long stirbar, acidified to pH 9.5-10.5 by addition of solid NaHCO$_3$ (1 g), and cooled in an ice bath for 3 min with stirring.

Dioxane (100 mL) was added to the mixture prepared above, followed immediately by Boc$_2$O (16.4 g, 75 mmol, 3.0 equiv) in one portion. The flask was covered with Parafilm and allowed to warm to room temperature with stirring. The stir-rate was adjusted to ensure thorough mixing of the upper organic layer and the lower aqueous layer, and the mixture was stirred at that rate for 14 h. After 14 h, the pH 7 was reached. Concentrated HCl was carefully added to stirring mixture in 1-mL portions over 5 min until pH 2 was reached, as determined using pH paper (10 mL total). The mixture was transferred to a 1-L separatory funnel and extracted with Et$_2$O (3×100 mL). The aqueous layer was viscous but free-flowing, and the organic layer was a clear, colorless solution. The combined organic layers were dried over Na$_2$SO$_4$, decanted into a 500-mL round-bottomed flask, and concentrated under reduced pressure (30 torr→1 torr). Benzene was added (3×20 mL), and the resulting solution concentrated under reduced pressure (30 torr→1 torr) to yield 12.5 g of a slightly yellow, cloudy oil. The residue was partitioned between 1N aqueous NaOH (100 mL) and diethyl ether (75 mL) and transferred to a 250-mL separatory funnel. The round-bottomed flask was rinsed with two 10-mL portions of 1N aqueous NaOH that were added to the separatory funnel. The organic layer was removed, and the aqueous layer was washed with another 75 mL diethyl ether.

The aqueous layer was transferred to a 250-mL Erlenmeyer flask and cooled in an ice bath for 2 min. Aqueous HCl (4N) was added in 10-mL portions over 5 min until pH ~2 was reached (40 mL total). A white precipitate formed after 35 mL of HCl solution had been added. The aqueous layer was extracted with diethyl ether (3×75 mL), and the combined clear, colorless organic layers were dried over Na$_2$SO$_4$, decanted into a 500-mL round-bottomed flask, and concentrated under reduced pressure (30 torr→1 torr) to yield a white foamy solid. Benzene (2×20 mL) was added to the flask, and the resulting mixture was concentrated under reduced pressure. The process was repeated with hexanes (4×20 mL) to yield a white powder that was maintained at 1 torr for 1 h. Yield: 4.30-4.33 g (15.8-16.0 mmol, 63-64% yield from imine). The enantiomeric excess was determined to be 87-88% by HPLC analysis of the benzyl ester (range of two experiments).

The crude product was heated in a solution of 170 mL of 3:1 hexanes/Et$_2$O for 2 min. Complete dissolution did not occur. A 5-cm long stirbar was then added, the flask was capped with a plastic stopper, and the mixture was stirred at 0° C. for 2 h. The mixture was filtered through a medium porosity fitted funnel and the filtrate was concentrated under reduced pressure to yield a white foamy solid. Hexanes (3×20 mL) was added, and the resulting mixture was concentrated to provide a white solid. Pentane (20 mL) was added, and the resulting mixture was concentrated to provide a white solid that was maintained at 1 torr for 6 h to provide (R)-2-(tert-butoxycarbonylamino)-2-(1-methylcyclohexyl)acetic acid as a white powder: 3.43-3.52 g (12.6-13.0 mmol, 51-52% yield from imine, range of two experiments); mp 127-130° C. to 128-130° C. The enantiomeric excess of the filtrate was determined to be 98-99% by HPLC analysis of the benzyl ester (see below). $^1$H-NMR analysis revealed ~1 mass % residual hexanes/pentane. $[\alpha]_D^{25}=-15.2°$ (c 1.5, EtOAc). The compound exists as a 10:1 mixture of carbamate rotamers in CDCl$_3$; resonances corresponding to the minor rotamer are indicated with a * (resonances that are indistinguishable from those corresponding to the major rotamer are not reported). $^1$H NMR (500 MHz, CDCl$_3$, 25° C.), δ 5.60 (1H, br s)*, 5.04 (1H, d, J=9 Hz), 4.30 (1H, d, J=9 Hz), 4.08 (1H, br s)*, 1.60-1.32 (10H, m), 1.45 (9H, s), 0.95 (3H, s). $^{13}$C NMR (126 MHz, CDCl$_3$, 25° C.): δ 177.2, 156.7*, 155.8, 81.6*, 80.1, 62.4*, 60.7, 37.2, 36.8*, 34.9, 34.7, 28.5, 26.0, 21.8, 21.7, 20.5. IR (cm$^{-1}$): 3432 (w), 3312 (m), 2935 (m), 1737 (m), 1704 (s), 1640 (m), 1502 (m), 1409 (s), 1367 (m), 1231 (m), 1156 (s), 1026 (m), 844 (m), 777 (w), 685 (m). LRMS (ESI): 294.2 (100%) [M+Na].

Preparation of (R)-benzyl 2-(tert-butoxycarbony-lamino)-2-(1-methylcyclohexyl)acetate for chiral HPLC analysis (11d)

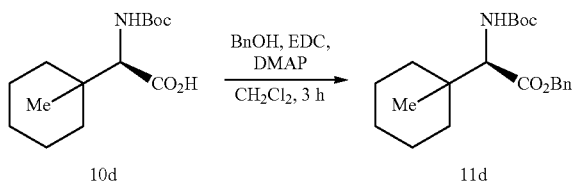

A 2-dram vial containing a small stirbar was charged with (R)-2-(tert-butoxycarbonylamino)-2-(1-methylcyclohexyl) acetic acid (10d) (11 mg, 0.04 mmol), $CH_2Cl_2$ (1 mL), 4-dimethylaminopyridine (2 mg, 0.02 mmol, 0.5 equiv), benzyl alcohol (20 µL, 0.2 mmol, 5 equiv), and EDC (20 mg, 0.1 mmol, 2.5 equiv). The solution was stirred at room temperature for 3 h, and then diluted with 10 mL $Et_2O$. The mixture was washed with water (2×10 mL), saturated aqueous $NaHCO_3$ (10 mL), and brine (10 mL). The organic layer was dried over $Na_2SO_4$ and concentrated under reduced pressure. The residue was purified by flash column chromatography on silica gel (7:1 hexanes/$Et_2O$) and analyzed by chiral HPLC analysis: (AS-H, 1 mL/min, 2% IPA/hexanes, 210 nm): $t_R$(minor)=6.84 min, $t_R$(major)=8.13 min.

(R)-2-(tert-butoxycarbonylamino)-3-ethyl-3-methyl-pentanoic acid (15)

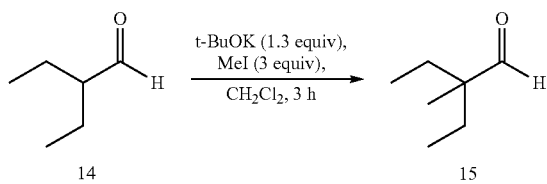

An oven-dried 500-mL round-bottomed flask capped with a rubber septum was charged with anhydrous $CH_2Cl_2$ (250 mL) and 2-ethylbutyraldehyde (14) (12.3 mL, 100 mmol, 1.0 equiv) via syringe under $N_2$. The flask was cooled in an ice bath for 10 min, the septum was removed, and t-BuOK (14.6 g, 130 mmol, 1.3 equiv) was added in one portion with rapid stirring. The septum was replaced, and iodomethane (18.7 mL, 300 mmol, 3.0 equiv) was added in one portion via syringe. The mixture was stirred at 0° C. for 30 min. The mixture was then stirred at room temperature for 2 h. The resulting slightly yellow, heterogeneous mixture was filtered through a 10-cm diameter medium porosity fritted disk funnel, and the cake was washed with $CH_2Cl_2$ (3×15 mL). The filtrate was washed with brine (50 mL). The organic layer was dried over $Na_2SO_4$ and concentrated under reduced pressure. The residue was distilled under reduced pressure (~1 torr) while maintaining the receiving flask between −20 to −40° C. (bp <30° C.). The distillate (13.5 g) was a clear, colorless oil that contained $CH_2Cl_2$ (0.3 equiv) and t-BuOH (0.2 equiv), and was used without further purification. The purity of the compound was assessed by $^1H$ NMR spectroscopy (400 MHz, $CDCl_3$): δ 9.42 (1H, s), 5.30 (0.64H, s, $CH_2Cl_2$), 1.58-1.45 (4H, m), 1.27 (1.97H, s, t-BuOH), 0.98 (3H, s), 0.81 (6H, t, J=8 Hz).

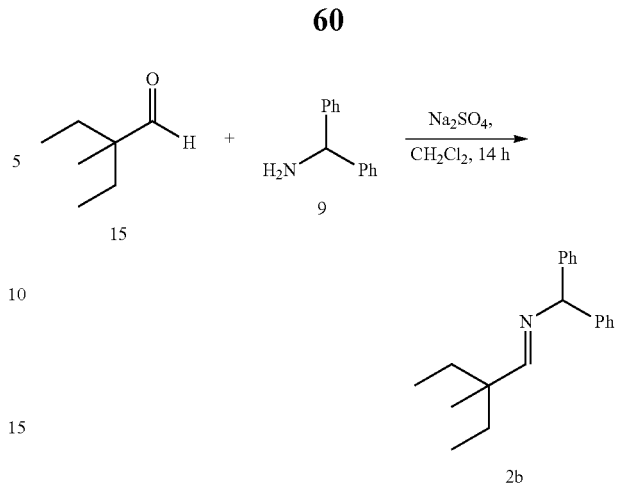

A 100-mL round-bottomed flask containing crude 2-ethyl-2-methylbutanal (15) was charged with $CH_2Cl_2$ (20 mL) and $Na_2SO_4$ (10 g). Aminodiphenylmethane (9) (8.83 mL, 80 mmol, 0.80 equiv) was added via syringe. The flask was capped with a plastic stopper, and the mixture was stirred at room temperature for 14 h. The reaction mixture was filtered through a medium porosity fritted disk funnel and rinsed with $CH_2Cl_2$ (4×10 mL). The filtrate was concentrated under reduced pressure and maintained at 1 torr with stirring for 1 h to provide a slightly cloudy, colorless oil. A 5-cm diameter fritted disk funnel was filled with a 3-cm high layer of silica gel. The funnel was rinsed with a solution of 20:1:0.5 hexanes/$Et_2O$/triethylamine (50 mL) under reduced pressure, followed by a solution of 20:1 hexanes/$Et_2O$ (50 mL). The oil prepared above was dissolved in 20:1 hexanes/$Et_2O$ (25 mL) and rinsed through the frit into a 250-mL round-bottomed flask under reduced pressure, rinsing with 20:1 hexanes/$Et_2O$ (4×25 mL). The mixture was concentrated under reduced pressure (30 torr→1 torr) to provide a clear, colorless oil that was slightly cloudy. The oil was maintained at 1 torr for 1 h while stirring to provide (E)-N-(2-ethyl-2-methylbutylidene) diphenylmethanamine (2b) in 95% $^1H$-NMR purity. Yield: 18.7 g (67 mmol, 84% from aminodiphenylmethane, 67% from 2-ethyl-2-butanal).

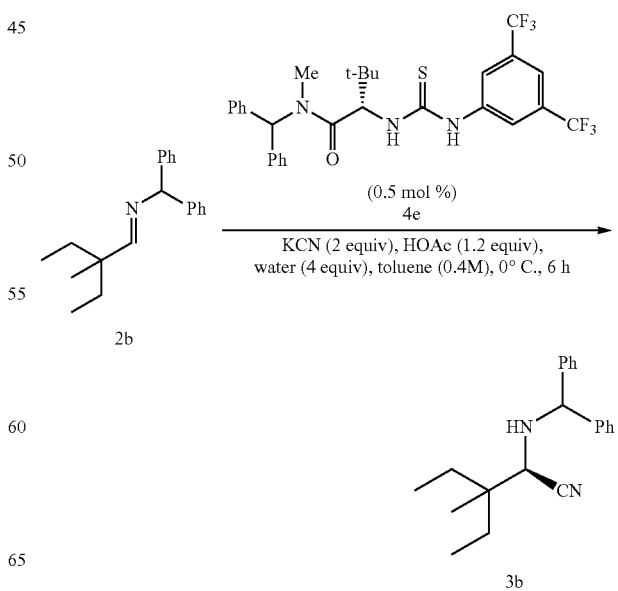

A 250-mL round-bottomed flask containing a 4-cm long stir bar was charged with KCN (3.26 g, 50 mmol, 2.0 equiv) and toluene (48 mL), capped with a virgin rubber septum, and cooled at 0° C. for 10 min under $N_2$. AcOH (1.72 mL, 1.2 equiv, 30 mmol) and water (1.80 mL, 4.0 equiv, 160 mmol) were added sequentially via syringe, and the $N_2$ inlet was removed. The resulting white, heterogeneous mixture was stirred vigorously at 0° C. After 5 min the upper organic layer had become a clear, colorless solution, and the lower aqueous layer contained a chunky, white precipitate. After stirring for 20 min, the $N_2$ inlet was restored, and a freshly prepared stock solution of (E)-N-(2-ethyl-2-methylbutylidene)diphenylmethanamine (2b) (6.90 g, 25 mmol, 1.0 equiv) and 4e (73 mg, 0.125 mmol, 0.0050 equiv) in toluene (15 mL) was added via syringe over 1 min. The stock solution was rinsed with additional toluene (2×2 mL). The $N_2$ inlet was removed, and the mixture was stirred at 0° C. After an additional 6 h, the reaction mixture was allowed to warm to room temperature for 5 min. The septum was removed, and the reaction mixture was treated with 50 mL of a 0.2 g/mL aqueous $K_2CO_3$ solution. The mixture was transferred to a 250-mL seperatory funnel, the reaction flask was rinsed with $Et_2O$ (3×5 mL), and the rinses were added to the reparatory funnel. The organic and aqueous layers were thoroughly mixed, and the aqueous layer removed. The organic layer was washed with another 50 mL of $K_2CO_3$ solution and brine (50 mL). The clear, colorless organic layer was dried over $Na_2SO_4$, decanted into a 500-mL round-bottomed flask, rinsing with $Et_2O$ (3×5 mL), and concentrated at ~30 torr to a volume of approximately 70 mL using a rotary evaporator. The flask was then charged with a 2-cm long stir bar, placed in a 25° C. water bath, and concentrated to a volume of 10 mL by vacuum transfer into a −78° C. bath. A sample of the clear, colorless liquid residue was analyzed by chiral HPLC analysis (AS-H, 1 mL/min, 1% IPA/hexanes, 220 nm): 88% ee. The liquid was transferred to a 200-mL round-bottomed flask, rinsing with $CH_2Cl_2$ (3×4 mL). The solution was concentrated under reduced pressure (~30 torr→1 torr). The residue was dissolved in $CH_2Cl_2$ (2×20 mL), and the resulting solution concentrated under reduced pressure (~30 torr→1 torr) to a mass of 8.5 g of a colorless oil (ca. 90% $^1$H-NMR purity). The crude (S)-2-(benzhydrylamino)-3-ethyl-3-methylpentanenitrile (3b) was used in the next step without further purification.

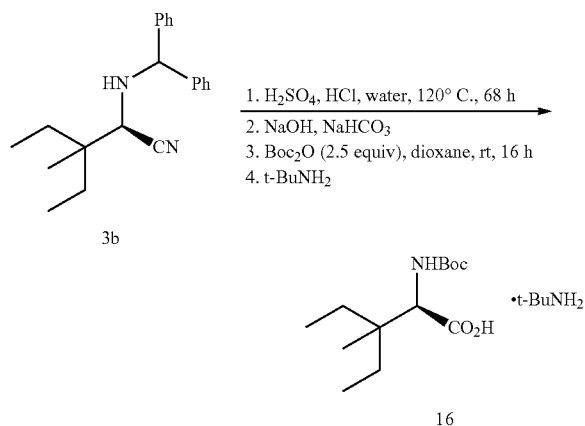

The 200-mL round-bottomed flask containing (R)-2-(benzhydrylamino)-3-ethyl-3-methylpentanenitrile (3b) was charged with a 4-cm long stirbar. A solution of 60 mL of aqueous $HCl/H_2SO_4$ solution was generated as follows: a 125-mL Erlenmeyer flask was charged with deionized water (30 mL) and cooled in an ice bath for 5 min. Concentrated hydrochloric acid (7.5 mL) was added over 1 min, followed by concentrated sulfuric acid (22.5 mL) over 5 min (in 2-mL portions). The flask was swirled gently and was allowed to further cool in the ice bath for 5 min. The solution was then added to the flask containing the α-aminonitrile in one portion, and the flask was fitted with a chilled reflux condenser. The flask was placed in an oil bath that was maintained at 120° C., and reaction mixture was stirred for 68 h.

After 68 h, the flask was cooled to room temperature to yield a dark brown mixture that was further cooled in an ice bath for 2 min. Water (50 mL) and diethyl ether (50 mL) were carefully added over 2 min to provide a dark orange organic layer and a light orange lower aqueous layer. The entire contents of the flask were poured into a 500-mL separatory funnel. The flask was rinsed with another 50-mL portion of diethyl ether and another 50-mL portion of water, and the mixture was added to the separatory funnel. The organic and aqueous layers were thoroughly mixed, and the aqueous layer was removed. The organic layer was further washed with diethyl ether (50 mL), and the combined aqueous layers were cooled for 5 min in an ice bath within a 1-L Erlenmeyer flask. Aqueous NaOH (4N) was added in 10-20-mL portions over 5 min with stirring until pH ~12-13 was reached, as determined by pH paper (190 mL total). The resulting mixture was transferred to a 1-L separatory funnel and washed with diethyl ether (2×50 mL). The aqueous layer was transferred to a 1-L Erlenmeyer flask containing a 5-cm long stirbar, acidified to pH 9.5-10.5 by addition of solid $NaHCO_3$ (1 g), and cooled in an ice bath for 3 min with stirring. Dioxane (100 mL) was added, followed immediately by $Boc_2O$ (16.4 g) in one portion. The mixture became viscous upon addition of dioxane and partially solidified upon addition of $Boc_2O$. The flask was covered with Parafilm and allowed to warm to room temperature while stirring. Upon stirring at room temperature for 30 min, the mixture was viscous but free-flowing. The stir-rate was adjusted to ensure thorough mixing of the upper organic layer and the lower aqueous layer, and the mixture was stirred at that rate for 14 h. After 14 h, the pH 7 was reached. Concentrated HCl was carefully added to stirring mixture in 1-mL portions over 5 min until pH 2 was reached, as determined by pH paper (~10 mL total). The mixture was transferred to a 1-L separatory funnel and extracted with $Et_2O$ (3×100 mL). The aqueous layer was viscous but free-flowing, and the organic layer was a clear, colorless solution. The combined organic layers were dried over $Na_2SO_4$, decanted into a 500-mL round-bottomed flask, and concentrated under reduced pressure (30 torr→1 torr). Benzene was added (3×20 mL), and the resulting solution was concentrated under reduced pressure (30 torr→1 torr) to yield 10 g of viscous yellow solid. The residue was partitioned between 1N aqueous NaOH (100 mL) and diethyl ether (75 mL) and transferred to a 250-mL separatory funnel. The round-bottomed flask was rinsed with two 10-mL portions of 1N aqueous NaOH that were added to the separatory funnel. The aqueous layer was removed, and the organic layer was washed with 0.5N NaOH (50 mL).

The aqueous layer was transferred to a 250-mL Erlenmeyer flask and cooled in an ice bath for 2 min. Aqueous HCl (4N) was added in 10-mL portions over 5 min until pH 2 was reached (40 mL total). A white precipitate formed after 35 mL of HCl solution had been added. The aqueous layer was extracted with diethyl ether (3×75 mL), and the combined clear, colorless organic layers were dried over $Na_2SO_4$, decanted into a 500-mL round-bottomed flask, and concentrated under reduced pressure (~30 torr→1 torr) to yield 5.5 g of a white foamy solid that was maintained at 1 torr for 30 min. The foamy solid was dissolved in diethyl ether (150 mL), and t-BuNH$_2$ (2.5 mL) was added via syringe. A white precipitate formed, the flask was placed in an ice bath, and the mixture was stirred for 45 min. The mixture was filtered through a 10-cm diameter Buchner funnel, rinsing with ice cold $Et_2O$ (3×25 mL). The white precipitate was transferred to a 500-mL round-bottomed flask and maintained at 1 torr for 2 h (6.1 g, 18.3 mmol). The product was taken up in THF (100 mL), heated to reflux, and treated with EtOH in 1-2-mL portions until the solid dissolved completely (~15 mL EtOH total). The flask was capped with a plastic stopper and allowed to cool to room temperature for 30 min. The flask was transferred to a 4° C. refrigerator and maintained at that temperature for 16 h. The fluffy white precipitate was isolated by filtration on a 10-cm diameter Buchner funnel, rinsing with ice cold THF (3×25 mL). The precipitate was transferred to a 200-mL round-bottomed flask and maintained at 1 torr for 4 h. Yield: 3.96-4.23 g (11.9-12.7 mmol, 48-51% yield from imine). The enantiomeric excess was determined to be 98-99% by HPLC analysis of the benzyl ester (range of two experiments).

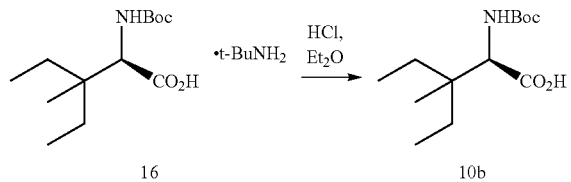 [SMILES: "·t-BuNH2" ; CCC(C)(CC)[C@@H](NC(=O)OC(C)(C)C)C(=O)O ; CCC(C)(CC)[C@@H](NC(=O)OC(C)(C)C)C(=O)O]

The free acid was isolated by partitioning the salt (100 mg) between aqueous 1N HCl (10 mL) and diethyl ether (10 mL). The organic layer was washed with brine (10 mL), dried over $Na_2SO_4$, and concentrated in vacuo to provide (R)-2-(tert-butoxycarbonylamino)-3-ethyl-3-methylpentanoic acid (10b) as a viscous, colorless oil (>90% recovery). $[\alpha]_D^{25}$=−11.6° (c 2.0, EtOAc). The compound exists as a 6:1 mixture of rotamers in $CDCl_3$; resonances corresponding to the minor rotamer are indicated with a * (many resonances for the minor rotamer are indistinguishable from those reported for the major rotamer, and are not reported). $^1$H NMR (500 MHz, $CDCl_3$): δ 5.63 (1H, br s)*, 5.00 (1H, d, J=9.5 Hz), 4.31 (1H, d, J=9.0 Hz), 4.08 (1H, br s)*, 1.44 (9H, s), 1.41-1.38 (4H, m), 0.90 (3H, s), 0.88-0.84 (6H, m). $^{13}$C{$^1$H} NMR (100 MHz, $CDCl_3$): δ 177.7, 156.6*, 155.8, 81.6*, 80.1, 60.4*, 58.8, 39.7, 39.3*, 28.5, 28.3, 27.9, 20.3. IR (cm$^{-1}$): 2971 (m), 1709 (s), 1656 (s), 1503 (m), 1395 (m), 1368 (m), 1244 (w), 1161 (s), 909 (m), 731 (m). LRMS (ESI): 282.2 (100%) [M+Na]$^+$.

Preparation of (R)-benzyl 2-(tert-butoxycarbonylamino)-3-ethyl-3-methylpentanoate for chiral HPLC analysis (11b)

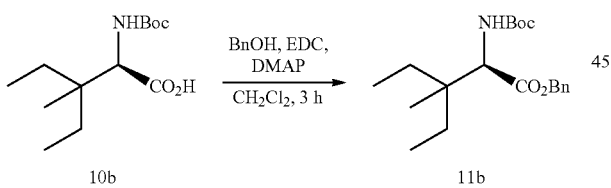

A 2-dram vial containing a small stir bar was charged with (R)-2-(tert-butoxycarbonylamino)-3-ethyl-3-methylpentanoic acid (10b) (10 mg, 0.04 mmol), $CH_2Cl_2$ (1 mL), 4-dimethylaminopyridine (2 mg, 0.02 mmol, 0.5 equiv), benzyl alcohol (20 μL, 0.2 mmol, 5 equiv), and EDC (20 mg, 0.1 mmol, 2.5 equiv). The solution was stirred at room temperature for 3 h, and then diluted with 10 mL $Et_2O$. The mixture was washed with water (2×10 mL), saturated aqueous $NaHCO_3$ (10 mL), and brine (10 mL). The organic layer was dried over $Na_2SO_4$ and concentrated under reduced pressure. The residue was purified by flash column chromatography on silica gel (7:1 hexanes/$Et_2O$) and analyzed by chiral HPLC analysis: (AD-H, 1 mL/min, 5% IPA/hexanes, 210 nm): $t_R$(major)=10.42 min, $t_R$(minor)=12.87 min.

What is claimed is:

1. A compound or pharmaceutically acceptable salt thereof selected from the formula (I):

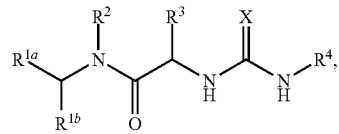

wherein

X is selected from O, S and $NR^5$;

$R^{1a}$ and $R^{1b}$ is optionally substituted aryl;

$R^2$ is hydrogen, optionally substituted alkyl;

$R^3$ is optionally substituted alkyl, optionally substituted aryl, optionally substituted cycloalkyl, optionally substituted heteroaryl, optionally substituted heterocyclyl, optionally substituted aralkyl, optionally substituted heteroaralkyl, or optionally substituted heterocyclylalkyl;

$R^4$ is optionally substituted alkyl, optionally substituted cycloalkyl, optionally substituted aryl, optionally substituted heteroaryl, optionally substituted heterocyclyl, optionally substituted heteroaralkyl, optionally substituted aralkyl or optionally substituted heterocyclylalkyl;

$R^5$ is hydrogen, alkyl, aryl, or arylalkyl.

2. The compound of claim 1, wherein the compound of formula (I) is enantiomerically enriched for the R isoform.

3. The compound of claim 1, wherein the compound is a compound of formula (Ia)

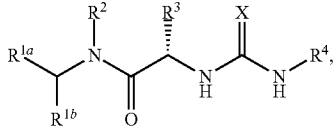

wherein the compound has an enantiomeric excess (ee) of at least about 50%.

4. The compound of claim 1, wherein the compound is a compound of formula (Ib)

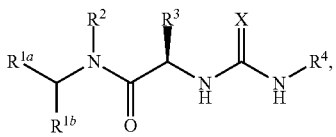

wherein the compound has an ee of at least about 50%.

5. The compound of claim 1, wherein the compound of formula (I) is enantiomerically enriched for the S isoform.

6. The compound of claim 1, wherein X is selected from O and S.

7. The compound of claim 6, wherein X is S.

8. The compound of claim 1, wherein $R^{1a}$ is phenyl.

9. The compound of claim 1, wherein $R^{1b}$ is phenyl.

10. The compound of claim 1, wherein the compound of formula (I) is selected from a compound of formula (Ic):

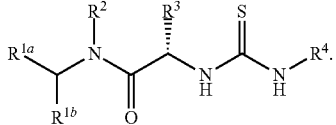

11. The compound of claim 1, wherein the compound of formula (I) is selected from a compound of formula (Id):

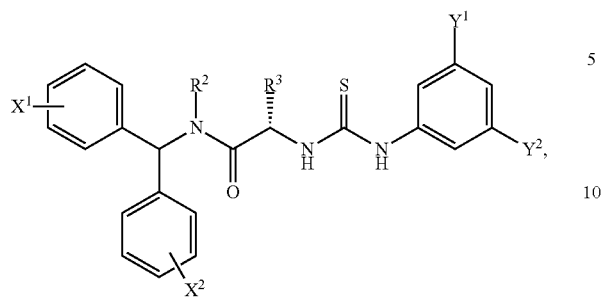
wherein $X^1$, $X^2$, $Y^1$ and $Y^2$ are each independently selected from hydrogen, alkyl, alkoxy or haloalkyl.
12. The compound of claim 11, wherein $Y^1$ or $Y^2$ is haloalkyl.
13. The compound of claim 1, wherein the compound of formula (I) is
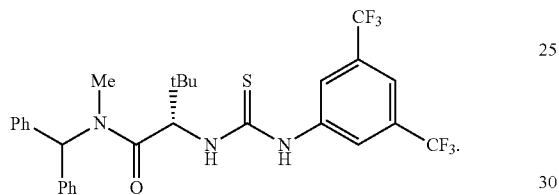
* * * * *